(12) United States Patent
Karbowniczek et al.

(10) Patent No.: US 12,221,614 B2
(45) Date of Patent: Feb. 11, 2025

(54) REPROGRAMMING VECTORS

(71) Applicant: Touchlight IP Limited, Hampton (GB)

(72) Inventors: Kinga Karbowniczek, Hampton (GB); Lisa Caproni, Hampton (GB); John Tite, Hampton (GB); Tristan McKay, Manchester (GB); Christopher Thornton, Manchester (GB)

(73) Assignee: Touchlight IP Limited, Hampton (GB)

( * ) Notice: Subject to any disclaimer, the term of this patent is extended or adjusted under 35 U.S.C. 154(b) by 1106 days.

(21) Appl. No.: 17/044,680

(22) PCT Filed: Apr. 5, 2019

(86) PCT No.: PCT/GB2019/051000
§ 371 (c)(1),
(2) Date: Oct. 1, 2020

(87) PCT Pub. No.: WO2019/193361
PCT Pub. Date: Oct. 10, 2019

(65) Prior Publication Data
US 2021/0147869 A1     May 20, 2021

(30) Foreign Application Priority Data
Apr. 5, 2018 (GB) .................................. 1805683

(51) Int. Cl.
*C12N 15/85* (2006.01)
*C12N 5/074* (2010.01)

(52) U.S. Cl.
CPC .......... *C12N 15/85* (2013.01); *C12N 5/0696* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2506/1307* (2013.01)

(58) Field of Classification Search
None
See application file for complete search history.

(56) References Cited

U.S. PATENT DOCUMENTS

2011/0065103 A1* 3/2011 Sahin .................... C12N 5/0696
435/173.6

FOREIGN PATENT DOCUMENTS

| JP | 2011505814 A | 3/2011 |
| WO | WO 2009/077134 A2 | 6/2009 |
| WO | WO 2010/086626 A1 | 8/2010 |
| WO | WO 2012/017210 A1 | 2/2012 |
| WO | WO 2016/132129 A1 | 8/2016 |
| WO | WO 2016/195598 A1 | 12/2016 |

OTHER PUBLICATIONS

Narsihn et al. Generation of adult human induced pluripotent stem cells using nonviral minicircle DNA vectors (2011) Nature Protocols, 6, pp. 78-88. (Year: 2011).*
Nafissi et al. Construction and Characterization of an in-vivo Linear Covalently Closed DNA Vector Production System (2012) Microbial Cell Factories, 11, pp. 1-13. (Year: 2012).*
Okita et al. A more efficient method to generate integration-free human iPS cells (2011) Nature Methods, 8, pp. 409-412 (Year: 2011).*
Nafissi, N. et al., "Construction and Characterization of an in-vivo Linear Covalently Closed DNA Vector Production System", Microbial Cell Factories, vol. 11, pp. 1-13 (Dec. 2012).
Wong, S. et al., "DNA Ministrings: Linear-Covalently Closed Minivectors for Use in Non-Viral Gene Therapy with Applications Toward Ovarian Cancer," Molecular Therapy, vol. 23, Sppl 1, pp. 5229-5230 (2015).
Wong, S. et al., "Production Double-stranded DNA Ministrings", Journal of Visualised Experiments, vol. 108, article No. e53177 (2016).
Wong, S. et al., "Optimizations in the Production of DNA Ministrings, Linear-Covalently Closed DNA Minivectors for Use in Non-Viral Gene Therapy," Molecular Therapy, vol. 25, No. 5, p. 358 (2017).
Nafissi, N. et al., "DNA Ministrings: Highly Safe and Effective Gene Delivery Vectors," Molecular Therapy Nucleic Acids, vol. 3, No. 6, article No. e165 (2014).
Schakowski, F. et al., "Minimal Size MIDGE Vectors Improve Transgene Expression In Vivo," In Vivo, vol. 21, No. 1, pp. 17-23 (2007).
Kobelt, D. et al., "Preclinical study on combined chemo- and nonviral gene therapy for sensitization of melanoma using a human TNF-alpha expressing MIDGEDNA vector," Molecular Oncology, vol. 8, pp. 609-619 (2014).
Walther, W. et al., "Improved transfer efficiency and transgene expression in vitro and in vivo using the minimalistic nonviral MIDGE expression system," AACR—Annual Meeting Apr. 18-22, 2009, vol. 69, No. 9, Suppl, abstract No. 3788 (May 2009).
Mok, P.L. et al., "In vitro expression of erythropoietin by transfected human mesenchymal stromal cells," Cytotherapy, vol. 10, No. 2, pp. 116-124 (2008).

(Continued)

*Primary Examiner* — Kara D Johnson
*Assistant Examiner* — Maytee Marie Contes De Jesus
(74) *Attorney, Agent, or Firm* — Bookoff McAndrews, PLLC

(57) ABSTRACT

Reprogramming allows the "conversion" of any mature or somatic cell of the human or animal body into a pluripotent stem cell. Reprogramming can be performed through the introduction of exogenous factors, usually transcription factors, into the mature cell. This process allows the production of induced pluripotent stem cells without the use of embryos, with the advantage that they can be produced from an individual to return/re-implant to the same individual. The inventors have developed a method of transient expression of exogenous reprogramming factors using a transient vector, wherein the vector is a closed linear DNA. Surprisingly, pluripotent stem cells developed in this manner are stable and closer in phenotype to natural stem cells such as ESCs.

9 Claims, 25 Drawing Sheets
Specification includes a Sequence Listing.

(56) References Cited

OTHER PUBLICATIONS

Hu et al., "Generation of Hypoimmunogenic Induced Pluripotent Stem Cells for Allogeneic Cell and Tissue Transplantation", Thoracic and Cardiovascular Surgeon, vol. 66, Supp. 1, Jan. 2018.

Yu et al., "Nonviral minicircle generation of induced pluripotent stem cells compatible with production of chimeric chickens", Cell Reprogram, vol. 16, No. 5, pp. 366-378, Oct. 2014.

Andrews, P.W. et al., "Induction of Class I Major Histocompatibility Complex Antigens in Teratocarcinoma Cells by Interferon without Induction of Differentiation, Growth Inhibition, or Resistance to Viral Infection," Cancer Research, vol. 47, pp. 740-746 (1987).

Eggenberger, J. et al., "Type I interferon response impairs differentiation potential of pluripotent stem cells," PNAS, vol. 116, pp. 1384-1393 (2019).

Henderson, J.K. et al., "Preimplantation Human Embryos and Embryonic Stem Cells Show Comparable Expression of Stage-Specific Embryonic Antigens," Stem Cells, vol. 20, pp. 329-337 (2002).

International Search Report in International Application No. PCT/GB2019/051000, mailed Jul. 31, 2019 (5 pages).

Isogai, S. et al., "Preparation of Induced Pluripotent Stem Cells Using Human Peripheral Blood Monocytes," *Cellular Reprogramming*, vol. 20, pp. 347-355 (2018).

Nafissi, N., "Construction and Characterization of a Robust in vivo Technology for the Production of Superior DNA Vectors with Applications in Gene Therapy and Vaccine Development," Ph.D. Thesis, University of Waterloo, pp. 1-154 (2013).

Nanbo, A. et al., "The coupling of synthesis and partitioning of EBV's plasmid replicon is revealed in live cells," *The EMBO Journal*, vol. 26, pp. 4252-4262 (2007).

Narsinh, K.H. et al., "Generation of Adult Human Induced Pluripotent Stem Cells Using Non-Viral Minicircle DNA vectors," *Nature Protocol*, pp. 78-88 (2011).

Takahashi, K. et al., "Induction of Pluripotent Stem Cells from Mouse Embryonic and Adult Fibroblast Cultures by Defined Factors," *Cell*, vol. 126, pp. 663-676 (2006).

Yu, J. et al., "Human Induced Pluripotent Stem Cells Free of Vector and Transgene Sequences," *Science*, vol. 324, pp. 797-801 (2009).

Zhou, T. et al., "Generation of human induced pluripotent stem cells from urine samples," *Nature Protocols*, vol. 7, pp. 2080-2089 (2012).

Zhou, Y-Y. et al., "Integration-free Methods for Generating Induced Pluripotent Stem Cells," *Genomics Proteomics Bioinformatics*, vol. 11, pp. 284-287 (2013).

\* cited by examiner

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Forward primer for CAG Enhancer

<400> SEQUENCE: 1
acgccaatag ggactttcca                                              20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for CAG Enhancer

<400> SEQUENCE: 2 taggggggcgt acttggcata                                             20

<210> SEQ ID NO 3
<211> LENGTH: 17
<212> TYPE: DNA
<213> ORGANISM: Artificial Sequence
<220> FEATURE:
<223> OTHER INFORMATION: Forward primer for OCT 4

<400> SEQUENCE: 3
gcgatcaagc agcgact                                                 17

<210> SEQ ID NO 4
<211> LENGTH: 18
<212> TYPE: DNA
<213> ORGANISM: Artificial Sequence
<220> FEATURE:
```

```
<223> OTHER INFORMATION: Reverse primer for OCT 4

<400> SEQUENCE: 4
ttcaccttcc ctccaacc                                                 18

<210> SEQ ID NO 5
<211> LENGTH: 20
<212> TYPE: DNA
<213> ORGANISM: Artificial Sequence
<220> FEATURE:
<223> OTHER INFORMATION: Forward primer for SOX2

<400> SEQUENCE: 5
catgtcccag cactaccaga                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for SOX2

<400> SEQUENCE: 6
gggttttctc catgctgttt                                               20

<210> SEQ ID NO 7
<211> LENGTH: 18
<212> TYPE: DNA
<213> ORGANISM: Artificial Sequence
<220> FEATURE:
<223> OTHER INFORMATION: Forward primer for LIN28

<400> SEQUENCE: 7
tgtccaaatg caagtgag                                                 18

<210> SEQ ID NO 8
<211> LENGTH: 20
<212> TYPE: DNA
<213> ORGANISM: Artificial Sequence
<220> FEATURE:
<223> OTHER INFORMATION: Reverse primer for LIN28

<400> SEQUENCE: 8
gcaggttgta gggtgattcc                                               20

<210> SEQ ID NO 9
<211> LENGTH: 21
<212> TYPE: DNA
<213> ORGANISM: Artificial Sequence
<220> FEATURE:
<223> OTHER INFORMATION: Forward primer for NANOG

<400> SEQUENCE: 9
tttgtgggcc tgaagaaaac t                                             21

<210> SEQ ID NO 10
<211> LENGTH: 21
<212> TYPE: DNA
<213> ORGANISM: Artificial Sequence
<220> FEATURE:
<223> OTHER INFORMATION: Reverse primer for NANOG

<400> SEQUENCE: 10
agggctgtcc tgaataagca g                                             21
```

```
<210> SEQ ID NO 11
<211> LENGTH: 19
<212> TYPE: DNA
<213> ORGANISM: Artificial Sequence
<220> FEATURE:
<223> OTHER INFORMATION: Forward primer for E-Cadherin

<400> SEQUENCE: 11
tgcccagaaa atgaaaaag                                                    19

<210> SEQ ID NO 12
<211> LENGTH: 20
<212> TYPE: DNA
<213> ORGANISM: Artificial Sequence
<220> FEATURE:
<223> OTHER INFORMATION: Reverse primer for E-Cadherin

<400> SEQUENCE: 12
gtgtatgtgg caatgcgttc                                                   20

<210> SEQ ID NO 13
<211> LENGTH: 20
<212> TYPE: DNA
<213> ORGANISM: Artificial Sequence
<220> FEATURE:
<223> OTHER INFORMATION: Forward primer for RN18S1

<400> SEQUENCE: 13
acacggacag gattgacaga                                                   20

<210> SEQ ID NO 14
<211> LENGTH: 21
<212> TYPE: DNA
<213> ORGANISM: Artificial Sequence
<220> FEATURE:
<223> OTHER INFORMATION: Reverse primer for RN18S1

<400> SEQUENCE: 14
ggacatctaa gggcatcaca g                                                 21
```

REPROGRAMMING VECTORS

CROSS-REFERENCE TO RELATED APPLICATIONS

This application is a U.S. national stage filing under 35 U.S.C. § 371 of International Application No. PCT/GB2019/051000, filed on Apr. 5, 2019, which claims the benefit of priority to GB Application No. 1805683.8, filed on Apr. 5, 2018.

SEQUENCE LISTING

This application contains a sequence listing, submitted electronically in ASCII format under the filename Sequence_Listing.txt, which is incorporated by reference herein in its entirety. The ASCII copy of the sequence listing was created on Sep. 23, 2020, and is 3,039 bytes in size.

BACKGROUND TO THE INVENTION

Reprogramming allows the "conversion" of any mature or somatic cell of the human or animal body into a pluripotent stem cell. Reprogramming can be induced through the introduction of exogenous factors, usually transcription factors, into the mature cell. This process allows the production of induced pluripotent stem cells without the use of embryos, with the advantage that they can be produced from an individual to return/re-implant to the same individual.

The cell lines established by reprogramming are named induced pluripotent stem cells (iPSCs) and demonstrated the same pluripotency and self-renewal properties that are characteristic of embryonic stem cells (ESCs).

Induced pluripotent stem cells are capable of unlimited proliferation and have the potential to differentiate into all cell types of the body, and are therefore useful in disease modelling and drug discovery. Stem cell research holds great promise for the generation of cell-based therapeutics, and to assist with research of human development and in regenerative medicine. Genetic reprogramming of human somatic cells to human induced pluripotent stem cells (hiPSCs) could offer replenishable cell sources for many research uses and ultimately therapies. For example, physiological and pathological responses of human cell populations can be assessed using induced stem cells.

Inducing the generation of pluripotent stem cells from mature cell types can be performed by many methods, but the majority involve the expression of exogenous reprogramming factors, in order to induce the reprogramming. Successful iPSC generation generally requires the expression of reprogramming factors for two to four weeks. This window is such that it prevents the use of a single transfection of a transient vector. Therefore, these exogenous reprogramming factors can be provided by multiple applications of transient DNA expression vectors, messenger RNA or protein. Alternatively the single transduction/transfection of genome integrating retroviral vectors or non-integrating episomal vectors will provide long-term expression. Methods that use integration of a DNA cassette into the host genome of the transfected cell are less desirable as this insertional mutagenesis can limit the utility of the cells in both research and clinical applications, even if subsequently the genes encoding the exogenous reprogramming factors are silenced or excised. Therefore, an advantage of using non-integrating episomal vectors is that serial propagation of the cells results in dilution and eventual removal of the DNA vector, thus ensuring that the genetic material that they carried is eventually lost.

Episomal plasmids (circular double stranded DNA) currently used for reprogramming are OriP/EBNA1 (Epstein-Barr nuclear antigen-1)-based episomal vectors. Derived from the Epstein-Barr virus (EBV), OriP/EBNA1 vectors are suitable for introducing reprogramming factors into somatic cells, as they can be transfected without packaging into viral delivery vectors. The cis-acting OriP element and a trans-acting EBNA1 gene ensure the stable extrachromosomal replication of OriP/EBNA1 vectors in mammalian cells. The OriP/EBNA1 vectors replicate only once per cell-cycle, and the EBNA1 protein enables plasmids carrying OriP both to duplicate and to segregate efficiently in proliferating cells. EBNA1 ultimately tethers plasmids to host chromosomes for mitotic stability. However, although EBNA1 is well-characterised; its role as an oncogene is less well defined. It is consistently expressed in EBV-associated cancers. Therefore, despite the mechanisms to eliminate the episomal plasmids from the iPSCs, there is a possibility some EBNA1 coding sequences may be retained. Persistent expression of EBNA1 has been demonstrated to cause cellular DNA damage. Indeed, IPSCs generated using EBNA1 vectors have been demonstrated to accumulate genetic mutations to a greater extent than ESCs. Additionally, the expression of the EBNA1 protein is known to influence gene expression within a cells with potentially hundreds of genes activated as a consequence of EBNA1 presence. The EBV-derived EBNA1 protein could also increase immune cell recognition of transfected cells, which may have an implication if expression is not entirely eliminated. In the Examples a comparison of interferon expression levels in reprogrammed cells is conducted. These results demonstrate that cells reprogrammed using OriP/EBNA1 containing plasmids resulted in an increase in the expression of interferon genes and other immune system related genes. Moreover, the transcriptional and epigenetic consequences of prolonged EBNA1 expression have not been fully explored and likely have a negative effect on any disease model generated from iPSC. However, balanced against these potential disadvantages is the fact that without OriP/EBNA1, plasmids are not retained for a sufficient period of time to effect reprogramming, particularly of mature somatic cell types.

The OriP/EBNA1 vector can be replicated once per cell cycle and it is not rapidly eliminated, the way regular transient plasmids are. Under nonselective conditions, the plasmid is eliminated at a rate of about 5% per cell cycle (Nanbo, A., Sugden, A., and Sugden, B. (2007). EMBO J 26, 4252-4262). It therefore takes at least 14 passages for these vectors to be eliminated to satisfactory levels. In order to keep the cells alive, it is necessary to subculture the cells into a new vessel. This subculture is known as a "passage." A passage number is the number of times a cell culture has been subcultured. During these passages, the inventors have observed that spontaneous differentiation of some cells may occur, leading to the need to cut out these cells or abandon the cells entirely. Therefore, whilst the iPSCs are generated within 30 days of transfection, the cells have to be maintained in culture for months in order to ensure the loss of the vector. Spontaneous differentiation may occur during these numerous passages complicating scale-up processes required for application in regenerative medicine and increasing the potential for EBNA1-mediated genomic mutations.

Alternatively, minicircle vectors have been proposed for use in reprogramming without the use of OriP/EBNA1. These are minimal vectors containing only the eukaryotic promoter and cDNA(s) that will be expressed. A minicircle vector expressed in human adipose stroma/stem cells (hASCs) was able to reprogram just 0.005% of the transfected cells in approximately 28 days (Narsinh K H, Jia F, Robbins R C, Kay M A, Longaker M T, Wu J C. Nature Protoc. 2011; 6:78-88). However, these cells (hASCs) already have some multi-potency characteristics suggesting they are easier to reprogram to pluripotency. This method was even less efficient at reprogramming neonatal fibroblasts and there are no published reports of successful reprogramming of other somatic cells. Indeed, the Narsinh et al caution that the "protocol as described here has not yet been successfully applied to the reprogramming of human dermal fibroblasts derived from adult sources." The use of minicircle vectors is therefore limited presently to multipotent hASCs which are isolated from adipose tissue. Such tissue can be harvested in very large quantities during lipoaspiration procedures, which is an invasive technique. Some groups have found that minicircles require repeated transfection in order to provide sufficient levels of expression. It is desirable to be able to reprogram somatic cells from easily accessible sources, and that are mature. Minicircles are double stranded circular DNA molecules, similar to plasmids, but smaller. Whilst in principle they appear to be a solution to the use of plasmids, in practice they are difficult and time consuming to produce. The inventors have noted that the minicircle production protocol results in the retention of some minimal bacterial DNA, which is undesirable. Methylation marks on bacterial DNA may have the effect of supressing gene expression from the vector in human cells, which reduces the utility of the vector and inducing innate immune responses to bacterial DNA.

To fulfil the promise of human therapeutic use, human iPSCs will ideally be free of exogenous DNA and have not been exposed to prokaryotic DNA sequences. After removal of the episomal vector, iPS cells completely free of vector and transgene sequences are derived that are similar to human embryonic stem (ES) cells in proliferative and developmental potential. "Foot-print free" cells are most desirable for therapeutic uses. The usefulness of iPSCs will rely highly upon their genomic integrity and stability, and therefore stable cells are highly desirable.

Human therapeutic use of iPSCs has yet to be fully realised, and to date, those wishing to implement clinical trials with iPSCs have had to prove by genome sequencing that none of the actions taken to promote reprogramming have had a deleterious effect on the genome of the implanted cells. Therefore, the use of reprogramming techniques which are also essentially early oncogenic events are likely to be phased out as far as possible in order to ensure that transplanted cells do not become oncogenic in their new setting. Therefore, for example, the reduction of the use of elements that are known to be oncogenic, such as suppression of p53, inclusion of c-Myc and use of EBNA1, can only improve the take-up of iPSC as a cell therapy option.

To date the applicants are not aware of a robust, reproducible and scalable mechanism for generating completely xeno-free, cGMP-compliant DNA vectors to elicit iPSC reprogramming.

The inventors have thus developed a method of transient expression of exogenous reprogramming factors using a non-episomal transient vector, wherein the vector is a closed linear DNA. The inventors have generated new data showing the unexpected and exceptional observation that closed linear DNA vectors are able to promote iPSC reprogramming. Remarkably, the inventors have found that closed linear DNA vectors have the capability of maintaining long-term expression in reprogramming without the need for any mechanism of chromosomal attachment, retention or segregation. Surprisingly, the closed linear DNA molecules are able to maintain long-term expression and effect reprogramming without p53 suppression. Further, the cells derived using a transfection of closed linear DNA appear to be more stable than cells transfected with a comparable circular plasmid carrying OriP/EBNA1, since the closed linear DNA constructs are naturally lost from the cells much more rapidly than plasmids carrying OriP/EBNA1. This is supported by the data presented on FIGS. 14A and 14B. These results are surprising, because most vectors without the use of chromosomal scaffold attachment and/or p53 suppression are not maintained for a sufficient period to express the necessary reprogramming factors. Further, the closed linear DNA vectors appear to effect reprogramming without the requirement for accessory sequences, elements or expression cassettes. The inventors have also found that closed linear DNA vectors were able to effect reprogramming of cells that were intransigent to reprogramming using standard OriP/EBNA1 based methods, see Example 5 and FIG. 11. Surprisingly, pluripotent stem cells developed in this manner are stable and closer in phenotype to natural stem cells such as embryonic stem cells.

SUMMARY OF THE INVENTION

The inventors have found that it is possible to reprogram a somatic cell using a one or more closed linear DNA vectors encoding reprogramming factors. If a somatic cell is transfected in this fashion and cultured for a sufficient period of time it is possible to obtain a stable and homogenous population of induced pluripotent stem cells.

A sufficient period of time/sufficient time is usually about 30 days, i.e. a period of 25 to 35 days, any one of 21, 22, 23, 24, 25, 26, 27, 28, 29, 30, 31, 32, 33, 34, 35 days.

The present invention thus relates to the use of a closed linear DNA vector encoding one or more reprogramming factors for producing induced pluripotent stem cells.

The present invention further relates to a method of producing induced pluripotent stem cells (iPSCs) comprising introducing one or more closed linear vector(s) comprising one or more reprogramming factors into a population of somatic cells, and culturing said cells to effect expression of the one or more reprogramming factor(s). Said introduction may be via transfection/nucleofection. The cells may be cultured for sufficient time, for example about 15-30 days to induce the reprogramming of the cells to pluripotency.

The required reprogramming factors for any part of this invention can all be encoded on one closed linear DNA vector, or the required reprogramming factors can be divided amongst two or more closed linear DNA vectors. Any number of closed linear DNA vectors can be used. Two or more closed linear DNA vectors may be used, or 3, 4, 5, 6, 7, 8 or more.

The closed linear DNA vector(s) may lack sequences for chromosomal scaffold attachment and replication, such as OriP/EBNA1. Further or alternatively, the closed linear DNA vectors may lack sequences for the suppression of p53, for example by RNA interference.

The reprogramming factors expressed by the closed linear DNA vector(s) may be any reprogramming factor required in order to reprogram a mature cell into an iPSC. The reprogramming vectors may be natural, modified or synthetic factors. They may be one or more Yamanaka factors. The closed linear DNA vector(s) may be used to transfect a somatic cell in order to produce an induced pluripotent stem cell. Somatic is generally used to refer to the cells of the body in contrast to the germ line cells, and encompasses all cell types of the body other than egg or sperm cells.

In order to effect reprogramming, the closed linear DNA vector(s) are transfected into the somatic cell. Any method of transfection may be used, and may depend upon the type of donor cell undergoing transfection. Nucleofection may be required in some instances.

The transfected cells are then cultured using appropriate conditions to permit expression of the reprogramming factors from the closed linear DNA vectors. Conditions for permitting reprogramming are generally known in the art, and any appropriate conditions may be selected. Ideally, for human therapeutic use, the culturing may be performed in a feeder-free system, such that the cells obtained are free of any animal component contamination (xenofree). This culturing step is performed for a sufficient time in order for the cells to be induced into pluripotency. Sufficient time is described previously.

Closed linear DNA is generally understood to be double-stranded DNA covalently closed at each end. There is, therefore, no free 3' or 5' ends to the DNA. The double stranded DNA in the linear section is complementary in sequence. When denatured, closed linear DNA may form a single stranded circle. The DNA may be closed at each end by any suitable sequence, forming any secondary structure, such as a hairpin or a hairpin loop, or more complex structures such as cruciform. The sequence at the closed ends of the linear DNA may be complementary or non-complementary. The closed linear DNA may be made by any suitable method. Given the use of the DNA vector in human cells, it may be preferred to ensure that the closed linear DNA is free from any prokaryotic DNA sequences, such as antibiotic resistance genes or origins of replication.

The present invention further relates to the cells made using the method of the invention, since the present inventors have found that these are of a higher grade or are more stable compared to those transfected using alternative episomal vectors.

The invention therefore further relates to a population of induced pluripotent stem cells, wherein said population of cells is made using any use or method as described here. Said population of cells may no longer harbour the closed linear DNA vectors, since these are naturally lost during cell maintenance, making these much safer than cells induced by current methods, including retroviral methods where the reprogramming factors are not removed. Said invention therefore includes a therapeutic and/or Good Manufacturing Practice (GMP) grade population of stable, pluripotent stem cells induced with a closed linear DNA vector encoding at least one reprogramming factor.

The cells of the invention are preferably human.

When cultured, pluripotent stem cells are generally densely packed. When differentiated, the cells are less densely packed, and therefore in a mixed cell population (pluripotent and differentiated) a small proportion of differentiated cells can appear to be more numerous. Pluripotent stem cell colonies are graded by those skilled in the art. Colonies in grade A are clear pluripotent stem cell colonies with clean edges and borders, the cells are densely packed and no differentiation is seen, nor disperse cells around the colony edge. Colonies in grade B have spontaneously differentiated cells at the edge, which are identified as they are more disperse. Colonies in grade C have cells which have mainly spontaneously differentiated, leaving only pockets of pluripotent stems in the disperse cells.

The inventors have identified that many more of the colonies obtained using closed linear DNA vectors are classified as category A, particularly when compared to cells obtained using the current state of the art techniques.

Indicative data for stability is the generation of colonies which are classified as Grade A. Such analysis and classification includes the visual (including by microscope) observation of the relevant cell colonies, looking in particular at the borders of the colonies to examine for spontaneous differentiation. Since differentiated cells are less densely packed, this leads the colony to have more disperse edges. Colonies with clean edges or borders are placed into grade A, and are therefore defined as more stable, since they are retaining a pluripotent phenotype. Cells that are not stable in the pluripotent state spontaneously differentiate. Thus, visual inspection allows the stability of the cells in the colony to be determined.

Spontaneous differentiation may also be determined using the presence of either a marker for differentiation, or a marker for pluripotency. For example, SSEA-1 is a marker of very early differentiation/exit from the pluripotent state, and TRA-1-60 and TRA-1-81 are human markers of pluripotency. A colony may be extracted and subjected to analysis using fluorescence activated cell sorting (FACS). The cells are dissociated from the culture and individual cells are labelled using fluorophore-conjugated antibodies to the particular cell marker (i.e. SSEA-1 or TRA-18-1). The cells are then separated depending on whether they are labelled with the fluorophore or not. It is now possible to perform FACS on live cells and continue culturing after sorting.

Additionally, alkaline phosphatase (AP) activity is associated with the pluripotent state and can be quantified using a colorimetric substrate assay which may be applied to individual cells or cell colonies. It is possible to stain cells for AP activity and visually determine that the cells in a colony are pluripotent. This stain is sensitive enough for the cells to be inspected on a plate. Additionally, it is possible to use technology to determine the levels of AP staining in a colony to provide a quantitative result. This quantitative data allows comparison between methodologies. AP may allow the skilled person to grade a colony, if further confirmation is required.

These are all examples of ways in which the stability of a pluripotent stem cell colony may be determined.

The present invention therefore includes a population of stable pluripotent stem cells induced with a closed linear DNA vector, in particular a population of stable pluripotent stem cells induced with a closed linear DNA vector which does not contain EBNA1, or a functional variant or derivative thereof. Preferably the closed linear DNA vector also lacks the OriP sequence or functional variants or derivatives thereof. Optionally the closed linear DNA vector(s) lack genes for chromosomal scaffold attachment. Further or alternatively, the closed linear DNA vectors may lack sequences for the suppression of p53.

The stable cells or reprogrammed cells of the invention are less likely to undergo spontaneous differentiation, a common issue with other methods of reprogramming. Indeed, in the examples it is shown that cells reprogrammed using reprogramming vectors encoded by closed linear DNA are more stable than those expressed by standard vectors (FIG. 5). In reprogramming, colonies are commonly observed with cells at the periphery which have lost their pluripotency and have differentiated. To deal with this issue, commonly cells are mechanically cut away from the colonies. The present inventors have observed that cells reprogrammed using closed linear DNA vectors encoding the reprogramming factors do not differentiate at the periphery and do not need to be excised. More colonies are classified as grade A. The stability of the iPS cells generated using reprogramming factors expressed by closed linear DNA vectors can be confirmed using FACs™ (fluorescence activated cell sorting) at various passage numbers (i.e. Passage 10, 15 etc.). The cells can be interrogated using early differentiation markers and/or pluripotency markers to enable the cell sorting. Stable iPS cells will have few, if any of the former markers, and more of the latter. Ideally, the iPSCs induced according to the methods of the invention will have low to no expression of the cell surface marker SSEA1 and express on their surface the cell surface marker SSEA3, TRA-1-60 or TRA-1-81.

When using FACS analysis to determine stability, it will be important to use an optimal gating strategy when assessing cell samples. Those skilled in the art will be aware of the factors that need to be considered when determining an appropriate gating strategy, in order to exclude debris, include appropriate negative controls, exclude non-viable cells, staining with shared markers if appropriate and setting up the appropriate fluorophore analysis plots. The results obtained will depend on the success of the gating strategy.

The cells of the invention preferably lack the closed linear DNA vector(s) used to induce their production.

Since the methods and uses of the invention result in a more genetically and phenotypically stable and safer iPSC population, these are therefore more likely to be able to be used clinically and/or therapeutically, the use of a closed linear DNA vector to obtain these cells is new. The invention therefore further relates to a composition for preparing therapeutically acceptable induced pluripotent stem cell comprising a closed linear DNA vector encoding at least one reprogramming factor. The invention therefore further includes a pharmaceutical composition comprising a closed linear DNA vector encoding at least one reprogramming factor and at least one pharmaceutically acceptable excipient.

DESCRIPTION OF FIGURES

FIG. 10A depicts the results from reprogramming experiments with a negative control and the plasmid proTLx-K. This plasmid contains the entire sequence of the corresponding closed linear DNA vector, with the addition of a backbone, and is in a double stranded circular format. The plasmid does not contain OriP/EBNA1 unless otherwise indicated. The first three panels for each cell type is a photograph of the cells on the depicted day. During these experiments only one potential colony formed. Alkaline Phosphatase Live Staining (AP) of this single colony proved negative, indicating that these cells are not pluripotent stem cells (last panels). Therefore, simply the sequence of the reprogramming factors present in the closed linear DNA vector sequence provided in a plasmid is not sufficient to effect reprogramming of the cells. FIG. 10B shows a comparison of a reprogramming experiment with the plasmid proTLx-k, closed linear DNA and the plasmid with inclusion of OriP/EBNA1. ProTLx-k transfected cells failed to reprogram fully, areas of partial reprogramming are highlighted, but no viable colonies are formed. By converting this plasmid to closed linear DNA, or including OriP/EBNA1 allowed for the production of primary colony formation. These results points towards the requirement for the structure of the vector for utility in reprogramming, and not just the sequence, as demonstrated in FIG. 11.

FIG. 20A (reactome pathway analysis of OriP-EBNA1 enriched genes) showing genes associated with the immune system, signal transduction, metabolism, metabolism of proteins, gene expression (transcription), developmental biology, disease, extracellular matrix organisation, haemostasis, cellular responses to external stimuli, transport of small molecules, vesicle-mediated transport, metabolism of RNA, cell cycle, muscle contraction, cell-cell communication, neuronal system, programmed cell death, chromatin organisation, organelle biosynthesis and maintenance, DNA repair, reproduction, circadian clock, DNA replication, mitophagy and digestion and absorption. FIG. 20B (Immune system responses-Orip-EBNA1) shows that reactome sub-categorisation shows Interferon alpha, beta and gamma signalling are the most strongly over-represented in OriP/EBNA1 when compared to dbDNA (closed linear DNA) mediated iPSC generation. Interleukin and NF-KB inflammatory signalling are also over-represented. Cytokine signalling in the immune system and innate immunity are the most over represented reactomes in OriP/EBNA1 when compared to dbDNA (closed linear DNA) mediated iPSC generation. The most significantly over-represented transcripts in OriP/EBNA1 iPSC compared to closed linear DNA iPSC were analysed using Reactome pathway analysis.

21A-IRF9, 21B-IRAK1, 21C-IFI27, 21D-IRAK4, 21E-IRF7, 21F-MYD88, and 21G-IRF1 and relative expression levels are shown.

Figure 22:
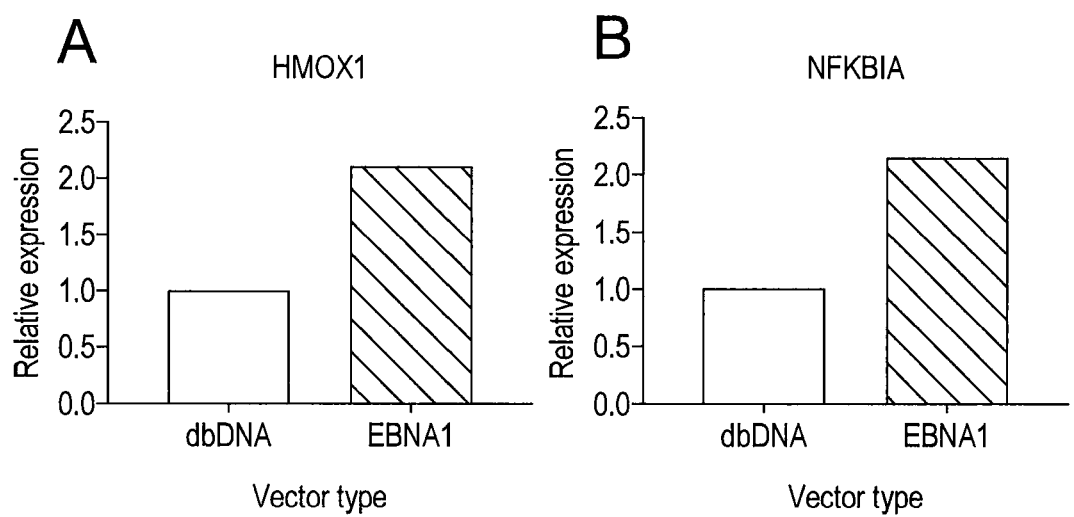

FIGS. 22 (A and B) Quantitative RT-PCR comparison of inflammatory markers in OriP/EBNA1 versus dbDNA (closed linear DNA) iPSC. Total RNA was extracted from iPSC generated using OriP/EBNA1 episomal plasmids or closed linear DNA vectors. FIG. 22, part A shows the data for HMOX1 (a marker of oxidative stress) and FIG. 22, part B NFKB1 (a marker of inflammation) are both upregulated in OriP/EBNA1-iPSC compared to closed linear (dbDNA)-iPSC.

Figure 23:
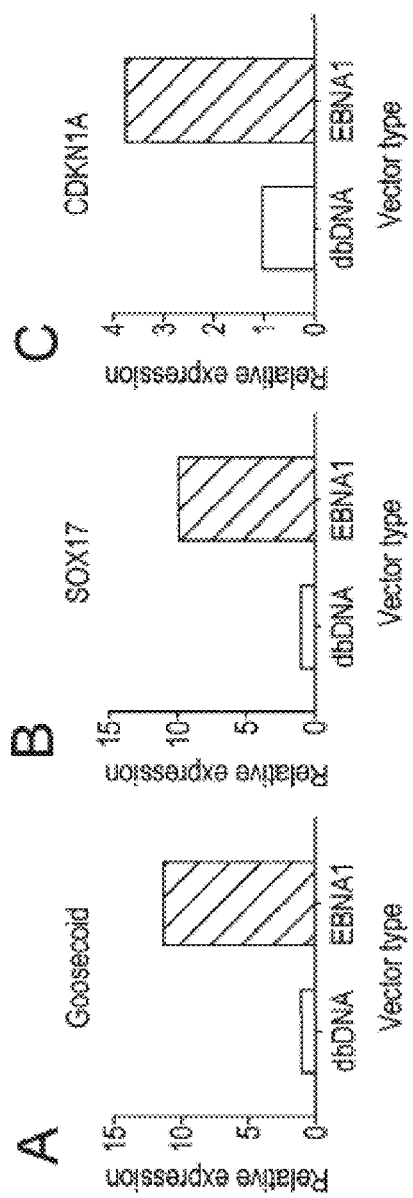

FIG. 23 (A to C) are plots which depict the upregulation of markers of differentiation in OriP/EBNA1-iPSC compared to closed linear DNA-iPSC (doggybone-closed linear DNA). Quantitative RT-PCR was used to evaluate transcripts representing mesendoderm formation and early endoderm as markers of early differentiation. In all instances there was increased markers of early differentiation in OriP/EBNA1-iPSC compared to closed linear DNA-iPSC cultured under steady state conditions. Furthermore, increased expression of CDKN1A (p21), a cell cycle inhibitor, in OriP/EBNA1-iPSC compared to dbDNA-iPSC. CDKN1A-mediated inhibition of proliferation is a further indicator of differentiation of pluripotent stem cells. FIG. 23, part A depicts goosecoid, FIG. 23, part B depicts SOX17, and FIG. 23, part C depicts CDKN1A. Relative expression values are plotted against vector type for the reprogramming step.

DETAILED DESCRIPTION

The inventors have developed a method of generating induced pluripotent stem cells using transient vector that lacks the means for tethering to and/or segregating with the cell's chromosomes during cell division or means to prolong maintenance of the vector in the cell. This has numerous advantages, not least that the use of potentially oncogenic EBNA1 or other expressed genes can be avoided. Further, since the expression of the encoded reprogramming factors is sufficient yet transient, this also ensures that the induced cells are not exposed to these factors for a prolonged period beyond the reprogramming process where expression could be deleterious. This could be beneficial, since some reprogramming factors are themselves known oncogenes, for example c-Myc. Thus a time-limited expression of such factors is preferable. The uses and methods developed by the present inventors ensures that the required factors are only expressed for the minimum amount of time required to induce pluripotency, and then expression is naturally lost as the cells are propagated, with the loss of the vector. The vector of the invention is not capable of replication in the cells. The use of this vector has been found to result in the production of stable pluripotent stem cell colonies, which are available for use prior to those made with standard OriP/EBNA1 vectors, since these cells must be cultured for longer to remove the episomal vector.

Pluripotency is supported by a complex system of signalling molecules and gene networks that are specific for pluripotent cells. The genes most highly implicated in the maintenance of pluripotency are Oct4, Sox2, and NANOG genes, which encode transcription factors. Induced pluripotent stem cells closely resemble ESCs in a broad spectrum of features. They possess similar morphologies and growth behaviours and are equally sensitive to growth factors and signalling molecules. Like ESCs, iPSCs can differentiate in vitro into derivatives of all three primary germ layers (neurectoderm, mesoderm, and endoderm). Pluripotency gene expression, such as NANOG expression, is only induced during the late stage and indicates faithful reprogramming. NANOG expression can, therefore, be used as an indicator of pluripotency, for example.

Thus, an outstanding method that allows the preparation of pluripotent stem cells from various somatic cell types while leaving the cells "footprint-free" (free of the genes which expressed the reprogramming factors) is of great interest to those desiring the therapeutic use of such cells. Ideally, somatic cells can be harvested from an individual, induced into a pluripotent state, modified as required, differentiated into the required cell type (if necessary) and re-introduced to the same individual. Thus, human and animal therapies envision autologous transplantation of cells following conversion to iPSC and subsequent differentiation, if required. Allogenic transplantation may be appropriate if the donor or original cells are harvested from sources such as cord blood.

In one aspect, the present invention thus relates to the use of a closed linear DNA vector encoding one or more reprogramming factors for producing induced pluripotent stem cells. One or more, or two or more closed linear DNA vectors may be required, as described previously.

The closed linear DNA vector may be used to transfect a cell, preferably a somatic cell, most preferably a mature somatic cell. The transfection may be carried out by any suitable means, some of which are described herein.

Following transfection, the cell is cultured using any suitable conditions known to assist in the reprogramming to a pluripotent stem cell; some of these methods are described herein.

The use may be of one closed linear DNA vector species, which encodes one or more reprogramming factors, or may be of two or more closed linear DNA vectors, each of which encodes at least one different reprogramming factor. Alone or in combination, the closed linear DNA vectors may supply to the cells the reprogramming factors necessary to induce pluripotency. It is possible that the closed linear DNA vectors supply a proportion of the required reprogramming factors, and the remaining required factors are supplied exogenously to the cell, in order to "top up" the effect of the expressed reprogramming factors in the cell. In this instance, the closed linear DNA could provide 50, 55, 60, 65, 70, 75, 80, 85, 90 or 95% or more of the reprogramming factors required for inducing pluripotency. The remaining proportion could be supplied exogenously, for example, by the factors being added directly to the culture medium of the cells.

It may be necessary to express one or more of the reprogramming factors in higher quantities than the others, and therefore particular reprogramming factors can be encoded on two or more closed linear DNA molecules, or one closed linear DNA vector can include two copies of the reprogramming factor in order to increase expression of that factor relative to the others. Alternatively, expression can be controlled by using independent promoters for each reprogramming factor. As a further alternative, expression can be controlled by using one or more IRES sequence (internal ribosome entry site) upstream of one or more of the reprogramming factors.

Thus, in one aspect, the present invention relates to a method of producing induced pluripotent stem cells (iPSCs) comprising introducing one or more closed linear vector(s) comprising one or more reprogramming factors into a population of somatic cells, and culturing said cells to effect expression of the one or more reprogramming factor(s).

The cells may be cultured until characteristics of pluripotency are observed, and such colonies isolated for further propagation, as required. Culturing conditions are known to those skilled in the art and some exemplary methods are discussed herein. The cells are cultured for a sufficient time for pluripotency to be induced.

The closed linear DNA may be introduced into the somatic cells via transfection. Any suitable transfection means may be used; some of which are described herein.

The required reprogramming factors for any part of this invention can all be encoded on one closed linear DNA vector, or the required reprogramming factors can be divided amongst two or more closed linear DNA vectors. Any number of closed linear DNA vectors can be used. One or more different closed linear vectors may be used in the methods or uses of the invention, in order to ultimately result in iPSCs. The closed linear DNA vectors may each express one or more different reprogramming factors. The closed linear DNA vectors may each express two or more reprogramming factors, such as 2, 3, 4, 5 or 6 reprogramming factors.

The closed linear DNA of any aspect of the invention preferably includes a promoter or enhancer operably linked to the reprogramming factors. One or more promoter or enhancers may be used, as required. Each may be linked to a different factor.

A "promoter" is a nucleotide sequence which initiates and regulates transcription of a polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "enhancer" includes full-length promoter regions and functional (e.g., controls transcription or translation) segments of these regions.

"Operably linked" refers to an arrangement of elements wherein the components so described are configured so as to perform their usual function. Thus, a given promoter operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence. Thus, the term "operably linked" is intended to encompass any spacing or orientation of the promoter element and the DNA sequence of interest (such as a reprogramming factor) which allows for initiation of transcription of the DNA sequence of interest upon recognition of the promoter element by a transcription complex. In the Examples, the CAG synthetic promoter fusion sequence is used. CAG stands for CMV enhancer, chicken beta-Actin promoter and rabbit beta-Globin splice acceptor site, a combined fusion for efficient expression. Thus, in this fusion, a cytomegalovirus (CMV) enhancer is used upstream of a chicken beta-Actin promoter, which has associated with it the first exon and the first intron of chicken beta-actin gene. This is a particularly useful sequence to use for these Examples, but other appropriate sequences may be used. The closed linear DNA vectors preferably lack the ability replicate and partition during division of the host/donor cell. Thus, the closed linear DNA vector(s) may lack any functional sequences for chromosomal scaffold attachment. Therefore, the closed linear DNA vectors preferably lack the sequence for EBNA1, or functional derivatives, variants or modifications thereof. Such functional derivatives, variants or modified version of EBNA1 may be 90% or more, preferably 95% homologous to the natural sequence for EBNA1. EBNA1 can attach a vector to host cell DNA via N-terminal hook motifs—LR1 and LR2 that bind to AT-rich chromosomal regions. The closed linear DNA may also or alternatively lack the sequence for OriP. OriP is a 1.7-kb region of the Epstein-Barr virus (EBV) chromosome that supports the replication and stable maintenance of vectors in human cells. OriP contains two essential components, called the DS and the FR, both of which contain multiple binding sites for the EBV-encoded protein, EBNA-1. The closed linear DNA vector preferably lacks the OriP sequence or functional derivatives thereof. Such functional derivatives or modified version of OriP may be 90% or more, preferably 95% homologous to the natural sequence for OriP. Functional as used herein means that the variant or derivative works in the same way as the unmodified version in the replication and portioning of the episomal vector. OriP sequences may also function as enhancers of gene expression. It may be possible to use fragments or portions of the OriP sequence that retain this ability to enhance gene expression, whilst not maintaining the ability to tether to the chromatin. Such fragments or portions of the OriP sequence would not be considered to be a functional derivative of OriP insofar as the retention of the sequence during cell division is concerned.

Other genes or sequences that may act as a chromosomal scaffold attachment include scaffold/matrix attachment region (S/MAR). Such sequences or functional homologues or derivatives that retain the ability to attach may also be absent from the closed linear DNA vector.

However, it is preferred that the closed linear DNA vector simply lacks a functional OriP/EBNA1 sequence and cannot, therefore, tether to the chromosome of the donor/host cell during cell division.

Closed linear DNA vectors can be designed to be minimal vectors, including only the sequences necessary for their desired function and structure (i.e. the sequence they are delivering and a sequence encoding the closed ends, for example a cruciform, hairpin or hairpin loops at the end of the double stranded linear section). Unnecessary or extraneous sequences (also described as bacterial or viral sequences) that may be excluded from closed linear DNA vectors may include bacterial origins of replication, bacterial selection markers (e.g. antibiotic resistance genes), and unmethylated CpG dinucleotides. By not including such sequences, this enables the creation of a "minimal" vector which does not contain extraneous genetic material. This may be preferred where the cells are to be used for therapeutic purposes, since no genetic material is introduced that could affect the performance of the vector or cause unnecessary side effects (i.e. antibiotic resistance genes).

Further, it may be desirable to omit sequences that are derived from mammalian viruses, other than promoter, enhancer or terminator sequences. Mammalian viral sequences may have the ability to promote integration of vector DNA into the host cell DNA. Therefore, the closed linear DNA may be free of viral sequences that promote integration. Such sequences may come from any mammalian virus, but in particular are derived from virus that has the potential to integrate within the host DNA, such as retroviruses. Other viral classes that have the capacity to integrate their DNA include Parvoviridae (including human parvovirus and Adeno-associated virus (AAV)), Hepadnaviridae (including Hepatitis B virus), Herpesviridae (Herpes virus), Papillomaviridae (including Human papillomavirus) and Polyomaviridae (including Simian virus 40). Elements that promote integration may include integrase enzymes or sequences such as Rep-binding sites in inverted terminal repeats.

In the Examples, it has been shown that the closed linear DNA vector(s) may lack any means for the suppression of p53. Knockout of the Tumour Protein 53 (p53) gene has been reported to facilitate reprogramming, but is also linked to genomic instability. The cell-cycle regulator p53 acts as an important safeguard mechanism, stopping cells from undergoing uncontrolled proliferation following DNA damage. Further, p53 has also been shown to act as a barrier to the reprogramming process. Although the inhibition of p53 is advantageous for reprogramming efficiency, it has also been found to cause genomic instability. The inventors of the present application found that closed linear DNA vectors could cause reprogramming even without sequences which cause the suppression of p53. Knockdown of p53 may be achieved by many means including expression of small interfering RNAs (siRNA) or short hairpin RNAs (shRNA). It is preferred that the closed linear DNA vectors lack both siRNA and shRNA targeted against p53, commonly denoted as sip53 and shp53.

The reprogramming factors expressed by the one or more closed linear DNA vector(s) may be any reprogramming factor required in order to reprogram a somatic cell into an iPSC. The reprogramming vectors may be natural, modified or synthetic factors. The reprogramming factors may be a polypeptide, glycopeptide or protein expressed from the closed linear DNA vector. Such reprogramming factors include transcription factors. A transcription factor is a protein that controls the rate of transcription of genetic information from DNA to messenger RNA, by binding to a specific DNA sequence. Alternatively, the reprogramming factor may be a functional Ribonucleic acid (RNA) molecule that is expressed from the closed linear Deoxyribonucleic acid (DNA). Such functional RNA molecules include microRNAs (miRNAs-short RNA molecules that bind to complementary sequences on messenger RNA and block expression of a gene). Embryonic stem cell-specific microRNA molecules (such as miR-291, miR-294 and miR-295) enhance the efficiency of induced pluripotency by acting downstream of c-Myc/L-Myc. Other types of RNA that may be expressed include ribozymes, aptamers, and small interfering RNAs (siRNAs). Further, the reprogramming factors may be long non-coding RNAs. These are longer than 200 nucleotides in length, do not encode peptides, and have a regulatory function. Long non-coding RNAs are important for cell differentiation and development. They have previously been shown to be capable of shutting down gene clusters, examples of long non-coding DNA including HOTAIR RNA and Xist RNA.

One or more of the reprogramming factors can be a transcription factor. For example, one or more may be a Yamanaka factor; which includes the transcription factors Myc, Oct3/4, Sox2 and Klf4. These were the first 4 factors shown which could induce a mature cell into pluripotency, as demonstrated by Yamanaka et al (Takahashi, K; Yamanaka, S (2006). "Induction of pluripotent stem cells from mouse embryonic and adult fibroblast cultures by defined factors". Cell. 126 (4): 663-76. doi: 10.1016/j.cell.2006.07.024).

However, since then, further work has demonstrated that other combinations of reprogramming vectors can be used. For example, the combination of OCT4, SOX2, NANOG, and LIN28 has been found to induce pluripotency in somatic cells.

Therefore, any combination of transcription factors can be used as reprogramming factors according to any aspect of the present invention. Any transcription factor may also be combined with other reprogramming factors, such as siRNA, miRNA, long non-coding RNA, ribozymes and/or aptamers. Oct-3/4 and certain products of the Sox gene family (Sox1, Sox2, Sox3, and Sox15) have been identified as transcriptional regulators involved in the induction process.

Additional genes, however, including certain members of the Klf family (Klf1, Klf2, Klf4, and Klf5), the Myc family (c-myc, L-myc, and N-myc), NANOG, and LIN28, have been identified to increase the induction efficiency.

Oct-3/4 (Pou5f1) is a member of the family of octamer transcription factors, and plays a crucial role in maintaining pluripotency. The presence of Oct-3/4 thus gives rise to the pluripotency and differentiation potential of embryonic stem cells.

The Sox family of transcription factors is associated with maintaining pluripotency in similar fashion to Oct-3/4. While Sox2 was the initial gene used for induction (Yamanaka), other transcription factors in the Sox family have been found to work as well in the induction process. Sox1, Sox3, Sox15, and Sox18 also generate pluripotent cells, although with decreased efficiency.

Klf4 of the Klf family of transcription factors was initially identified by Yamanaka as a factor for the generation of human pluripotent cells. However, others have noted that Klf4 was unnecessary for generation of human pluripotent cells. Klf2 and Klf4 were found to be factors capable of generating pluripotent cells, and related genes Klf1 and Klf5 may have a similar effect.

The Myc family of transcription factors are proto-oncogenes implicated in cancer. Yamanaka demonstrated that c-myc is a factor implicated in the generation of human pluripotent cells. Usage of the "myc" family of genes in induction of pluripotent stem cells is troubling for the eventuality use of these cells as clinical therapies. N-myc and L-myc have been identified to induce instead of c-myc with similar efficiency.

In embryonic stem cells, NANOG, along with Oct-3/4 and Sox2, is necessary in promoting pluripotency. It is possible to generate pluripotent stem cells with NANOG as one of the factors.

LIN28 is an mRNA binding protein expressed in embryonic stem cells. It has been demonstrated that LIN28 is a factor in pluripotent stem cell generation, sometimes in combination with OCT4, SOX2, and NANOG.

Glis1 is transcription factor that can be used with Oct-3/4, Sox2 and Klf4 to induce pluripotency, replacing c-Myc.

Thus, according to the present invention, one or more reprogramming factors may be selected from any combination of the following:

Oct 3/4, Sox2, Sox1, Sox3, Sox15, Sox18, Klf1, Klf2, Klf4, Klf5, c-myc, L-myc, and N-myc, NANOG, and LIN28.

At present, it is considered in the art that the minimum number of reprogramming factors supplied to a cell in total, from any source, is four. This minimum number appears to be necessary in order to promote the reprogramming. However, in future it may be possible to promote reprogramming using just two, three or more reprogramming factors.

The encoded reprogramming vectors may be functional derivatives, or variants of any of the sequences described herein. These functional derivatives or variants have the same functional effect in reprogramming, but have an altered sequence when compared to the wild-type sequences. The functional derivatives or variants are at least 90% identical, at least 95%, 96%, 97%, 98% or 99% identical to the wild-type sequence.

In a particular embodiment, the closed linear DNA provides expression of a proportion of the required reprogramming vectors to the cell; exogenously supplied reprogramming factors supplied to the cells during culturing are also required in order to reach pluripotency. A hybrid approach is therefore considered. These exogenous growth factors may be small chemicals that mimic the action of transcription factors, and include the histone deacetylase (HDAC) inhibitor valproic acid, inhibition of histone methyl transferase (HMT) with BIX-01294. These small molecule compounds can compensate for a reprogramming factor. However, in any hybrid approach at least 50% of the required reprogramming factors would be provided by expression of the closed linear DNA vector. This means that at least 2 out of 4 required factors would be provided on the closed linear DNA vector, for example. It may be preferred that at least 60, 70, 80, 90 or 95% of the required reprogramming factors are supplied via the closed linear DNA vectors.

The closed linear DNA vector(s) may be used to transfect a somatic cell in order to produce an induced pluripotent stem cell. Somatic cells can be stem cells or mature cells. These cells may be referred to as the "donor cells". Adult stem cells are undifferentiated cells, found throughout the body. They can multiply by cell division to replenish dying cells and regenerate damaged tissues. Adult or somatic stem cells have been identified in many organs and tissues, including brain, bone marrow, peripheral blood, blood vessels, skeletal muscle, skin, teeth, heart, gut, liver, ovarian epithelium, and testis. They are thought to reside in a specific area of each tissue called a "stem cell niche" and provide a source of cells for that tissue only. Types of adult stem cells include hematopoietic stem cells (these give rise to all the types of blood cells), Mesenchymal stem cells (present in many tissues—in bone marrow for example), Neural stem cells in (the brain and nervous system), Epithelial stem cells (digestive tract), Skin stem cells (basal layer of the epidermis and at the base of hair follicles). Adult stem cells may prove problematic to propagate once outside the body.

If mature cells are harvested as donor cells, this may come from any tissue, organ, body fluid or excreta from the body. Thus, the cells can be skin cells, hair follicle cells, blood cells, cells extracted from urine, cells collected by biopsy or the like from any tissue or organ including, but not limited to, bone, teeth, dental tissue, heart, lungs, brain, pancreas, liver, kidneys, bladder, uterus, intestine, stomach, gall bladder, muscle, fat, testis, mucous membrane, eye, foreskin, prostate, spleen or any other tissue.

Clinical applications of cell therapies require that tissue collection from patients be as minimally invasive as possible and harvesting human dermal fibroblasts by biopsy leaves a small scar on the patient's body. Pluripotent stem cells have recently been generated from human keratinocytes induced from plucked hair. Oral gingival and oral mucosa fibroblasts can be obtained less invasively; have also investigated for iPSC generation. Kidney cells excreted in urine are also a useful source of cells, and can also be collected non-invasively.

Cord blood is also another donor cell source. Cord blood-derived cells do not require invasive biopsy before introducing reprogramming factors. Banked cord blood cells are relatively uncomplicated for use in iPSC generation because their immunological information is already available, thus permitting allogenic transplantation to occur.

Peripheral blood cells are also an attractive cell source because the method for cell sampling from patients is less invasive.

However, any appropriate source of cells may be used as "donor cells" for the uses and methods of the present invention.

For therapeutic, clinical purposes, it is an aim to generate cells from the patient, and return these cells to the same patient (autologous transplantation), but the uses and methods of the present invention also extend to allogenic transplantation where cells from one subject are transferred to another.

In order to effect reprogramming, the closed linear DNA vector(s) are transfected into the somatic cell. Any method of transfection may be used, and may depend upon the type of donor cell undergoing transfection.

Cationic lipid transfection may be employed where cationic lipids facilitate DNA delivery into the donor cells. Alternatives to this method include the use of cationic peptides and their derivatives (e.g., polylysine, polyornithine), linear or branched synthetic polymers (e.g., polybrene, polyethyleneimine), polysaccharide-based delivery molecules (e.g., cyclodextrin, chitosan), natural polymers (e.g., histone, collagen), and activated and non-activated dendrimers.

Electroporation techniques creates temporary pores in cell membranes to allow DNA entry using an electrical field, or encourage the endocytosis of DNA. Nucleofection™ (Lonza) is an electroporation-based transfection method which enables transfer of nucleic acids such as DNA and RNA into cells by applying a specific voltage and reagents.

Calcium phosphate co-precipitation may be used for certain donor cells.

The transfected cells are then cultured using appropriate conditions to permit expression of the reprogramming factors from the closed linear DNA vectors. Conditions for permitting reprogramming are generally known in the art, and any appropriate conditions may be selected. Ideally, for human therapeutic use, the culturing may be performed in a feeder-free system, such that the cells obtained are free of any animal (xeno) contamination.

In the Examples, on day 0 Human dermal fibroblasts (hDFs) were nucleofected with closed linear DNA-based reprogramming factors (SOX2, OCT4, KLF4, L-Myc, LIN28) (FIG. 1) which are necessary to induce a state of pluripotency. The cells were then seeded onto a single 6-well in complete DMEM.

Subsequently, on day 1 the medium was refreshed before being changed continually every 2 days. Upon reaching a confluency of >90%, the hDFs were then passaged and seeded into a flask. On day 8, the re-programming hDFs were dissociated utilising cell dissociation enzymes before 60,000 of the cells were re-plated onto a flask containing feeder layer iMEFs. After 24 hours the cell medium was then exchanged from complete DMEM to hESC media which was replenished every 2 days.

Closed linear DNA is generally understood to be double-stranded DNA covalently closed at each end. The double stranded section of the DNA is therefore complementary. When denatured, closed linear DNA may form a single stranded circle. The DNA may be closed at each end by any suitable structure, including a cruciform, a hairpin or a hairpin loop, depending on preference. The end of the closed linear DNA may be composed of a non-complementary sequence, thus forcing the DNA into a single stranded configuration at the cruciform, hairpin or hairpin loop. Alternatively, the sequence can be complementary. It may be preferred that the end is formed by a portion of a target sequence for a protelomerase enzyme. A protelomerase target sequence is any DNA sequence whose presence in a DNA template allows for the enzymatic activity of protelomerase, which cuts a double stranded section of DNA and re-ligates them, leaving covalently closed ends. In general, a protelomerase target sequence comprises any perfect palindromic sequence i.e. any double-stranded DNA sequence having two-fold rotational symmetry, or a perfect inverted repeat. The closed linear DNA may have a portion of a protelomerase target sequence at one or both ends. The protelomerase target sequence can have the same cognate protelomerase at each end, or require a different protelomerase for each end. Closed linear DNA constructed via the action of various protelomerase enzymes have been previously disclosed by the applicants in WO2010/086626, WO2012/017210 and WO2016/132129, all of which are incorporated by reference. Closed linear DNA constructed using in vitro DNA amplification followed by cleavage with a protelomerase enzyme has the advantage that the closed linear DNA is produced in an in vitro, cell-free environment, and can be scaled up for commercial production. These closed linear DNA vectors are known as Doggybone DNA or dbDNA™. It is preferred that the closed linear DNA vectors are made using the prior methods of the applicants, in an in vitro, cell-free manner based upon polymerase based amplification of a DNA template with at least one protelomerase target sequence, and processing of the amplified DNA with a protelomerase to produce closed linear DNA.

Closed linear DNA can be constructed by a conversion of a plasmid with the requisite protelomerase target sequences into a closed linear DNA vector, although this is not an efficient method of production.

Other closed linear DNA vectors have been constructed by various in vitro strategies including the capping of PCR products, and the "minimalistic immunogenic defined gene expression (MIDGE)" vectors. MIDGE is generated by the digestion of both prokaryotic and eukaryotic backbones after isolation of plasmid from bacterial cells, followed by ligation of the required DNA sequence into hairpin sequences for end-refilling.

DNA "ministrings", which are produced in an in vivo manner in cell culture, based upon the action of protelomerase, are also closed linear DNA vectors that would be suitable for use in the invention.

Other forms of closed linear DNA that may be suitable include those closed at the ends with cruciform structures, which can again be manufactured in cell culture.

It may be preferred that the closed linear DNA is manufactured in a cell-free system, since this ensures purity of product, in the alternative, stringent purification of closed linear DNA made by cellular methods will be required by the regulatory authorities.

The present invention further relates to the cells made using the method of the invention, since the present inventors have found that these are more stable compared to those transfected using alternative episomal vectors, such as vectors including OriP/EBNA1 and/or sequences which knock-down p53.

The cells of the present invention have all the required characteristics of pluripotent stem cells, including but not limited to: the potential to differentiate into different types of specialised cells, the ability to go through numerous cycles of cell division while maintaining the undifferentiated state, the expression of pluripotency genes, the epigenetic patterns associated with embryonic stem cells, the ability to form embryoid bodies and teratoma, and the ability to form viable chimeras. These are discussed in more detail below.

Morphologically, it is expected that the iPSCs will have a round shape, large nucleolus and scant cytoplasm. Colonies of iPSCs are expected to form sharp-edged, flat, tightly packed colonies similar to hESCs.

Doubling time and mitotic activity are cornerstones of stem cell growth, since they must self-renew as part of their definition. iPSCs according to the invention are expected to be mitotically active, actively self-renewing and proliferating.

Alkaline phosphatase (AP) staining can be used for early identification of iPSCs before colonies emerge. Various stains may be employed on live cells enabling further culturing (such as AP Live from ThermoFisher) and repeated testing. AP is a generally applicable pluripotent marker for cells including ESCs, embryonic germ cells, and iPSC. The pluripotent status of stem cells can be characterised by indicative AP expression, optionally along with the expression of multiple pluripotency markers including one or more of the transcription factors Nanog, Oct4, Sox2, stage-specific embryonic antigens, and tumour related antigens, TRA-1-60, TRA-1-81.

Stem cell markers: iPSCs expressed cell surface antigenic markers expressed on ESCs. Human iPSCs expressed the markers specific to hESC, including SSEA-3, SSEA-4, TRA-1-60, TRA-1-81, TRA-2-49/6E, and NANOG. Human iPSCs may also lack markers that are associated with differentiation, such as SSEA-1.

Cell surface antigen expression can be assessed using immunofluorescence detected by flow cytofluorometry after harvesting cultures as single cell suspensions using trypsin-EDTA, as previously described (Andrews P W, et al In: Robertson E J, editor. Teratocarcinomas and Embryonic Stem Cells: a Practical Approach. Oxford: IRL Press; 1987a). Monoclonal antibodies can be used to detect surface antigen expression.

Figure 17:
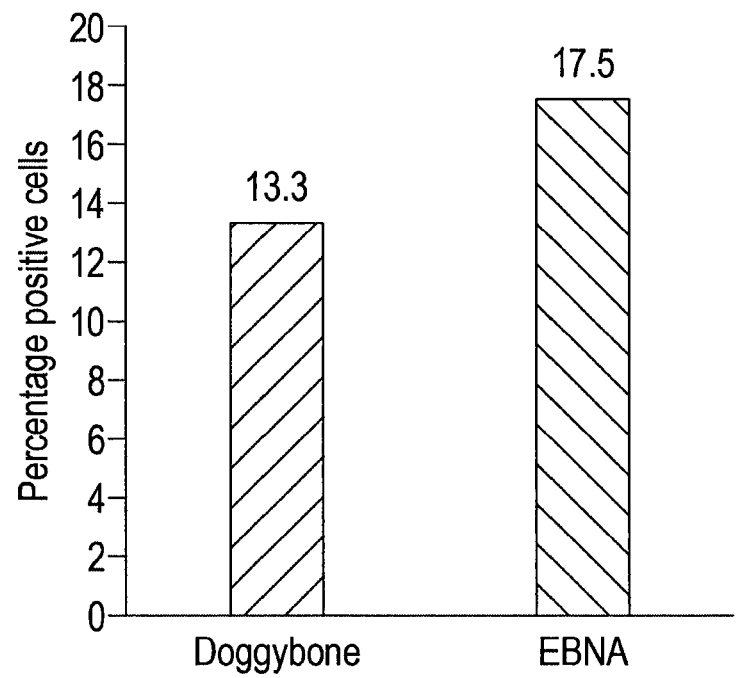
FIG. 17: Histogram showing percentage of SSEA1 expressing iPSC cells induced using either OriP/EBNA1 vectors or closed linear DNA with a FACS analysis threshold of 40 relative fluorescence units (RFU). A threshold of 40 relative fluorescence units were used to determine SSEA-1 positive cells, based upon the background staining presented in the isotype controls, the area under the histogram was calculated above and below these to determine the percentage. More SSEA1 positive cells were observed in OriP/EBNA1 induced cells than in those induced according to methods of the invention.
Figure 18A:
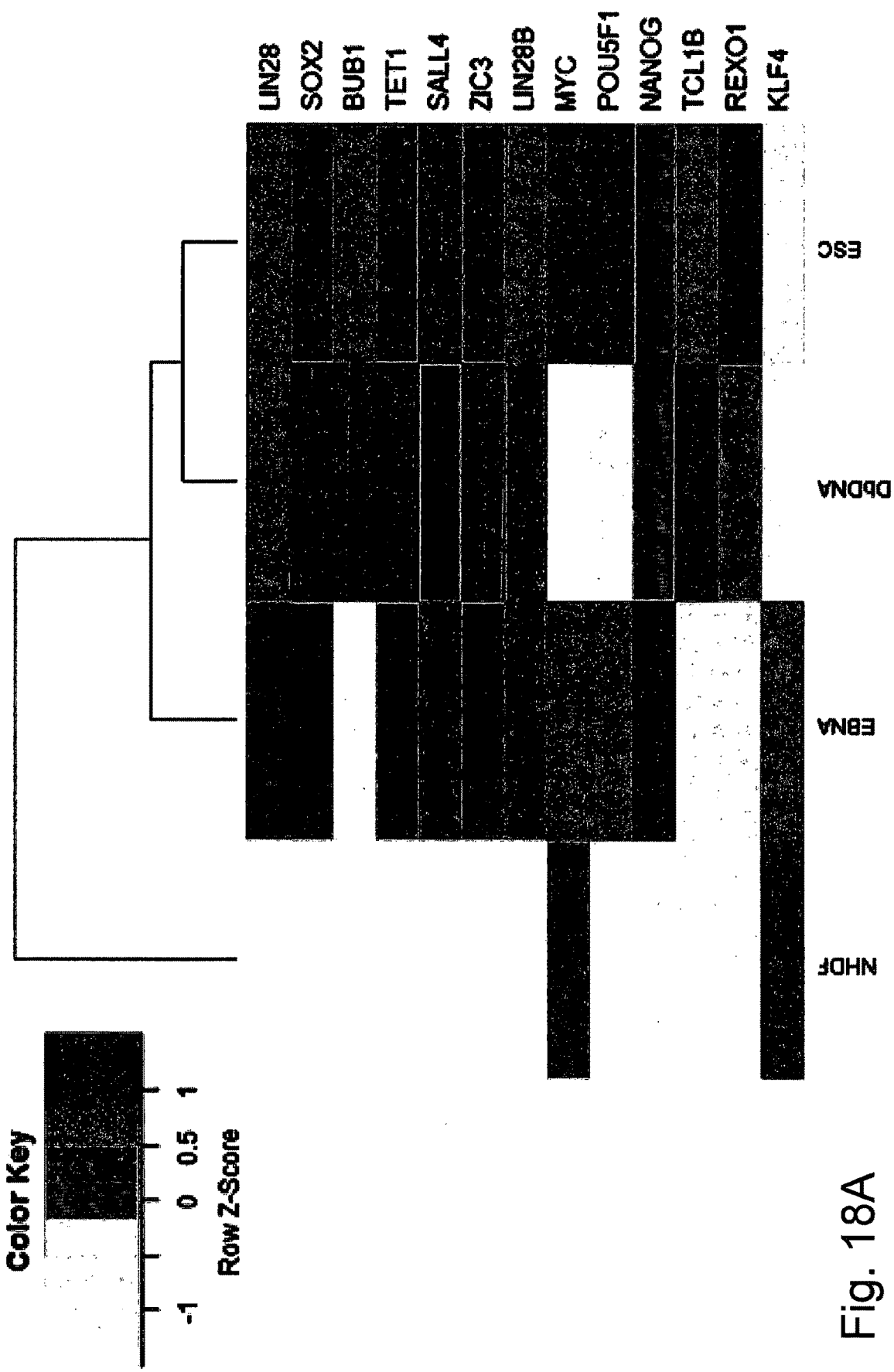
FIG. 18A: Monochromatic heatmap comparison of pluripotency associated transcripts in dbDNA (closed linear DNA) and OriP/EBNA1 vector generated iPSC. Human iPSC lines generated using dbDNA vectors or OriP/EBNA1 episomal plasmids and compared using RNA sequencing alongside the parental normal human dermal fibroblast cell line and the Shef3 human ESC line. Hierarchical clustering of pluripotency associated transcripts showed that the closed linear DNA generated iPSC were more similar to ESC than those generated using OriP/EBNA1.
Figure 18B:
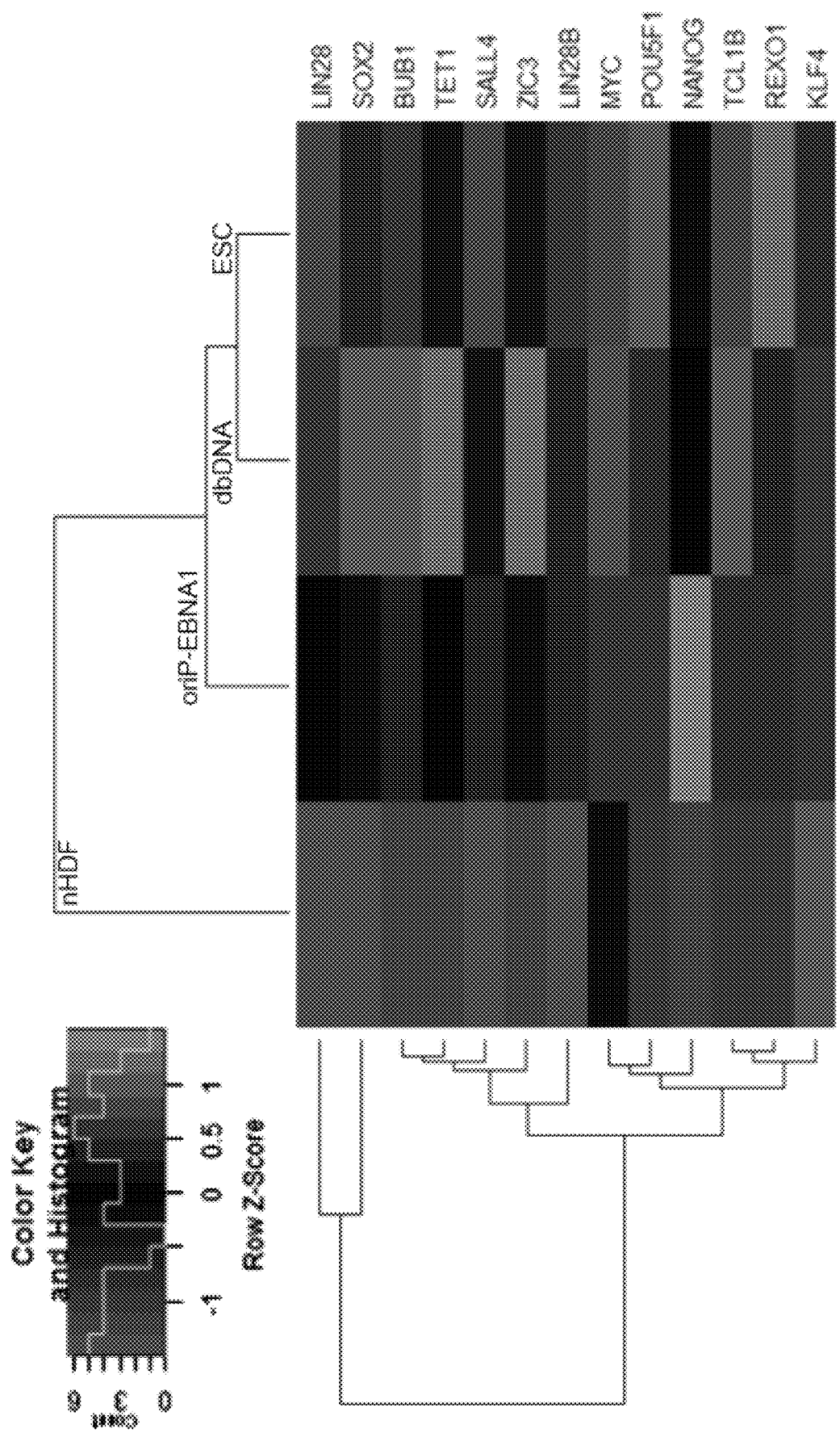
FIG. 18B is the same heatmap in colour.
Figure 19A:
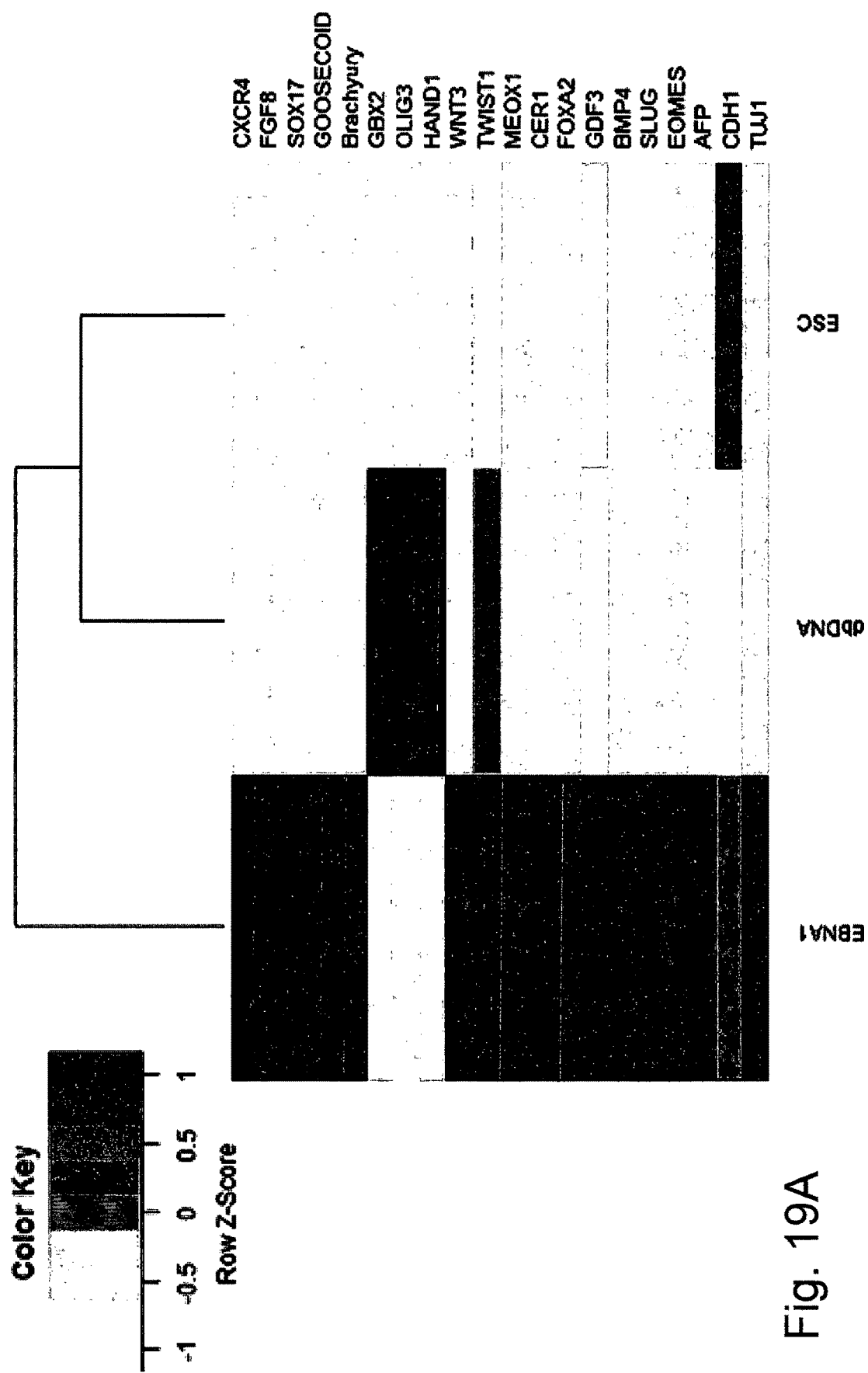
FIG. 19A: Monochromatic heatmap showing a comparison of transcripts associated with pluripotent stem cell differentiation between dbDNA (closed linear DNA) and OriP/EBNA1 vector generated iPSC. Human iPSC lines generated using dbDNA vectors or OriP/EBNA1 episomal plasmids and compared using RNA sequencing Shef3 human ESC line. Hierarchical clustering of transcripts associated with early differentiation showed that the closed linear DNA generated iPSC are more similar to ESC than those generated using OriP/EBNA1.
Figure 19B:
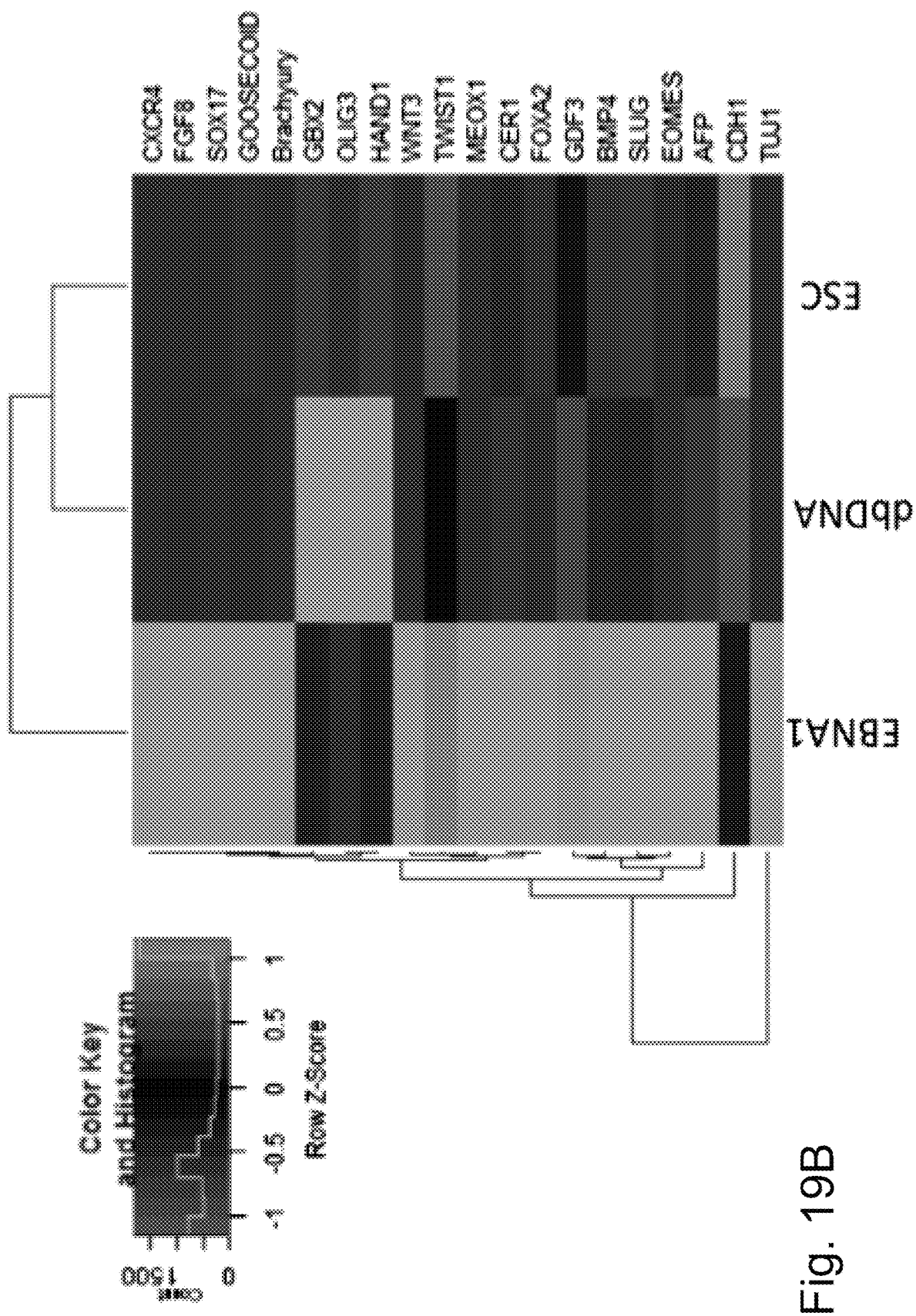
FIG. 19B is the same heatmap in colour.

In the Examples it can be seen that the iPSCs induced by the methods of the invention have lower levels of expression of Stage-Specific Embryonic Antigen-1 (SSEA-1) than cells induced using standard vectors (FIG. 17). SSEA-1 is a cell-surface carbohydrate epitope and is a marker of early differentiation, and is present at the very earliest stages of exit from the pluripotent state, whilst being absent from cells remaining pluripotent. Therefore, this is a very early marker that the cells are in the early stages of spontaneous differentiation, and low levels of expression of this marker in pluripotent cells is therefore desirable. Human embryonic stem cells do not express SSEA1 (Henderson J. K et al, Stem Cells, 20 (2002), pp. 329-337). Therefore, one indication that the iPSCs are stable in the pluripotent state is an absence of expression of SSEA-1 on the cell surface.

SSEA-3 is a cell-surface glycosphingolipid which is expressed on cells with in a pluripotent state, and expression is lost as the cells lose this pluripotent state and differentiate. Human embryonic stem cells express SSEA-3 on their surface (Henderson et al). Therefore, another indication that the iPSCs are stable in the pluripotent state is the presence of expression of SSEA-3 on the cell surface.

TRA-1-81 is a cell-surface carbohydrate which is expressed on cells with in a pluripotent state, and expression of this carbohydrate is lost as the cells lose this pluripotent state and differentiate. Human embryonic stem cells express the carbohydrate TRA-1-81 on their surface. Therefore, another indication that the iPSCs are stable in the pluripotent state is the presence of expression of carbohydrate TRA-1-81 on the cell surface. TRA-1-81 is downregulated during differentiation.

Many stem cell markers, such as SSEA-3, SSEA-4, TRA-1-60 and TRA-1-81 are carbohydrate epitopes. Stem cells therefore may display a characteristic glycosylation profile that distinguishes them from differentiated cell types. Therefore, the stable cells can be indicated by the glycosylation profile at the cell surface, which may be similar to the pattern seen on human embryonic stem cells.

iPSCs may express the following genes, also expressed in undifferentiated ESCs, including Oct-3/4, Sox2, NANOG, GDF3, REX1, FGF4, ESG1, DPPA2, DPPA4, and hTERT. The list may further include gene expression of H3K4me3 and H3K27me3.

iPSCs may also demonstrate high telomerase activity and express hTERT (human telomerase reverse transcriptase), a necessary component in the telomerase protein complex.

iPSCs may also be capable of neural differentiation and cardiac differentiation. Further, they are capable of teratoma formation; if injected into immunodeficient mice. Teratomas are tumours of multiple lineages containing tissue derived from the three germ layers endoderm, mesoderm and ectoderm. The stem cells may also be capable of embryoid body formation; in culture spontaneously form ball-like embryo-like structures termed "embryoid bodies", which consist of a core of mitotically active and differentiating stem cells and a periphery of fully differentiated cells from all three germ layers. Further, the ability to form chimeras is an indication of iPSCs; this can be tested by injecting the cells into a trophoblast of a blastocyst and transferred to a recipient female animal (mouse) and testing the chimerism of the resulting offspring.

Epigenetic reprogramming in iPSCs that may be monitored includes demethylation of CpG sites in promoters, such as those for the pluripotency-associated genes, including Oct-3/4, Rex1, and NANOG. More globally, DNA methylation patterns can be altered, including histone demethylation.

By using any one or more of the above characteristics, it is possible to determine that a cell is an iPSC according to the present invention.

By "stable" it is meant that the induce pluripotent stem cells generated according to the methods and uses of the present invention, when compared to cells made using other the same reprogramming factors expressed from OriP/EBNA1 vectors the cells have a reduced capacity for spontaneous differentiation whilst the cells are being cultured under conditions appropriate to maintain pluripotency, these conditions including but not limited to passaging in the relevant culture media, which may be termed "pluripotency media". Alternatively put, it means that the pluripotent stem cells can be cultured for at least 28 days without a significant proportion of cells (5% or more) spontaneously differentiating. The cells would be cultured for at least 25 to 60 days, optionally 28 to 50 days, further optionally 30 to 40 days, even further for at least 35 days. The proportion of cells that maintain pluripotency during these periods are 100%, 99%, 98%, 97%, 96%, 95%, 94%, 93%, 92%, 91% or 90% or more. Therefore, at least 1%, 2%, 3%, 4%, 5%, 6%, 7%, 8%, 9% or more may have undergone spontaneous differentiation.

Stable cells may be classified as grade A, as discussed previously.

Stable cells may also be described as cells with genomic stability and integrity. Genomic stability may be quantified by looking at the genomic (including at karyotypic and subkaryotypic levels) and epigenomic abnormalities of the cells in long term culture. Varieties of methods may be applied in order to establish genomic and epigenomic stability, including karyotyping (including G-banded karyotyping), fluorescent in situ hybridisation (FISH), Spectral Karyotyping (SKY), array based comparative genomic hybridisation to detect copy number variations (CNVs), single nucleotide polymorphism (SNP) based microarrays, again to detect CNVs and also loss of heterozygosity, analysis of genomic integration sites, global gene expression meta-analysis, and most comprehensively, whole genome sequencing. Of these, G-banded karyotyping can provide a snapshot of the entire genome and can be particularly useful, detecting gross abnormalities quickly, but is limited to large abnormalities. A blend of several techniques may therefore be required.

Optionally, the cells of the present invention may be described as stable if they lack the common changes seen in the genome of long term cultured pluripotent cells. Such recurrent changes include trisomy or amplification of 12p, trisomy X, trisomy 17, amplification of 17q, amplification of 20q11.21, isodicentric X, deletion of 18q12.1, amplification of 1p36.13, amplification of 1p36.33, amplification of 2p11.2, amplification of 7q35, amplification of 14q32.32, deletion of 15q11.2, amplification of 21q11.2, amplification of 21q11.22, deletion of 22q11.21, trisomy 8, trisomy 20q, amplification 1q31.3, deletion of 17q21.1 and deletion of 8q24.3. These can be assessed by the methods outlined above. It is preferred that the cells of the invention are lacking all of these abnormalities. Of these, trisomy or amplification of 12p, trisomy X, amplification of 17q, amplification of 17q, amplification of 20q11.21, trisomy 8, trisomy 20q, amplification 1q31.3, deletion of 17q21.1 and deletion of 8q24.3 are most commonly seen in human iPSC cultures. Optionally, the stable cells lack all of these abnormalities.

It will be understood that certain genomic/epigenomic abnormalities would have the potential to cause tumourigenesis, so it is desirable to produce cells that are genomically stable.

Further, the cells obtained by the methods of the invention were subjected in the Examples to further assays, based upon the levels of various RNA sequences in these cells, their transcriptome. RNA sequencing based assays (RNA-seq) produce heatmaps enabling the visualisation of molecular profiling data. Analysing the RNA within a cell has the advantage that this allows detection of the genes that are being expressed, together with relative expression levels. The set of RNA molecule in a cell or population of cells can be analysed this way. Total RNA can be isolated from the cell/population, reverse transcribed to DNA if the analysis method requires this step, and sequenced, preferably in a high-throughput method. Many methods are available, and can use systems such as microfluidic platforms (i.e. Fluidgm Cl) or microtitre plate platforms (i.e. Smart-Seq 2).

Alternatively, microarray chips or the like including immobilised labelled probes or capture agents for specific RNA sequences can be utilised. The binding of particular RNA sequences can be detected and this also allows a heat map of the RNA sequences present in the cell/population to be drawn up, as the amount of each sequence detected can be determined. The signal intensity from the array will be directly proportional to the level of RNA.

RNA sequencing heat maps determined by such methods have established that for the cells made according to the methods of the invention, the levels of RNA expression associated with differentiation of stem cells are low, and indeed are lower than comparable cells induced using current techniques. This indicates that the cells of the present invention are more stable than those induced using OriP/EBNA1 vectors, since the level of expression of RNA associated with differentiation are lower than the cells induced with OriP/EBNA1 vectors, and are comparable to the expression levels in naturally derived stem cells.

FIGS. 18A-18B and 19A-19B are RNA sequence maps obtained when cells are interrogated as to their expression levels. Example 9 described the experiments conducted.

The inventors have studied various RNA sequences within the iPSC, compared to embryonic stem cells. In the Examples, various RNA sequences are investigated, and groups of RNA sequences known to be associated with various phenotypes/conditions/states were examined. Notably, RNA sequences associated with interferon signalling were examined. Looking at this set of RNA sequences, it is clear that the cells induced according to the methods of the invention are closer with respect to the levels of these RNA sequences to ESC than to cells induced with OriP/EBNA1 vectors (see FIG. 18A or 18B). The interferon (IFN) pathway plays a critical role in the human immune response, and from these results it is possible to see that in cells induced using methods of the invention, that the levels of interferon signalling in these cells are reduced compared to the EBNA1 vector-induced iPSC. It has been found that factors required to maintain pluripotency are incompatible with those involved in eliciting IFN-based responses (Type I interferon response impairs differentiation potential of pluripotent stem cells, Julie Eggenberger et al, PNAS Jan. 22, 2019 116 (4) 1384-1393.) Therefore, in iPSC, expression of IFN pathway genes is undesirable where pluripotency is to be maintained. Interferon signalling RNA sequences investigated in the Examples (see FIGS. 20A and 20B, Example 9) includes STAT1, IRAK1, EIF2AK2, STAT2, IRF9, IRF7, ISG20, IFIT1, MyD88, IFI27, TNFSF10, MX1, ISG15 and NFKBIA. Analysis of all or some of the levels of these RNA sequences within a cell or population of cells can give an important indicator as to the stability of the iPSC, since high levels of RNA for these markers would indicate that the pluripotency may not be maintained.

Indeed, the Examples show that STAT1 is massively upregulated in cells transduced by standard vectors, whereas cells transduced according to the present invention lack this upregulation. STAT1 (Signal transducer and activator of transcription 1) is a transcription factor and a major regulator of inteferons.

Further, RNA sequences associated with differentiation were examined, these included CXCR4, FGF8, SOX17, GOOSECOID, Brachyury, GBX2, OLIG3, HAND1, WNT3, TWIST1, MEOX1, CER1, FOXA2, GDF3, BMP4, SLUG, EOMES, AFP, CDH1 and TUJ1. It was found (see FIGS. 19A and 19B, Example 9) that the levels of RNA in cells induced according to the present invention were more closely related to the natural levels seen in ESC than to the levels seen in iPSCs induced using OriP/EBNA1 vectors. Analysis of all or some of the levels of these RNA sequences within a cell or population of cells can give an important indicator as to the stability of the iPSC, since high levels of RNA for these markers would indicate that the cell is likely to start to differentiate, or has already done so.

Similarly, pluripotency markers were examined using RNA Seq. These markers included LIN28, SOX2, BUB1 TET1, SALL4, ZIC3, LIN28B, MYC, POU5F1, NANOG, TCL1B, REXO1 and KLF4. It was found (see FIGS. 18A and 18B, Example 9) that the levels of RNA in cells induced according to the present invention were more closely related to the natural levels seen in ESC than to the levels seen in iPSCs induced using OriP/EBNA1 vector, and indeed in the differentiated cells from which both sets of iPSC were derived. Analysis of all or some of the levels of these RNA sequences within a cell or population of cells can give an important indicator as to the stability of the iPSC, since lower levels of RNA for these pluripotency markers would indicate that the cell is likely to start to differentiate, or has already done so.

CDKN1A-mediated inhibition of proliferation is a further indicator of differentiation of pluripotent stem cells.

Induced pluripotent stem cells that are stable are classified as grade A, based upon morphological appearance. The grading of stem cells is discussed previously. Stable iPSCs have a classification similar to ESCs.

Induced pluripotent stem cells that are stable are closer in phenotype to embryonic stem cells than cells reprogrammed using OriP/EBNA1 vectors. The data presented here supports this assertion.

In the context of induced pluripotent stem cells, stable can therefore be defined as any one or more of the following phenotypes:
  (a) Reduced levels of spontaneous differentiation in culture;
  (b) a low expression of SSEA1 on the cell surface;
  (c) expression of cell surface antigens associated with a pluripotent state (such as SSEA3, TRA-1-81 and/or Tra-1-60);
  (d) Low levels or negligible levels of RNA sequences associated with differentiation (for example, any one, two, three or more of CXCR4, FGF8, SOX17, GOOSECOID, Brachyury, GBX2, OLIG3, HAND1, WNT3, TWIST1, MEOX1, CER1, FOXA2, GDF3, BMP4, SLUG, EOMES, AFP, CDH1 and/or TUJ1);
  (e) low levels or negligible levels of RNA sequences associated with interferon signalling (for example, any one, two, three or more of STAT1, IRAK1, EIF2AK2, STAT2, IRF9, IRF7, ISG20, IFIT1, MyD88, IFI27, TNFSF10, MX1, ISG15 and/or NFKBIA); and/or (f) presence of RNA sequences associated with pluripotency (for example, any one, two, three or more of LIN28, SOX2, BUB1 TET1, SALL4, ZIC3, LIN28B, MYC, POU5F1, NANOG, TCL1B, REXO1 and/or KLF4)

Negligible indicates an amount too small or insignificant to be of importance.

The invention therefore further relates to a population of induced pluripotent stem cells, wherein said population of cells is made using any use or method as described here. Thus, the cells are generated by use of a transfected closed linear DNA expressing one or more reprogramming factor as herein described. The cells are preferably homogeneous and undifferentiated. It is preferred that less than 10% of the cells in the population or colony of cells have differentiated, preferably, less than 9, 8, 7, 6, 5, 4, 3, 2, or 1% of cells have re-differentiated.

Said population of cells may no longer harbour the closed linear DNA vectors, since these are naturally lost during cell maintenance, making these much safer than cells induced by current methods, including retroviral methods where the reprogramming factors are not removed. It is preferred that the cells are lacking the closed linear DNA vector used in their induction, since the expression of the reprogramming factors is no longer required. This is beneficial, since some reprogramming factors may be oncogenes, as discussed previously, and the loss of the DNA vector is desirable as extraneous sequences to the cell have been lost.

Figure 14A:
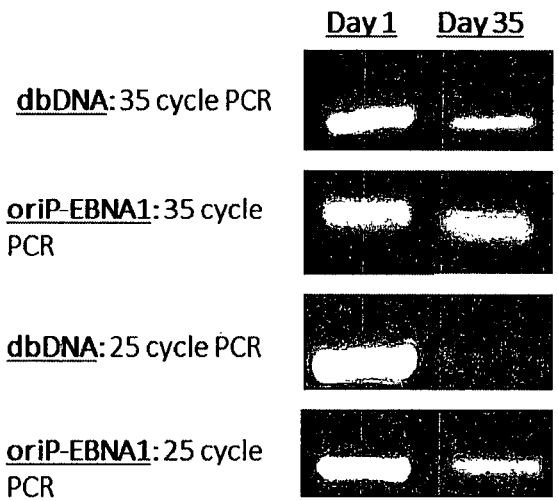
FIG. 14A shows the results from the experiments to demonstrate vector retention. This is a photograph of PCR amplicons subjected to agarose gel electrophoresis depicting the retention of both closed linear DNA (dbDNA) and OriP/EBNA1 vector in the transfected cells. Results are shown for either 25 or 35 cycles of PCR. The OriP/EBNA1 episomal vector is retained in greater quantity than the closed linear DNA vector.
Figure 14B:
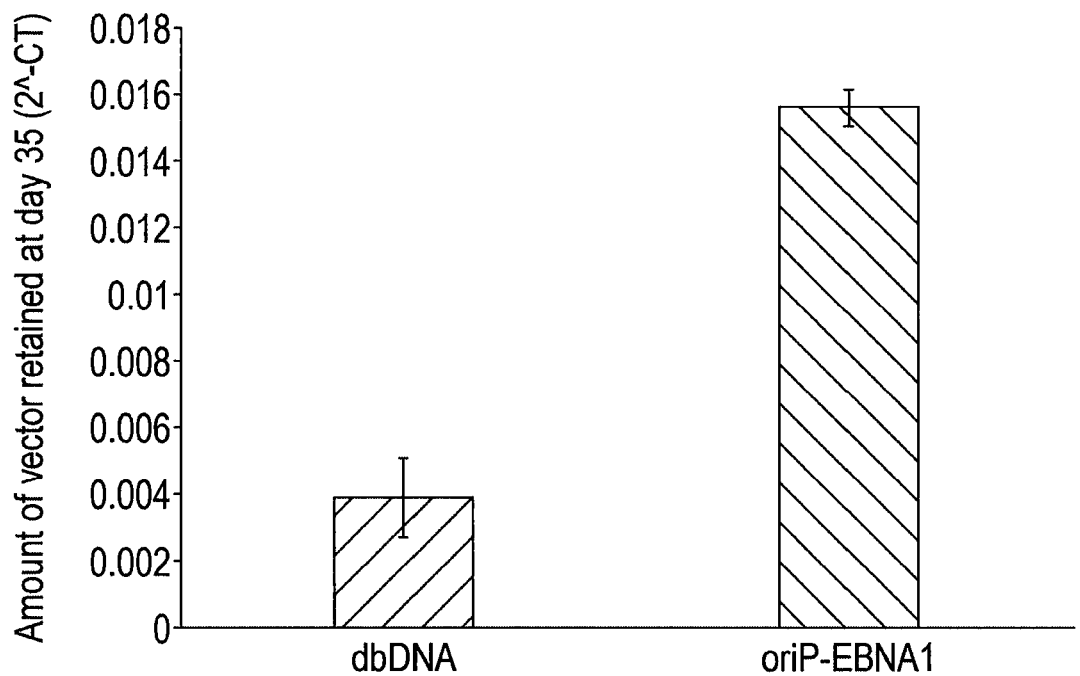
FIG. 14B shows the results from the experiments to demonstrate vector retention. The amount of closed linear DNA vector or episomal plasmid vector (OriP/EBNA1) at 35 days is compared. Again, the episomal plasmid is retained at higher quantities than the closed linear DNA.
Figure 15:
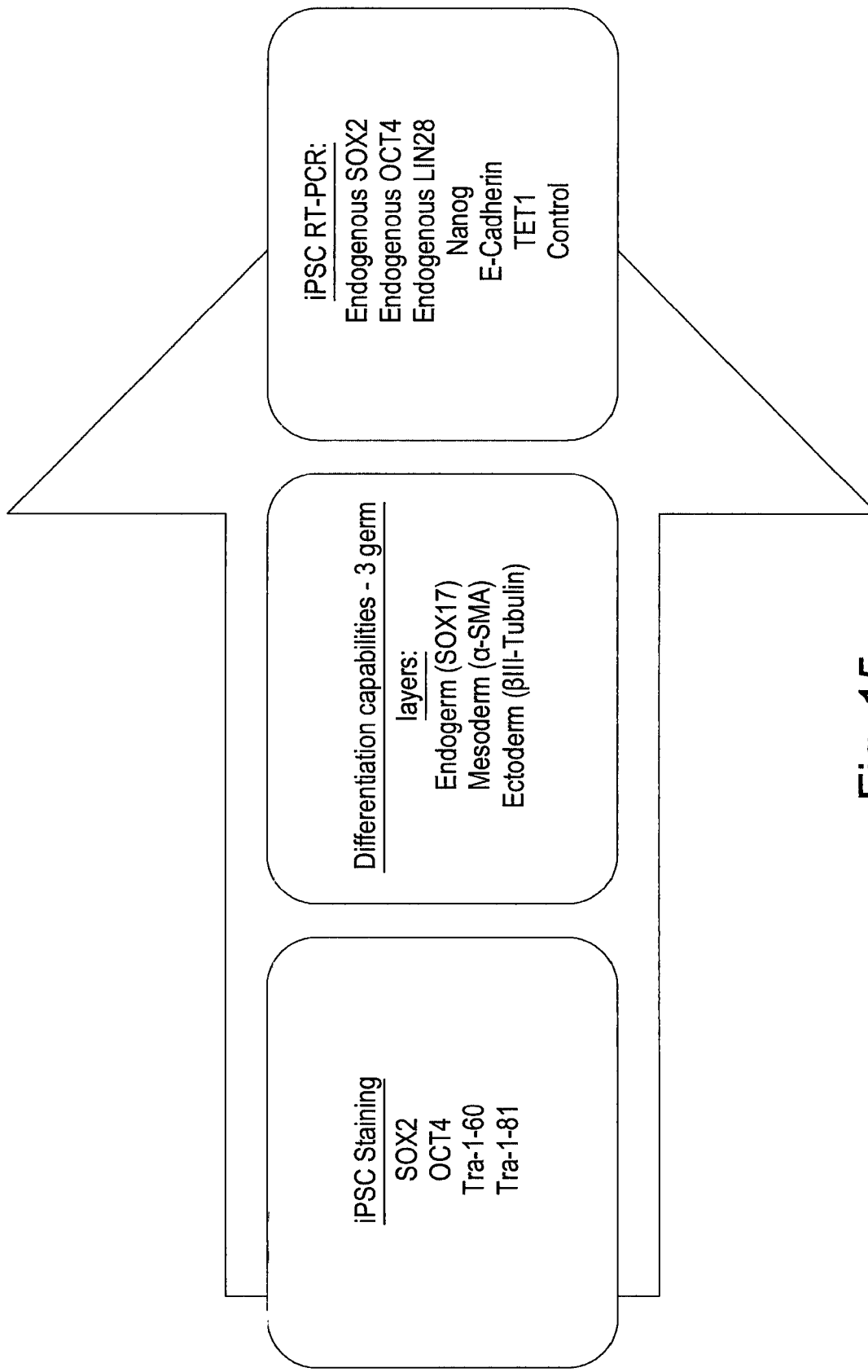
FIG. 15 is a diagram that depicts the characteristics of iPSC populations, to show characteristics that can be used to determine if a cell is a pluripotent stem cell.

Said invention therefore includes a therapeutic grade population of stable, pluripotent stem cells induced with a closed linear DNA vector encoding at least one reprogramming factor. The cells are at least 90%-100% free of the closed linear DNA vector, optionally 90, 91, 92, 93, 94, 95, 96, 97, 98 or 99% free of the closed linear DNA vector. This can be tested using PCR amplification looking for sequences which are unique to the closed linear DNA vector. For example, if the CAG promoter module is used, this is an appropriate target for amplification due to its unique sequence. FIGS. 14A and 14B demonstrate the process of the loss of the vector from the cell.

Alternatively, the stable, pluripotent stem cells may be described as of a Good Manufacturing Practice (GMP) grade, suitable for therapeutic use due to the lack of closed linear DNA vector. Alternatively, the cells may be described as "clinical grade".

The cells of the invention may be provided as a cell culture, preferably a feeder-layer free culture.

The cells of the invention are preferably animal cells, most preferably human cells.

The present invention therefore includes a population of stable pluripotent stem cells induced with a closed linear DNA vector, in particular a population of stable pluripotent stem cells induced with a closed linear DNA vector which does not contain OriP/EBNA1. The closed linear DNA vector and methods used to generate the claims of the invention has been described extensively previously, and these also apply here.

The cells of the invention preferably lack the closed linear DNA vector(s).

As described previously, the cells generated through use of the closed linear DNA of the present invention have been found to be more stable when compared to the cells generated using OriP/EBNA1 vectors.

The cells may be seen to be closer in phenotype to naturally occurring stem cells than cells induced using OriP/EBNA1 vectors. This phenotype is investigated extensively in the Examples presented here, but includes:

(i) markers for differentiation (i.e. SSEA1);
(ii) markers for pluripotency;
(iii) immune system gene expression;
(iv) cytokine signalling;
(v) interferon signalling; and/or
(vi) inflammatory response.

The phenotype may be established using an analysis of gene expression, which may be followed by analysis and hierarchical clustering. Experiments extensively show here that pluripotent stem cells induced by the methods of the invention cluster closer to natural human stem cells than they do to other induced pluripotent stem cell types.

Since the methods and uses of the invention result in a more stable iPSC population and are therefore more likely to be able to be used therapeutically, the use of a closed linear DNA vector to obtain these cells is also new. The invention therefore further relates to a composition for preparing therapeutically acceptable induced pluripotent stem cell comprising a closed linear DNA vector encoding at least one reprogramming factor. The composition may be in any acceptable format and include any suitable excipients. It may further include agents that assist with the transfection procedure, such as transfection reagents.

The invention further includes a pharmaceutical composition comprising a closed linear DNA vector encoding at least one reprogramming factor and at least one pharmaceutically acceptable excipient. The cells of the invention can ultimately be used in a human therapeutic setting, and it is important that the production method of these cells complies with GMP. Therefore, a pharmaceutical composition of closed linear DNA vectors may be required, wherein the pharmaceutically suitable excipient includes agents that may stabilise the closed linear DNA, assist with transfection or be beneficial to the preparation of the cells.

Once pluripotency has been achieved, the cells of the invention may be therapeutically used as pluripotent cells or can be modified for purposes of gene therapy and the like. The cells may be differentiated into multipotent adult stem cells or terminally differentiated into specific cell types, by altering the conditions in which the cells are being cultured. There are many methods known in the art for differentiating the iPSC into cells of the desired type.

The cells of the invention, including cells derived from the iPSC can be transplanted into the body of the recipient by any suitable means, including transdermally, subcutaneously, intramuscularly, parentally, enterally, intravenously, intraperitoneally, intraorbitally, intraretinally, by transplantation of tissue and into cerebrospinal fluid.

The cells of the invention, including cells derived from the iPSC can be administered in a pharmaceutically acceptable medium. They may be provided as is, or in conjunction with a suitable medium or substrate, for example to support their growth.

The cells of the invention, including cells derived from the iPSC can be used in therapy.

Some markers for stem cells in general and early differentiation:

Pluripotent Stem Cells

Alkaline phosphatase: Elevated expression of this enzyme is associated with undifferentiated pluripotent stem cell (PSC)

Alpha-fetoprotein (AFP): Endoderm. Protein expressed during development of primitive endoderm; reflects endodermal differentiation Pluripotent Stem Cells.

Bone morphogenetic protein-4: Mesoderm. Growth and differentiation factor expressed during early mesoderm formation and differentiation.

Brachyury: Mesoderm. Transcription factor important in the earliest phases of mesoderm formation and differentiation; used as the earliest indicator of mesoderm formation.

Cluster designation 30 (CD30) Surface receptor molecule found specifically on PSC.

Cripto (TDGF-1) cardiomyocyte. Gene for growth factor expressed by ES cells, primitive ectoderm, and developing cardiomyocyte.

GATA-4 gene: Endoderm. Expression increases as ES differentiates into endoderm.

GCTM-2 ES: Antibody to a specific extracellular-matrix molecule that is synthesized by undifferentiated PSCs Genesis: Transcription factor uniquely expressed by ES cells either in or during the undifferentiated state of PSCs Germ cell nuclear factor: Transcription factor expressed by PSCs.

Hepatocyte nuclear factor-4 (HNF-4): Endoderm. Transcription factor expressed early in endoderm formation.

Nestin: Ectoderm, neural and pancreatic progenitor. Intermediate filaments within cells; characteristic of primitive neuroectoderm formation.

Neuronal cell-adhesion molecule (N-CAM): Ectoderm. Cell-surface molecule that promotes cell-cell interaction; indicates primitive neuroectoderm formation.

OCT4/POU5F1: Transcription factor unique to PSCs; essential for establishment and maintenance of undifferentiated PSCs.

Pax6: Ectoderm Transcription factor expressed as ES cell differentiates into neuroepithelium Stage-specific embryonic antigen-3 (SSEA-3): Glycoprotein specifically expressed in early embryonic development and by undifferentiated PSCs Stage-specific embryonic antigen-4 (SSEA-4: Glycoprotein specifically expressed in early embryonic development and by undifferentiated PSCs.

Stem cell factor (SCF or c-Kit ligand): Membrane protein that enhances proliferation of ES and EC cells, hematopoietic stem cell (HSCs), and mesenchymal stem cells (MSCs); binds the receptor c-Kit.

Telomerase: An enzyme uniquely associated with immortal cell lines; useful for identifying undifferentiated PSCs.

TRA-1-60: Antibody to a specific extracellular matrix molecule is synthesised by undifferentiated PSCs.

TRA-1-81: Antibody to a specific extracellular matrix molecule normally synthesised by undifferentiated PSCs.

Vimentin: Ectoderm, neural and pancreatic progenitor. Intermediate filaments within cells; characteristic of primitive neuroectoderm formation.

GenBank Accession Numbers for Sequences:
  Genomic Sequence of EBNA1: NC_007605.1.
  Genomic sequence of OriP: AJ012167.1
  Oct 3/4: Z11898.1 and NM_002701.5
  Gene sequence of Sox2: KU342033.1
  Gene sequence of Sox1: Y13436.1
  Gene sequence of Sox3: X71135.1
  mRNA sequence of Sox15: NM_006942.1
  mRNA sequence of klf1: NM_006563.4
  mRNA sequence of transcript variant 1 klf4: NM_001314052.1, variant 2 mRNA klf4:
    NM_004235.5, short isoform klf4 CDS: HM026463.1.
  mRNA sequence of klf5: AF287272.1; variant 2 klf5 mRNA: NM_001286818.1; variant 1 mRNA klf5: NM_001730.4; isoform D klf5 CDS: HQ628641.1; isoform B klf5 CDS: HQ628639.1.
  Gene sequence of c-Myc: AH002906; mRNA sequence of c-Myc: AH004538.1.
  Gene sequence of L-Myc: M19720.1; exons 1-2 of L-Myc: X07262.1
  Gene sequence of N-Myc: Y00664.1; exons 2&3 of N-Myc: M13241.1.
  Gene sequence of NANOG: JX105036.1
  Gene sequence of LIN28A homolog: NM_024674.5 and gene sequence of LIN28B homolog: NM_001004317.3.

GenBank Accession numbers LQ432011.1, LQ432012.1, LQ432013.1, LQ432014.1, LQ432015.1, LQ432016.1, LQ432017.1 and LQ432018.1 describe particular protelomerase target sequences that may be used in the closed linear DNA of the present invention.

The invention will now be described with reference to the following non-limiting examples.

EXAMPLES

Materials and Methods

TABLE 1

Cell Culture: Cell culture reagents

| Reagent | Company |
| --- | --- |
| DMEM | Sigma |
| MEM Non-essential amino acids | Life Technologies |
| Foetal Bovine serum | Gibco, Life Technologies |
| L-Glutamine | Sigma |
| Penicillin/Streptomycin | Sigma |
| Dulbecco's Phosphate buffered saline | Sigma |
| DMEM/F12 | Gibco, Life Technologies |
| KnockOUT ™ serum replacement | Gibco, Life Technologies |
| β-mercaptoethanol | Life Technologies |
| Mitomycin C | Sigma Aldrich |
| TrypLE ® express enzyme | Gibco, Life Technologies |
| FGF2 | R&D Systems |
| Laminin | Millipore |
| Gelatin from porcine skin | Sigma |
| Rock Inhibitor (Y-27632) | Sigma |
| Dimethyl sulfoxide | Sigma |
| N2 supplement | Life Technologies |
| B27 supplement | Life Technologies |
| Heparin | Sigma |
| Matrigel ® (extracellular matrix) | BD Bioscience |
| mTeSR ™ 1 | Stemcell Technologies |
| Rock inhibitor (Y-27632) | Sigma |
| Polyethylenimine | Sigma |
| OptiMEM ® (reduced serum medium) | Gibco, Life Technologies |

Medium and Constituents:

TABLE 2

Complete DMEM:

| Component | Volume |
| --- | --- |
| DMEM | 435 mL |
| FBS | 50 mL |
| L-Glutamine (200 mM) | 10 mL (4 mM) |
| PenStrep (100×) | 5 mL (1×) |

TABLE 3

Human embryonic stem cell (hESC) medium:

| Component | Volume |
|---|---|
| DMEM/F12 (1:1) | 38.5 mL |
| Non-essential amino acids (NEAA) | 0.5 mL (1×) |
| Knockout serum replacement (KSR) | 10 mL (20%) |
| bFGF (100 ug/mL) | 5 uL (10 ng/mL) |
| PenStrep (100×) | 0.5 mL (1×) |

Control neonatal dermal fibroblasts (nhDF) were purchased from Fisher Scientific (C0045C). Human dermal fibroblasts obtained from patients with Batten disease (BD) caused by mutations in CLN3, CLN6 and CLN7 genes were obtained from Prof. Sara Mole from the Laboratory for Molecular Cell Biology at UCL. Shef3 Human Embryonic stem cells (hESCs) were procured from the UK stem cell bank (SCSC10-48). Finally, MEF feeder cells were purchased from Cambridge Bioscience (CBA-310).

Isolation and Cultivation of Human Urine-Derived Cells:

The present work was performed after an approval was obtained from Ethics Committee and human urine samples collected with informed consent. To isolate cells, urine collection was made into sterile containers.

Cells were isolated and prepared for reprogramming according to the methods described in: Zhou et al, Nature Protocols volume 7, pages 2080-2089 (2012), which presents an alternative method for generating iSPCs from cells isolated from urine using standard reprogramming methods. Once prepared for reprogramming, the cells were reprogrammed by transfected with the vectors described here using the methods described herein.

Isolation and cultivation of blood cells including monocytes from peripheral blood samples:

The present work was performed after an approval was obtained from Ethics Committee and human blood samples collected with informed consent. Monocytes are contained in the peripheral blood at a proportion of around 3%-8%.

Cells were isolated and prepared for reprogramming according to the methods described in: Isogai et al, Cell Reprogram. 2018 Dec. 1; 20 (6): 347-355, prior to reprogramming using the method of the invention.

Cell Culture Methodologies:

The culturing and inactivation of Mouse embryonic fibroblasts (MEFs);

Upon defrosting, MEFs were cultured in complete DMEM supplemented with 1× (v/v) non-essential amino acids. The cell medium was routinely replaced every other day and upon reaching a confluency of 90-95% the cells were then passaged. MEFs were split in a 1:4 ratio, firstly being trypsinised utilising 150 µL/cm$^2$ of TrypLER to dissociate the cells before being collected and centrifuged at 258 g for 5 minutes. The cell pellet was furthermore re-suspended in an adequate volume of culturing media prior to re-plating.

After amplification to passage 4 (P4), the MEFs were then mitotically inactivated following an incubation with Mitomycin C (0.1 µg/uL) in complete DMEM at 37° C. for 3 hours. Post-incubation, the MEFs then went through 4 wash steps in 10 ml of Dulbeccos Phosphate Buffered Saline (DPBS) before again being enzymatically detached utilising 150 µL/cm$^2$ of TrypLE®. Once >90% of the cells had dis-associated from the flask surface, these were then stored at −80° C. in FBS supplemented with 10% (v/v) Dimethyl Sulfoxide (DMSO) at a density of ~5×10$^6$ cells/mL. Moreover, prior to the culture of pluripotent stem cells (PSCs)-MEFs were seeded at a density of 5×10$^4$ cells/cm$^2$ on culture dishes/flasks that were pre-coated in 0.1% (w/v) gelatin.

For transient transfection, cells were cultured to a confluency of >90%. A set volume of PEI was firstly re-suspended in Opti-MEM®, prior to a set concentration of DNA being separately re-suspended in Opti-MEM®. The PEI/DNA aliquots were then combined in order to potentiate PEI-DNA complex formation. Subsequent to a 20 minute room temperature incubation period, the PEI-DNA complexes were transferred onto the well of HEK293T cells. A 2-3 hour incubation at 37° C. was then undertaken. Post-incubation, the Opti-MEM® and any remaining PEI/DNA was removed from the well and 2 mL complete DMEM added.

PEI preparation: Opti-MEM® Volume 327.25 µL, PEI Volume 2.75 µL.

DNA Preparation: Opti-MEM® Volume 327.25 µL, DNA Concentration 2.75 µg

Human Dermal Fibroblast (hDF) Culturing and Maintenance:

hDFs were cultured in complete DMEM with regular media changes every other day. The cells were routinely passaged, being enzymatically dissociated utilising TrypLE® before being centrifuged at 258 g for 5 minutes. The cells were then seeded at a density of ~3×10$^4$ cm$^2$.

Culturing and Passaging of Pluripotent Stem Cells (PSCs):

hESCs and iPSCs (PSCs) were cultured on a MEF feeder layer (iMEF) in hESC media-which was routinely refreshed every other day. PSC colonies were passaged regularly-every 4-10 days dependant on colony morphology. Prior to passaging, fresh hESC media was placed onto the cells. PSC colonies were then manually excised from the flask into the fresh media. The colonies were then further dissociated by being passed through a pipette before being placed onto fresh iMEFs.

Somatic Cell Reprogramming & Production of iPSCs:

The methodology for reprogramming HDFs is presented here, and similar methodologies were used for the other somatic cell types collected and reprogrammed by the inventors.

HDFs were nucleofected utilising the Amaxa® Nucleofector® transfection 2b device. This would supply the cells with episomal plasmid-based or closed linear DNA-based reprogramming factors (SOX2, OCT4, KLF4, I-Myc, shp53) which were necessary to induce a state of pluripotency. Furthermore, for an improved efficiency, additional EBNA1 expression plasmid was also added where the plasmid system was utilised.

TABLE 4 reprogramming vectors

Figure 1:
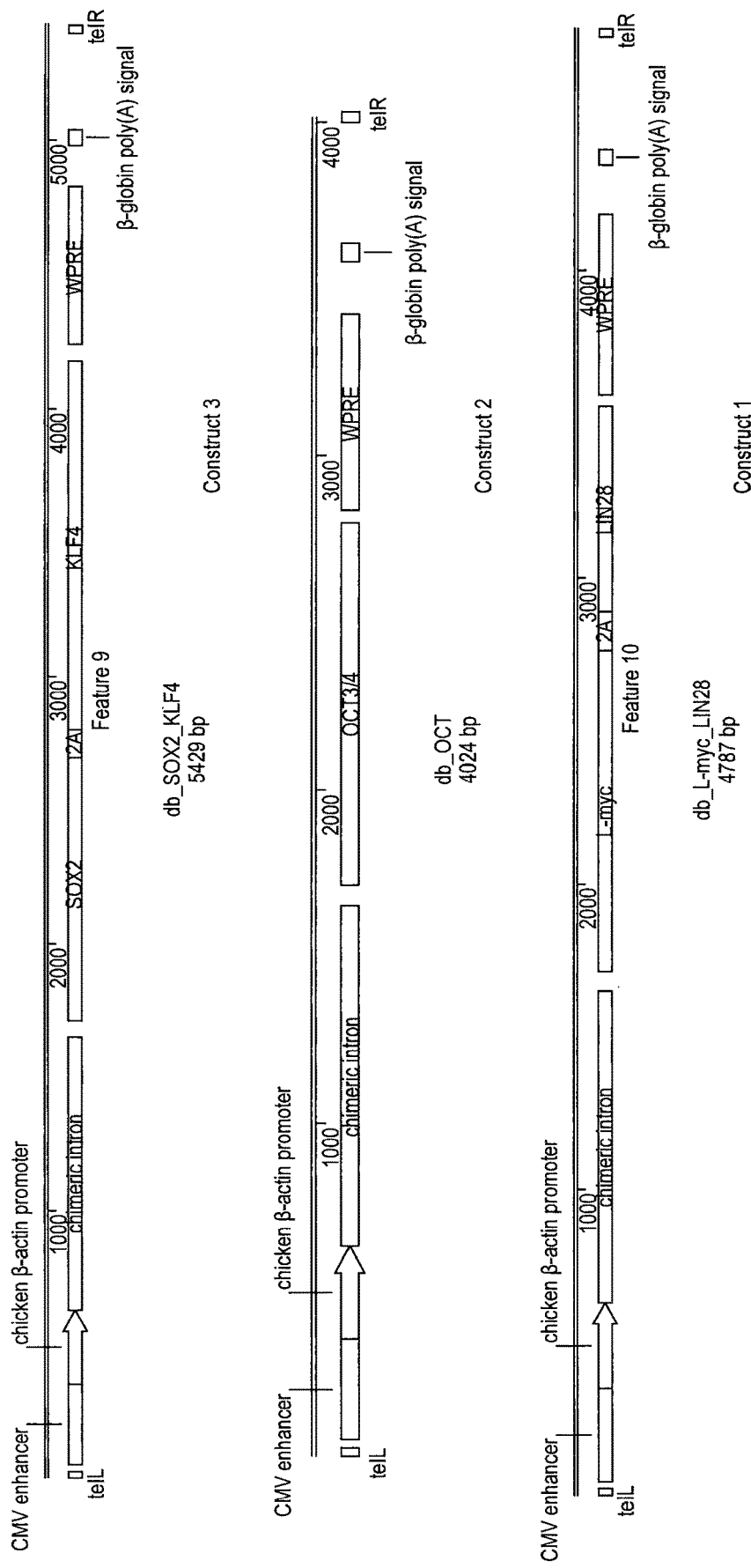
FIG. 1: Vector maps outlining the contents of the closed linear DNA (denoted in the figures as dbDNA) reprogramming constructs. Construct 1 refers to dbDNA-hUL including the two transgenes L-myc & LIN28. Construct 2 is dbDNA-OCT3/4, differing to the OriP-EBNA1 transgene in that there is no inclusion of the shp53 within the closed linear DNA construct. Finally, construct 3 refers to dbDNA-hSK, including the two transgenes SOX2 & KLF4. The closed linear DNA system used in the Examples is therefore a 3 vector system composed of 5 transgenes which can be used to induce reprogramming.

| Plasmid | Catalogue number | Construct | Concentration |
|---|---|---|---|
| pCXLE-hSK | Addgene ID: 27078 | dbDNA-hSK | 2.33 µg |
| pCXLE-hUL | Addgene ID: 27080 | dbDNA-hUL | 2.33 µg |
| pCXLE-hOCTshp53 | Addgene ID: 27077 | dbDNA-OCT4 | 2.33 µg |
| pCXLE-EBNA1 | Addgene ID: 37624 | Depicted on FIG. 1 | |

Firstly, 110 µl of Nucleofector solution was produced. This consisted of 90 µL NHDF Nucleofector™ solution+20 µL of Supplement 1 (LONZA: VPD-1001). 8 µg total was then deposited in the Nucleofector solution. ~4.5×10$^5$ hDFs were subsequently re-suspended in the Nucleofector/plasmid solution before being transferred into a cuvette and nucleofection taking place (P-022 programme: Human dermal fibroblasts—high viability). Cells were then seeded onto a single 6-well in complete DMEM—this would be considered day 0.

Subsequently, on day 1 the medium was refreshed before being changed continually every 2 days. Upon reaching a confluency of >90%, the hDFs were then passaged and seeded into a T75 cm² flask. On day 8, the re-programming hDFs were dissociated utilising 150 μL/cm² TrypLE®, before 60,000 cells were re-plated onto a T25 cm² containing feeder layer iMEFs. Furthermore, after 24 hours the cell medium was then exchanged from complete DMEM to hESC media which was likewise replenished every 2 days.

TABLE 5

Lab protocol for iPSc production.
Process begins at Day 0 with the transfection of fibroblasts with the reprogramming factors (with whichever vector).
The cells are continually cultured in complete DMEM and split accordingly.
On Day 8, 60,000 cells are replated onto a iMEF feeder layer in a T25 cm² prior to a switch to hESC media. The cells are continually cultured until colony formation.

| Day from transfection | Action |
|---|---|
| Day 0 | Fibroblast Nucleofection |
| Day 4-8 | Mesenchymal to Epithelial transition |
| Day 8 | Re-plate 60,000 cells onto iMEF feeder layered T25 cm² |
| Day 9 | Switch to hESC media |
| Day 18-21 | Early colony formation |
| Day 24-30 | Mature iPSC colony formation |

TABLE 6

Molecular Biology reagents:

| Reagent | Company |
|---|---|
| RIPA buffer | Thermo Scientific |
| Bradford reagent | BioRad |
| Acrylamide/bis-acrylamide 40% | Sigma |
| TEMED | Sigma |
| Tween ® 20 (surfactant) | Sigma |
| Precision Plus Protein ™ Kaleidoscope ™ Pre-stained Protein Standards | Biorad |
| Marvel original dried skimmed milk | Supermarket |
| Protease inhibitor cocktail | Sigma Aldrich |
| Phosphate buffered saline tablets | Sigma |
| Immobilon Western Chemiluminescent HRP Substrate | Merck |
| APS | Sigma |
| Blot absorbent filter paper | Biorad |
| Methanol | Fisher scientific |
| Glycine | Sigma |
| Tris base | Fisher scientific |
| Sodium dodecyl sulphate | |
| Proteinase K | Fisher scientific |
| QIAprep ® spin miniprep kit | Qiagen |
| RNeasy ® mini kit | Qiagen |
| RQ1 RNase-free DNase kit | Promega |
| dNTPs | Promega |
| M-MLV reverse transcriptase | Promega |
| RNasin ® plus inhibitor (ribonuclease inhibitor) | Promega |
| Random primers | Promega |
| KAPA ® SYBR ® FAST universal 2× qPCR master mix | KAPA Biosystems |
| GelRed ® nucleic acid gel stain | VWR International |
| Agarose | Sigma |
| O'Generuler ladder mix | Fisher Scientific |
| Isopropanol | Sigma |
| 4% Paraformaldehyde | |
| Triton 100× | Sigma |
| Bovine serum albumin | Sigma |

Immunocytochemistry:

Culture medium was firstly removed from the cells cultured on tissue culture treated plastic wells before being washed 3 times with DPBS. The cells were then fixed using 4% Paraformaldehyde (PFA) (v/v) in PBS at room temperature for approximately 20 minutes. The cells were then washed, again following fixation before then being permeabilised if the protein of interest was not membranous. Permeabilisation was carried out utilising 0.3% Triton X (v/v) in PBS for 10 minutes at room temperature. Subsequent to permeabilisation, the cells underwent further DPBS washes prior to then being blocked for a minimum of 30 minutes using 2% bovine serum albumin (BSA) (w/v)+0.1% (v/v) Tween® 20 in PBS. Primary antibodies were then diluted to appropriate concentrations (table) in blocking buffer and were subsequently incubated at 4° C. overnight. The cells were thereafter washed before the secondary antibody was diluted (1:500) in block and left on cells for 1 hour at room temperature in the dark. Following further wash steps, DAPI was added in PBS for 1 minute before being removed and the cells visualised on a Leica CTR 6000 live cell imaging microscope.

TABLE 7 antibodies

| Antibody | Dilution | Catalogue No |
|---|---|---|
| OCT4 | 1:100 | Abcam (Ab18976) |
| SOX2 | 1:200 | Biotechne (AF2018) |
| SSEA1 | 1:200 | Abcam (Ab16285) |
| βIII-tubulin | 1:200 | R&D systems (MAB1195) |
| α-Smooth muscle actin (SMA) | 1:100 | Abcam (ab5694) |
| SOX17 | 1:60 | R&D systems (AF1924) |

Vector Rescue and PCR Detection:

Cells were transfected/nucleofected and incubated for a minimum of 24 hours before being lysed for vector rescue. Thereafter, medium was removed from the cells before being washed using DPBS and trypsinised with 150 μL/cm² of TrypLE®. The cells were pelleted after being centrifuged at 1000 rpm (Eppendorf centrifuge 5804 R) for 5 minutes. The following steps outlined in Table 8 utilised components from the QIAprep® Spin Mini-Prep Kit:

TABLE 8 steps

| Step | Action |
|---|---|
| 1 | Cells re-suspended in 250 μl Buffer P1 before 250 μl Buffer P2 added. Incubate room temp for 5 minutes |
| 2 | 20 μl Proteinase K (20 mg/ml) was added to the cell suspension before incubating at 55° C. for 1-2 hours. |
| 3 | 350 μl Buffer N3 added to lysate and agitated. Stored on ice for 5 minutes. Lysate centrifuges 13,000 rpm for 10 minutes |
| 4 | Supernatant to mini-prep spin column and centrifuged 1 minute. Flow through discarded. |
| 5 | 500 μl Buffer P8 added to the spin column, centrifuged 1 minute, flow through discarded. 750 μl Buffer PE added and centrifuged 1 minute, flow through discarded. 1 minute empty spin to dry membrane. |
| 6 | Spin column allowed to air dry-removes ethanol 30 μl water placed into the column and allowed to stand for 1 minute before being centrifuged for 1 minute to elute any vector |

Subsequent to vector isolation, PCR analysis was carried out to amplify any vector present in a semi-quantifiable and qualitative manner. Primers were designed to amplify a non-transcribed region of each vector—the CAG enhancer (Sequence Below). At relevant time points, vector rescue samples were analysed for the presence of the CAG enhancer DNA sequence using a PCR with 25 cycles for semi-quantitative measurement and 35 cycles for qualitative measurement.

```
Sequences: CAG Enhancer:
Forward primer:
ACGCCAATAGGGACTTTCCA

Reverse Primer:
TAGGGGGCGTACTTGGCATA
```

TABLE 9

| Reaction Setup: | |
|---|---|
| Reagent | Volume |
| Q5 high fidelity DNA polymerase | 0.5 μL |
| Q5 5× Reaction buffer | 5 μL |
| 10 mM dNTPs | 0.5 μL |
| 10 μM Forward primer | 1.25 μL |
| 10 μM Reverse Primer | 1.25 μL |
| Sample | 2 μL |
| H₂O | 9.5 μL |

PCR Cycles Parameters:
Semi-Quantitative Vector Detection:
95° C.×5 minutes, 95° C.×15 seconds*, 60° C.×30 seconds*, 72° C.×60 seconds* (* marked for 25 cycles), 72° C.×5 minutes, HOLD at 10° C.
Qualitative Detection of Vector:
95° C.×5 minutes, 95° C.×15 seconds , 60° C.×30 seconds , 72° C.×60 seconds  ( for 35 cycles), 72° C.×5 minutes, HOLD at 10° C.
RNA Extraction, cDNA Synthesis:
RNA Extraction from Human Cell Lines:

Total RNA extraction was carried out utilising the Qiagen RNeasy® Minikit and its subsequent protocol. During extraction, the RNA undergoes a DNase treatment on-column, using the RQ1 DNase kit (Promega). The Minikit adopts the use of a silica membrane, which binds RNA from cell lysates. The high purity RNA was furthermore eluted from the column using 30 μL of RNase free water before being stored at −80° C. For cells that may be difficult to lyse, a plastic pestle was utilised during the homogenisation step.
cDNA Generation from RNA Using Reverse Transcriptase:

An RNA starting product was utilised to synthesise a first strand cDNA using Promega Moloney Murine Leukaemia reverse transcriptase alongside random hexamer primers (Promega). 1 μg of RNA was added to 0.5 μg (1 μL) of random primers which was likewise made up to 15 μL total volume in H₂O. The sample was then heated to 70° C. for 5 minutes-preventing secondary structure formation, before being immediately cooled on ice. Subsequently, the constituents in table 10 were then added in the following order to promote a reverse transcriptase reaction and cDNA synthesis:

TABLE 10

| Components | |
|---|---|
| Component | Volume |
| M-MLV Reaction buffer | 5 μL |
| dNTPs | 5 μL |
| RNAsin | 0.6 μL |

TABLE 10-continued

| Components | |
|---|---|
| Component | Volume |
| M-MLV Reverse Transcriptase | 1 μL |
| dH₂O | up to 25 μL |

The reaction was then incubated for 60 minutes at 37° C. before being subsequently stored at −20° C.
iPSC Pluripotent RT-PCR Characterisation:

Endogenous expression of key pluripotency factors was determined through Reverse transcriptase-PCR (RT-PCR) amplification. RNA was isolated utilising the Qiagen RNeasy® Minikit as aforementioned. cDNA synthesis was likewise initiated using Promega Moloney Murine Leukaemia reverse transcriptase alongside random hexamer primers. cDNA was then utilised as the starting product for RT-PCR amplification-contents as outlined in table 11.

TABLE 11

| components | |
|---|---|
| Component | Volume |
| (5×) Q5 Reaction Buffer | 5 μL |
| 10 mM dNTPs | 0.5 μL |
| 10 μM Primer (forward/reverse) | 2.5 μL |
| cDNA | 1.0 μL |
| Q5 High-fidelity DNA polymerase | 0.25 μL |
| ddH₂O | up to 25 μL |

TABLE 12

| Primers | | |
|---|---|---|
| Target | Forward primer | Reverse primer |
| Endogenous OCT4 | GCGATCAAGCAGCG ACT | TTCACCTTCCCTCC AACC |
| Endogenous SOX2 | CATGTCCCAGCACT ACCAGA | GGGTTTTCTCCATG CTGTTT |
| Endogenous LIN28 | TGTCCAAATGCAAG TGAG | GCAGGTTGTAGGGT GATTCC |
| NANOG | TTTGTGGGCCTGAA GAAAACT | AGGGCTGTCCTGAA TAAGCAG |
| E-Cadherin | TGCCCAGAAAATGA AAAAG | GTGTATGTGGCAAT GCGTTC |
| RN18S1 | ACACGGACAGGATT GACAGA | GGACATCTAAGGGC ATCACAG |

Figure 2A:
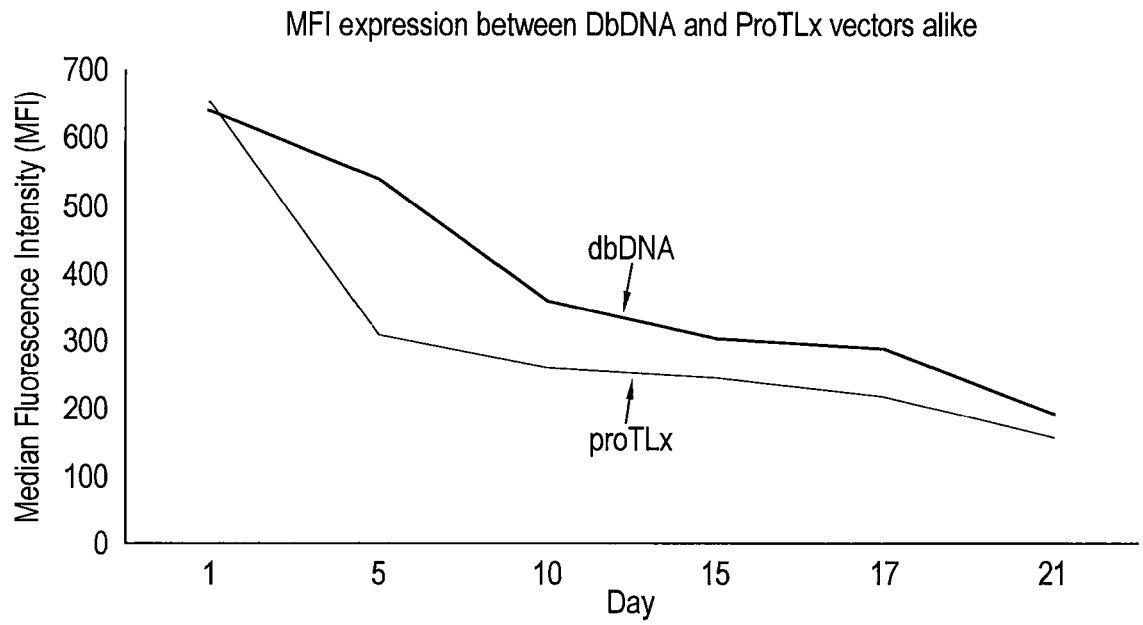
FIG. 2A: A plot showing the median fluorescence intensity (MFI) values for the expression of Green fluorescent protein (GFP) from cells transfected with either closed linear DNA or the plasmid from which the closed linear DNA was derived: dbDNA-eGFP or proTLx plasmid-eGFP. MFI values were collected from expressing cells over six time points. The MFI value offers indications into the intensity of GFP expression and as such can provide insight into how many cells express GFP and the intensity of expression.

PCR Cycling Parameters:
98° C.×5 minutes, 98° C.×30 seconds*, 55° C.×30 seconds*, 72° C.×60 seconds* (* for 35 cycles), 72° C.×5 minutes Example 1: Comparisons of Expression-GFP We looked into the intensity of expression from the vectors once transfected into cells. This was done using GFP as a marker, and cells were transfected with a closed linear DNA (dbDNA-eGFP) vector expressing GFP, or with a plasmid (proTLx plasmid-eGFP) that contains the identical sequence of the closed linear DNA vector, also expressing GFP, but also including a backbone sequence not present in the closed linear DNA vector. Therefore the comparison was between the same sequences presented in different formats. The plasmid did not contain OriP/EBNA1. The cells were transfected and the intensity of expression within GFP positive cells measured. An analysis of the cells median fluorescence intensity (MFI) was undertaken. MFI provides data on the intensity of expression within the GFP positive population of cells. Median fluorescence intensity values for both dbDNA-eGFP & proTLx plasmid-eGFP expressing cells over six time points. FIG. 2A is a plot of the results. The MFI value indicates intensity of GFP expression. It can be seen from FIG. 2A that the MFI values for the closed linear DNA vector are higher than those from the comparable plasmid, leading to the conclusion that the structure of the vector is important to the expression of the gene. From these results it is clear that the closed linear DNA vector expresses more GFP than the comparable sequence in the plasmid.

The results demonstrate how the dbDNA-eGFP vector displays a significantly extended longevity to the plasmid based proTLx system. The vector expressed in a higher percentage of cells at every time point beyond day 1 and as such, its expression was retained during the experimental time course. The median fluorescence intensity (MFI) calculated for both the proTLx & dbDNA vectors demonstrates that the dbDNA vector not only expressed with a greater longevity than its plasmid counterpart, but likewise expressed with a greater intensity too.

Figure 2B:
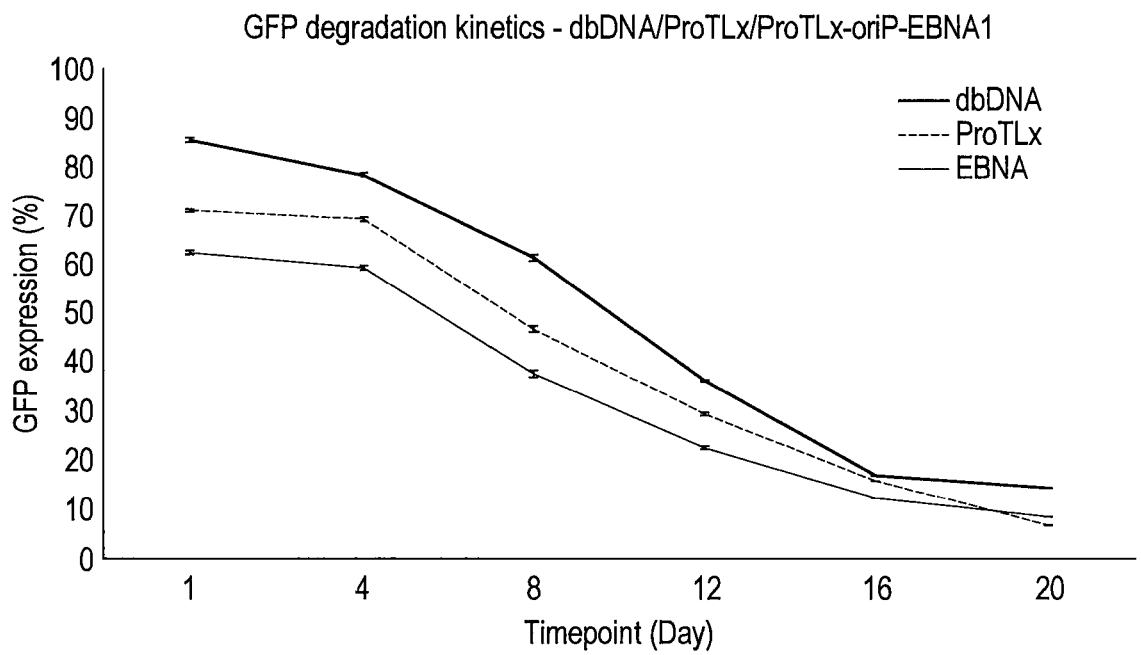
FIG. 2B: A plot showing GFP Degradation kinetics in an experiment where cells were transfected with one of: closed linear DNA (dbDNA), the plasmid from which closed linear DNA was derived (proTLx) or proTLx with the addition of OriP/EBNA1. Measurements are taken from expressing cells at six time points up until 20 days from transfection.

To further analyse expression from the closed linear DNA vector, analysis of the kinetics of GFP degradation were completed, with using the methods outlined above. Cells were transfected with one of: closed linear DNA (dbDNA), the plasmid from which closed linear DNA was derived (proTLx) or proTLx with the addition of OriP/EBNA1. Measurements are taken from expressing cells at six time points up until 20 days from transfection, and plotted as FIG. 2B. These results show that the closed linear DNA vector permitted the highest level of expression along the course of the experiment.

Example 2: Reprogramming Using Closed Linear DNA Vectors Versus OriP-EBNA1 Vectors Following confirmatory analysis that closed linear DNA reprogramming vector upregulated desired protein production (data not shown) and displayed a relative functionality, reprogramming experiments were undertaken. The OriP-EBNA1 construct was also utilised within the experiment for comparative purposes, while acting as a positive control for the closed linear DNA (FIG. 1). A total of 8 µgs of both closed linear DNA or OriP-EBNA1 vectors were separately transfected into HDFs before culturing as per the lab protocol (table 8). CLN3-HDFs were firstly utilised which had been isolated from patients diagnosed with Battens disease, with the biopsies taken in 2017. The cells had been demonstrated through previous reprogramming experiments to have a pluripotent capacity and had been demonstrated to produce early iPS cells but had not been successfully stabilised. These cells were, therefore, relatively resistant or intransigent to reprogramming.

Figure 3:
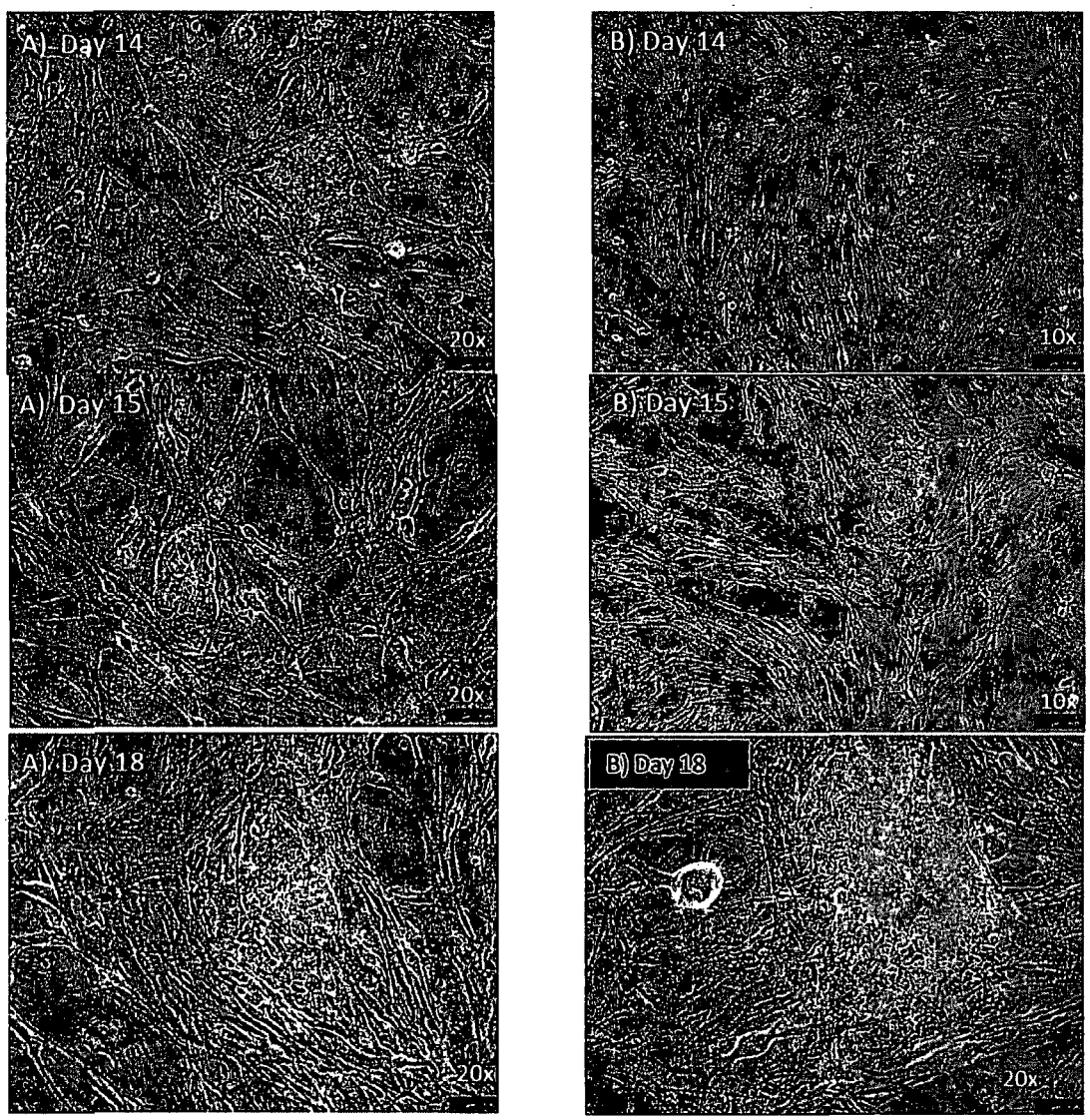
FIG. 3 (A and B, both day 14, day 15 and day 18): Photographs. Examples of early colony development over different time points during reprogramming. Fibroblasts had been nucleofected with both closed linear DNA (dbDNA) and OriP-EBNA1 reprogramming vectors. A) Represents closed linear DNA transfected cells and early colony formation between day 14 and day 18. B) Represents OriP-EBNA1 transfected cells and early colony formation likewise between day 14 and day 18. The images are representative of the same experiment over the stated period.

FIG. 3 shows examples of early colonies as they developed during this experiment. Those marked A were transfected with closed linear DNA vectors, and B with OriP-EBNA1 vectors.

Subsequently, the cells were continually passaged in order to mediate cells through the maturation period of iPS development into the transgene independent stabilisation period. Prior to this experiment, iPS cells produced from CLN3-hDFs had not undergone stabilisation to produce bona-fide iPS cells. Furthermore, the cells procured from this reprogramming experiment from OriP-EBNA1 vectors did not stabilise beyond passage 5, undergoing spontaneous differentiation (data not shown). Yet, iPS cells produced from dbDNA reprogramming vectors produced iPS cells of a more stable nature that are still persisting at passage 18.

Figure 4:
FIG. 4: Photographs. These images represent early iPS colonies produced by transfection by either closed linear DNA or plasmid with OriP-EBNA1. The cells depicted are all passage 1 cells following passaging from the initial reprogramming flask.
Figure 4:
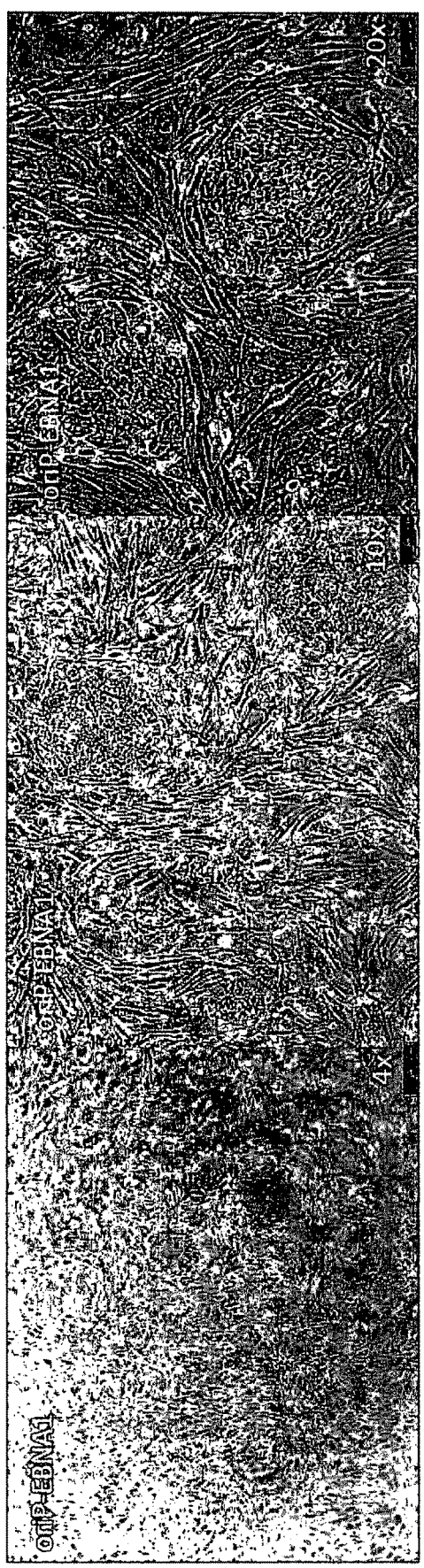
Figure 5:
FIG. 5: Passage 16 iPS cells generated from dermal fibroblasts taken from a patient with CLN3 Batten disease and transfected with closed linear DNA. No pictures of cells obtained via OriP-EBNA1 transfection were available, as the cells had already undergone differentiation. Thus, the cells transfected with closed linear DNA (dbDNA-iPSC) based reprogramming factors were more stable and retained their pluripotent characteristics far better than the cells transfected with the same factors on a plasmid bearing OriP/EBNA1.

Relevant photographs of the cells are shown in FIGS. 4 and 5.

This demonstrates that closed linear DNA vectors are an effective vehicle for the expression of reprogramming factors in donor cells that have previously been resistant to reprogramming methods using alternative vectors. Indeed, the standard plasmids failed to reprogram the cells in this experiment.

Example 3: Determination of Pluripotency

Subsequent to the production of cells that morphologically resemble iPS cells, we carried out characterisation tests to ensure the cells function as a pluripotent cell too. Therefore, to determine that the cells were pluripotent by nature and expressing key pluripotent markers, immunocytochemical staining (ICC) was deployed. A number of markers were selected that were both transgene related and endogenous alike. OCT4 & SOX2 are transgene specific markers of pluripotency that were chosen. Both OCT4 & SOX2 are critical to the re-constitution of pluripotency and the maintenance of the cells self-renewal capacity-therefore iPS cells should likewise stain positively for the presence of both of these pluripotency markers. Yet, it is also important to stain for pluripotency markers that are not over-expressed through the transfected transgene. TRA-1-81 is a keratin sulphate proteoglycan that is commonly expressed in undifferentiated cells and is significantly downregulated during differentiation. Being an endogenous marker which is positively expressed therefore demonstrates that the cells have undergone complete reprogramming to re-constitute pluripotency. Furthermore, NANOG, another endogenous pluripotency factor, was furthermore stained for in dbDNA iPS cells but OriP-EBNA1 iPS colonies had undergone differentiation by this point and further data could not be collected. NANOG is a transcription factor that likewise works to maintain pluripotent cellular division and self-renewal.

Again, closed linear vectors resulted in reprogrammed cells that performed better than cells where the reprogramming vectors were included on standard episomal reprogramming plasmids.

Figure 6:
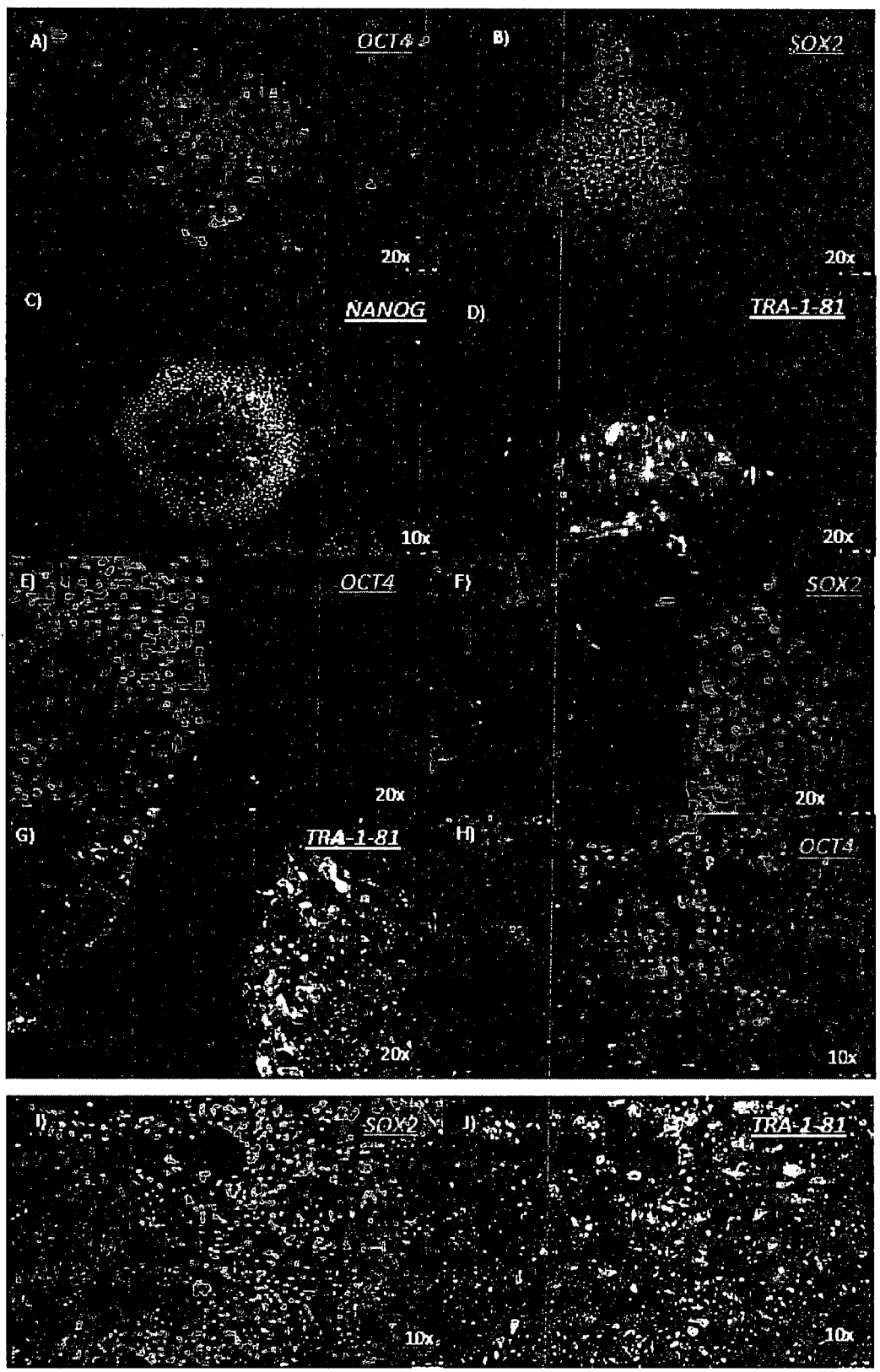
FIG. 6 (A to J): Photographs. Immunocytochemical staining (ICC) for pluripotent markers on iPS cells generated from dermal fibroblasts taken from a patient with CLN3 Batten disease and transfected with closed linear DNA, together with photographs of positive control cells: A) Closed linear DNA transfected cells marked for OCT4 expression. B) Closed linear DNA transfected cells marked for SOX2 expression. C) Closed linear DNA transfected cells marked for NANOG expression. D) Closed linear DNA transfected cells marked for TRA-1-81 expression. E) OriP-EBNA1 plasmid transfected cells marked for OCT4 expression. F) OriP-EBNA1 transfected cells marked for SOX2 expression. G) OriP-EBNA1 transfected cells marked for TRA-1-81 expression. H) Positive control feeder free ESC cells stained for OCT4. I) Positive control feeder free ESC cells stained for SOX2. J) Positive control feeder free ESC cells stained for TRA-1-81.

FIG. 6 shows the Immunocytochemical staining (ICC) of iPS cells for pluripotent markers.

Following successful characterisation utilising ICC staining for pluripotency factors, further characterisation tests were undertaken. Pluripotent cells maintain a capacity to differentiate into cells of the three germ layers. Therefore, iPS cells formed during reprogramming should be able to differentiate and form cells expressing endoderm, ectoderm and mesoderm markers. iPS cells produced from dbDNA reprogramming vector constructs were picked to form embryoid bodies (EB) before being re-plated permitting spontaneous outgrowth.

Subsequently, any spontaneous outgrowth derived from the plated EBs was stained for markers corresponding to cells of the 3 germ layers. Firstly, the cells were stained for SOX17, which is a transcription factor largely involved in ectodermal development and thus is a definitive ectodermal marker. Likewise, B-III-tubulin is a neuronal specific marker, which is one of the earliest markers of neuronal commitment and thus a perfect candidate for endodermal marker presence. Finally, concerning a mesoderm specific marker, α-Smooth muscle actin (α—SMA) was utilised which is a highly conserved cytoskeletal protein and is commonly utilised. As such, the outgrowth stained for these three markers should provide an insight into the differentiation potential of the iPS cells produced by the dbDNA reprogramming constructs.

Figure 7:
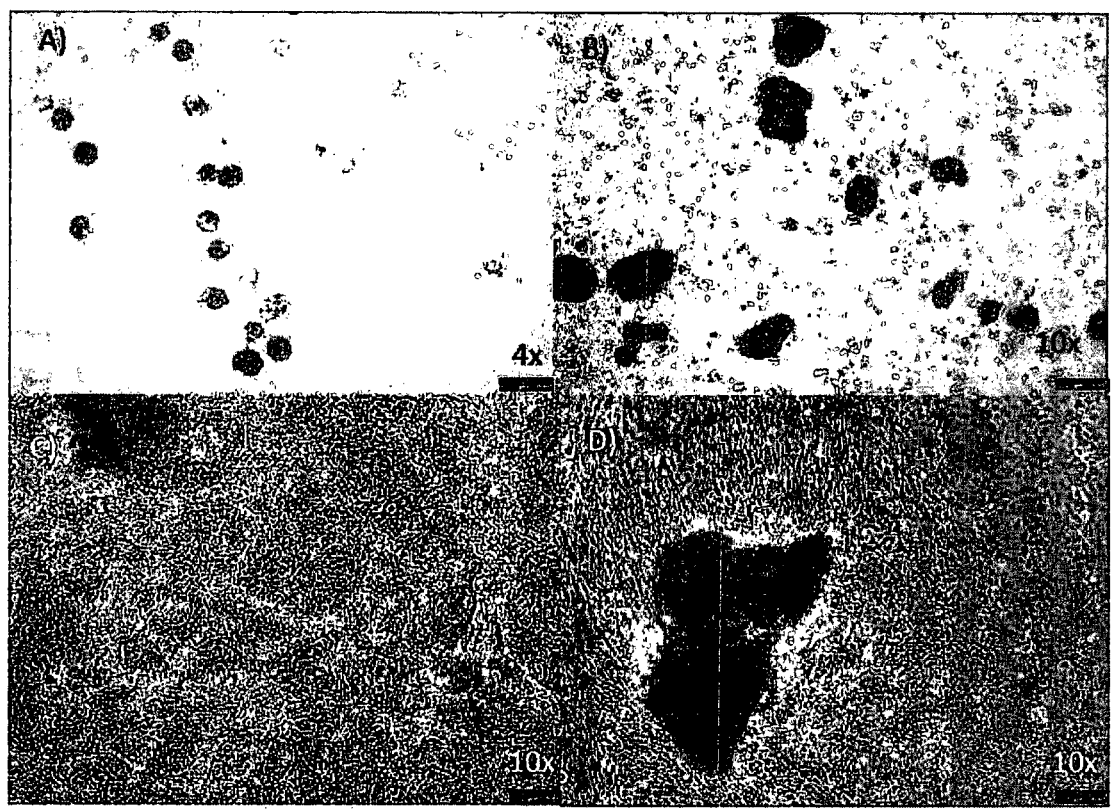
FIG. 7 (A to D): Photographs of embryoid bodies differentiated from CLN3 Batten disease iPSC. Dermal fibroblasts taken from a patient with CLN3 Batten disease and transfected with closed linear DNA, resulting in iPSc which were subsequently forced to differentiate into embryoid body formation after 8 days and subsequent spontaneous differentiation for a further 8 days. A) iPSCs induced with closed linear DNA forming embryoid bodies (magnification 4×). B) iPSCs induced with closed linear DNA forming embryoid bodies (magnification 10×). C) iPSCs induced with closed linear DNA forming embryoid bodies and then undergoing spontaneous differentiation (magnification 10×). D) iPSCs induced with closed linear DNA forming embryoid bodies and then undergoing spontaneous differentiation (magnification 10×).
Figure 8:
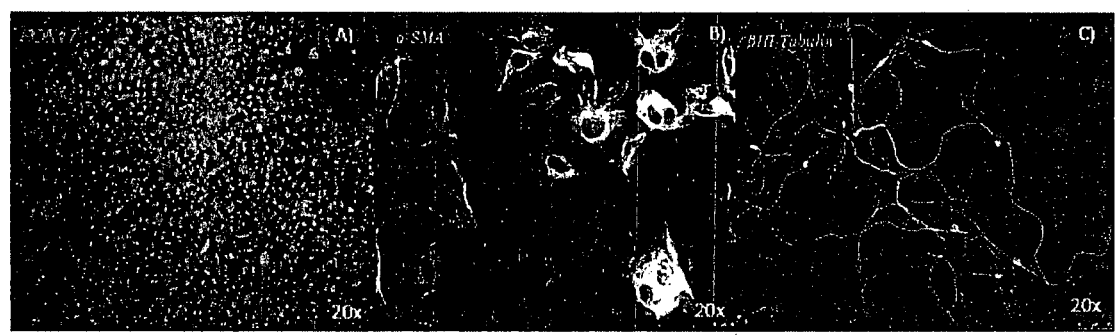
FIG. 8 (A to C): iPSCs induced with closed linear DNA: derived iPS outgrowth that has been positively stained for markers of the 3 germ lineages. A) SOX17 staining for endodermal lineages. B) α-Smooth muscle for mesodermal lineages. C) β-III tubulin for neurectodermal lineages. This demonstrates the ability of the iPS cells to form all three cell types, denoting the pluripotent capacity of the cells.

Photographs of these cells are shown in FIGS. 7 and 8. The cells behaved as expected for iPS cells, demonstrating closed linear DNA is an effective vector to carry out reprogramming.

Figure 16:
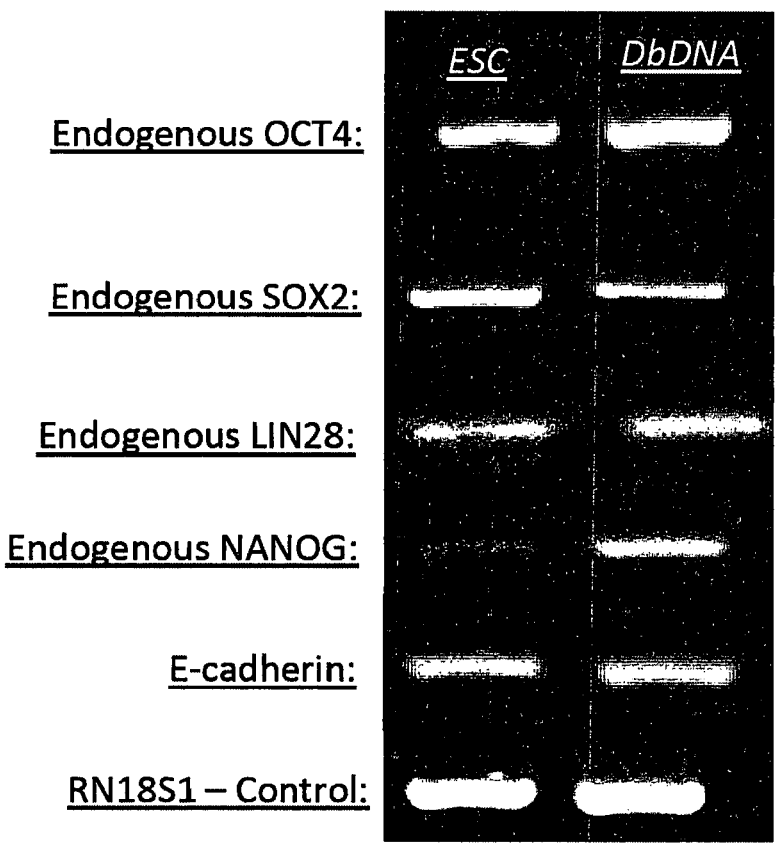
FIG. 16. Photograph of agarose gel electrophoresis. RNA isolated from ESCs and iPS cells (generated using reprogramming factors expressed by closed linear DNA vectors using dermal fibroblasts taken from a patient with CLN3 Batten disease) was reverse transcribed producing first strand cDNA prior to undergoing a PCR amplification specific for endogenous expression of pluripotency genes. PCR was run for 30 cycles. Endogenous expression of OCT4, SOX2, LIN28, NANOG, E-Cadherin was analysed. RN18S1 was used as a control.

Subsequently, a final step in the characterisation of iPS cells produced by dbDNA was an RT-PCR assay. RNA was isolated and reverse transcribed before endogenous expression of a number of pluripotency genes underwent semi-quantification in comparison to an ESC control. OCT4, SOX2 & LIN28 are all transgene expressed pluripotency factors, whilst NANOG and E-cadherin are independent endogenous pluripotency factors. The premise of the RT-PCR was to provide a semi-quantitative insight into endogenous pluripotency gene expression, with a ribosomal protein (RN18S1) control. Results are shown in FIG. 16.

The iPS cells produced by closed linear DNA vectors underwent a number of confirmatory analyses in which they produced positive results in ICC staining. Thus, the cells were shown to express pluripotency genes that are not just transgene-derived but also endogenously expressed. This indicates that the cells have a pluripotent capacity. ICC staining is a standard procedure carried out on iPS cells. The closed linear DNA transfection system offers identical positive staining to cells transfected by other methods with the added feature of the vector being a transient clinical-grade DNA vector. Moreover, a common feature noted in a qualitative examination of the two cell types is that the iPSCs generated using closed linear DNA seemingly display a reduced propensity to spontaneous differentiation. While the iPSCs are in pluripotency media, iPSCs made using closed linear DNA seem to maintain their pluripotent capacity to a greater degree than iPSCs generated using OriP-EBNA1. This could be for a number of reasons, including the more transient expression of the transgenes from the closed linear DNA. Yet, despite maintaining a minimal level of differentiation while in culture, the iPS cells were demonstrated to still convey a capability to differentiate when required and form cells of the 3 germ layers. Thus, these cells show all the characteristics of pluripotent stem cells.

Much of the previous literature describes difficulties associated with standard episomal plasmid reprogramming independent of the OriP-EBNA1 system. Plasmid alone is too transient to induct complete reprogramming—as shown in later Examples (proTLx system). As such the use of the oncoviral-derived OriP-EBNA1 system came into use to extend the vectors longevity but for periods far beyond iPS cell production. Closed linear DNA vectors, composed of GMP grade bacterial sequence free DNA; from a single transfection can produce iPS cells from a number of hDF lines. The construct has been demonstrated to produce highly functional iPS cells. This system therefore represents a new generation of safer reprogramming vectors capable of producing clinical grade iPS cells with a greater stability (less differentiation when cultured as pluripotent cells).

Example 4: Further Reprogramming Work

Figure 9:
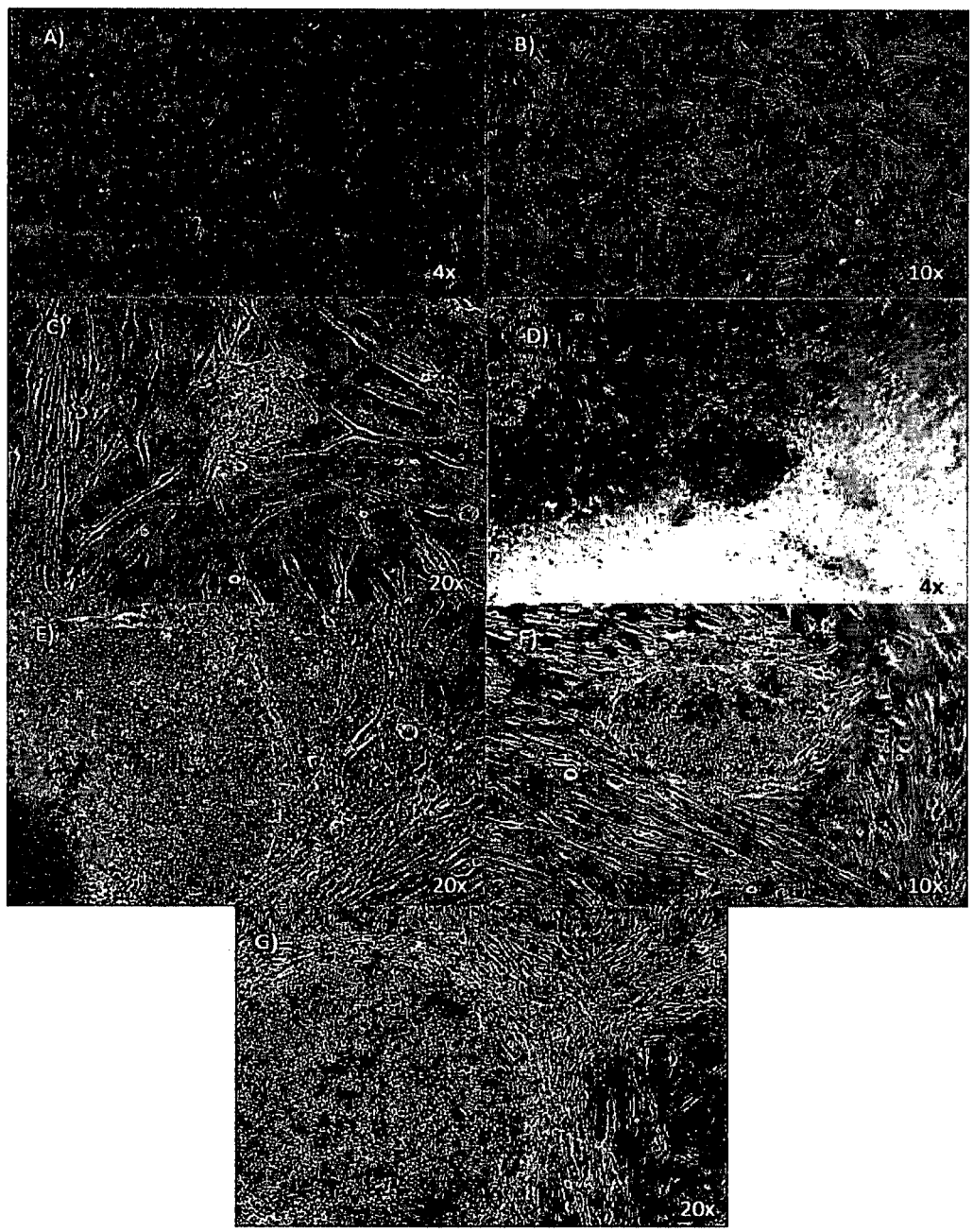
FIG. 9 (A to G): Data from an iPSC reprogramming experiment utilising dermal fibroblasts (hDFs) taken from a patient with CLN3 Batten disease and transfected with both closed linear DNA or OriP/EBNA1 vectors. A) starting hDFs Day 1 (magnification 4×). B) Example of mesenchymal to epithelial transition exhibited in cells being reprogrammed utilising closed linear DNA vectors (magnification 10×). C) Early potential colony formation on day 13 using closed linear DNA vectors (magnification 20×). D) Early closed linear DNA transfected donor cells to iPS colony formation on day 26 (magnification 4×). E) Early closed linear DNA transfected donor cells iPS colony formation on day 26 (magnification 20×). F) Early OriP/EBNA1 transfected donor cell to iPS colony formation on day 13 (magnification 10×). G) Early iPS colony formation from OriP/EBNA1 transfected donor cells at day 26 (magnification 20×).

A number of further reprogramming experiments were carried out in order to determine closed linear DNA vectors capabilities within reprogramming fibroblasts from a number of different origins. Fibroblasts from a different Batten disease genetic variant, CLN7, were utilised alongside control neonatal fibroblasts. This was in order to determine if the constructs had the capability of reprogramming "diseased" fibroblasts as well as healthy control fibroblasts too. Results are shown in FIG. 9. Further, cells of different origin were also reprogrammed, including kidney cells isolated from urine and monocytes isolated from peripheral bood.

Figure 13:
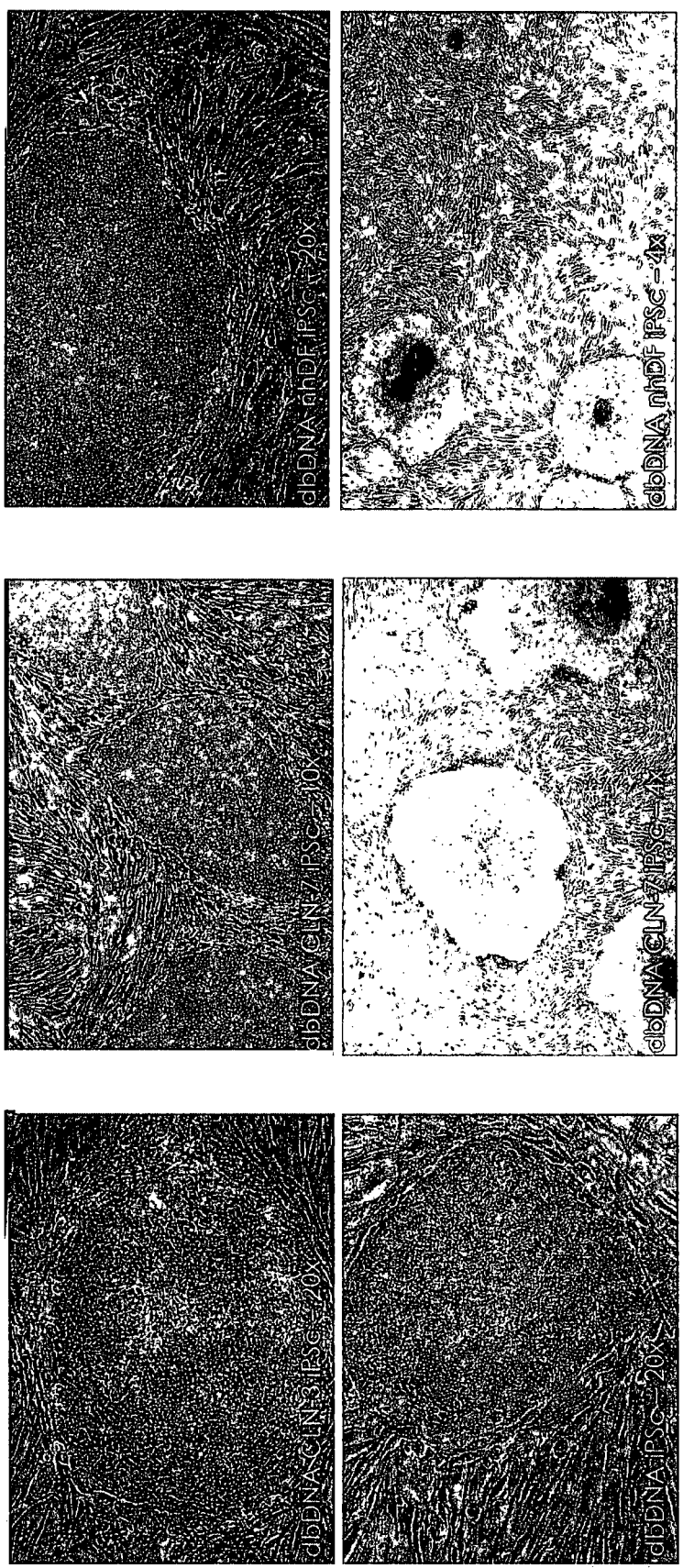
FIG. 13: IPS cells generated using reprogramming factors expressed by closed linear DNA vectors using various donor cells. The magnification is indicated where relevant. The cells are from patients with Batten disease "CLN3" (column 1), "CLN7" (column 2) or the cells are from non-diseased hDF (column 3). Cells were transfected with closed linear DNA ("dbDNA") vectors encoding reprogramming factors and the cells maintained in culture. Cells forming iPSC colonies were photographed. This demonstrates the utility of the invention in several cell types.

The iPS cells produced by transfection with both closed linear DNA vectors and OriP-EBNA1 constructs were subjected to confirmatory staining to ensure there was expression of both endogenous and transgene-expressed pluripotency factors. Results are shown in FIG. 13. In this Example, both vectors were capable of reprogramming donor cells.

Example 5: Reprogramming Previously Intransigent Cells

A further reprogramming experiment was carried out in dermal fibroblasts taken from a patient with CLN3 Batten disease that were previously unstable following reprogramming with OriP/EBNA1 constructs, and therefore failed to produce stable iPSCs. An experiment was undertaken to determine whether the closed linear DNA vectors could reprogramming these cells and produce stabilised iPS cells.

Both closed linear DNA vectors and OriP-EBNA1 vectors were used to transfect fibroblasts. As of passage 1 (FIG. 11), both vectors were capable of inducing reprogramming but later data (not shown) confirmed that standard episomal plasmid (OriP/EBNA1) could not maintain the reprogrammed cells without differentiation, whilst the cells transfected with closed linear DNA could maintain their pluripotency.

Example 6: Reprogramming: Comparison of Negative Control, proTLx Plasmid, Closed Linear DNA (dbDNA) and OriP-EBNA1 Plasmid Materials and Methods: Tables 13a, b and c-DNA Vectors for Reprogramming

| Construct | Concentration |
| --- | --- |
| proTLx-hSK | 2.33 μg |
| proTLx-hUL | 2.33 μg |
| proTLx-OCT4 | 2.33 μg |

| Construct | Concentration |
| --- | --- |
| dbDNA-hSK | 2.33 μg |
| dbDNA-hUL | 2.33 μg |
| dbDNA-OCT4 | 2.33 μg |

| Plasmid | Catalogue number |
| --- | --- |
| pCXLE-hSK | Addgene ID: 27078 |
| pCXLE-hUL | Addgene ID: 27080 |
| pCXLE-hOCTshp53 | Addgene ID: 27077 |
| pCXLE-EBNA1 | Addgene ID: 37624 |

110 μl of Nucleofector solution was produced consisting of 90 μL NHDF Nucleofector™ solution+20 μL of Supplement 1 (LONZA: VPD-1001). 8 μg total of DNA for dbDNA, OriP-EBNA1 and proTLx-K was then separately deposited in the Nucleofector solution. ~4.5×105 hDFs were re-suspended in the Nucleofector/DNA solution before being transferred into a cuvette and nucleofected (P-022 programme: Human dermal fibroblasts-high viability). Cells were then seeded onto a single 6-well in complete DMEM— this would be considered day 0.

On day 1, the culture medium was refreshed and changed continually every 2 days. On day 8, the re-programming hDFs were dissociated utilising 150 µL/cm² TrypLE®, before 30,000 cells were re-plated into a single 6-well containing feeder layer iMEFs. Furthermore, after 24 hours the cell medium was then exchanged from complete DMEM to hESC media which was replenished every 2 days. Subsequently, on Day 28, the cells underwent alkaline phosphatase staining to determine viable colony formation. A single SIGMAFAST™ BCIPR/NBT (B5655) tablet was completely dissolved in 10 ml of DPBS at room temperature. Any culture medium was firstly removed before the 2 mL SIGMAFAST™ BCIPR/NBT solution was added to the well. Following a room temperature incubation for ~30-60 minutes in the dark, the colonies were analysed using the EVOS™ XL Core Cell Imaging System for colour changes to indicate the presence of viable colonies. The colonies were analysed using the EVOS™ XI Core Cell Imaging System for colour changes to indicate the presence of viable colonies.

Figure 10A:
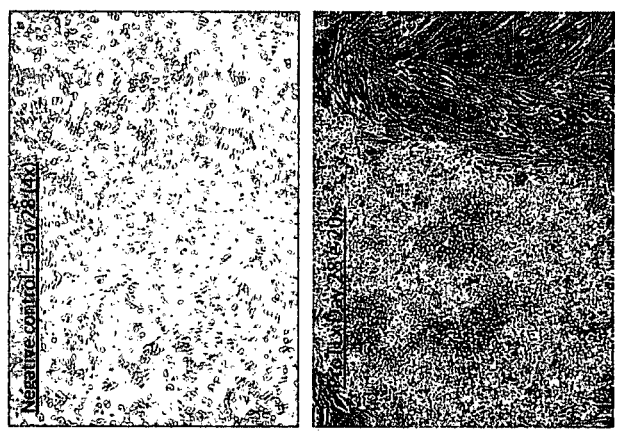
FIGS. 10A and 10B: cell photographs.
Figure 10A:
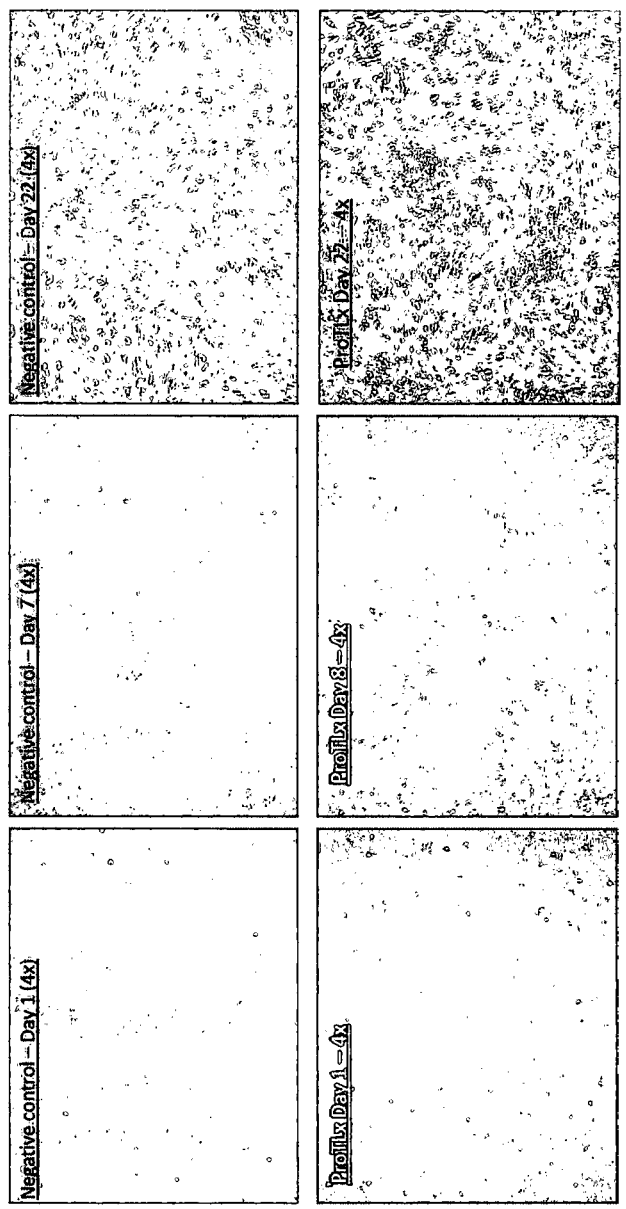
Figure 10B:
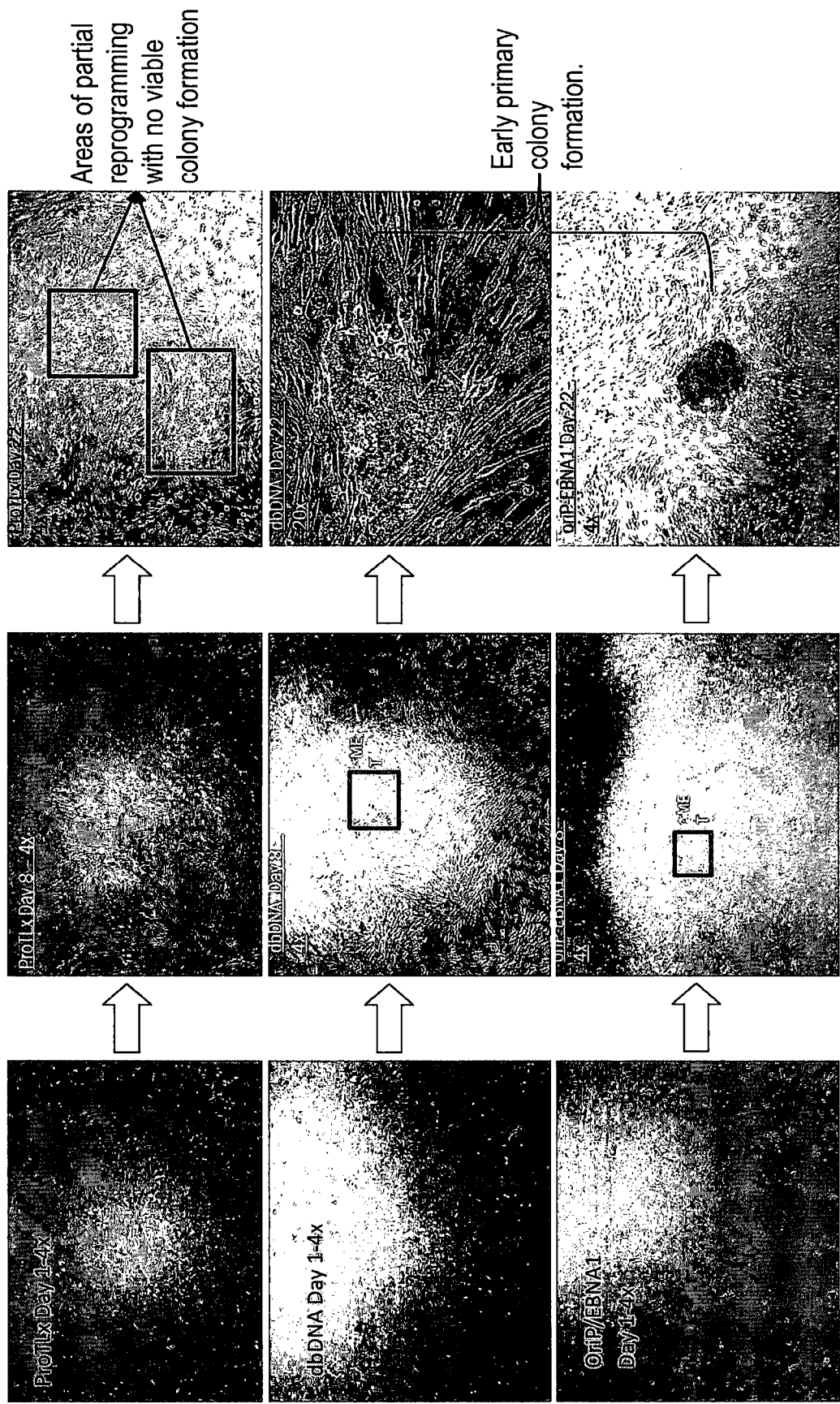
Figure 11:
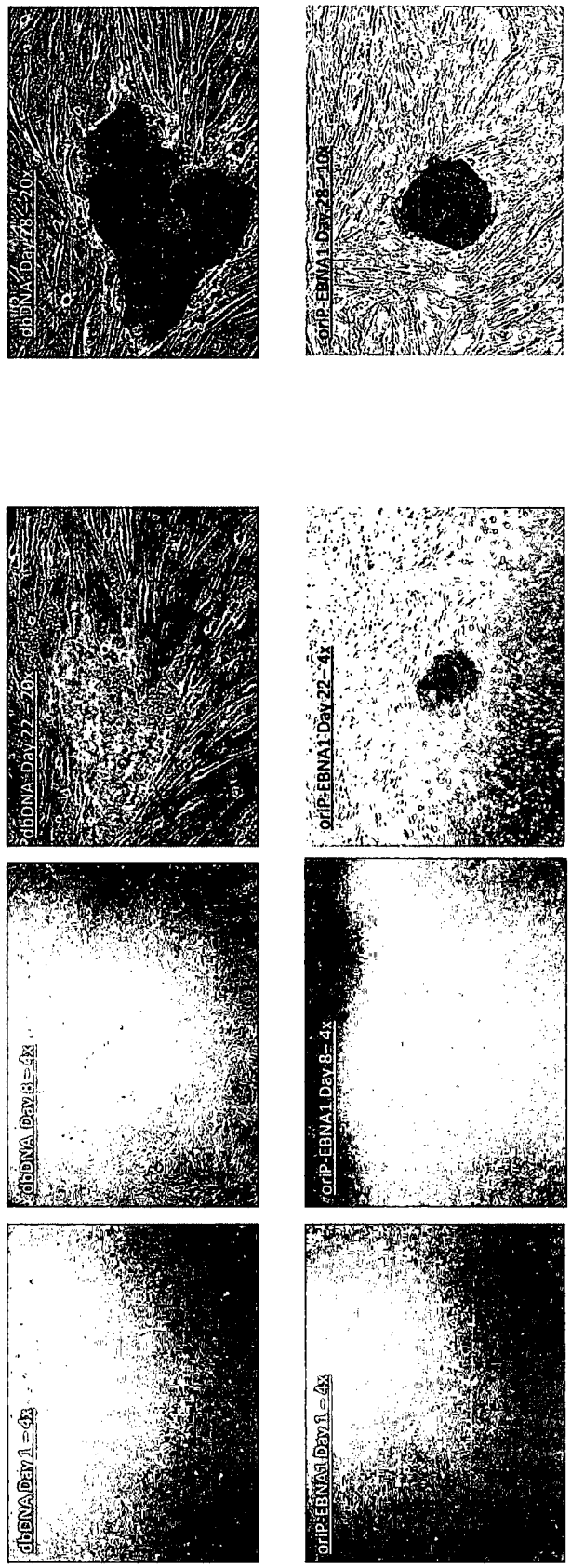
FIG. 11: cell photographs. These depict the initial results from reprogramming experiments with closed linear DNA and OriP-EBNA1 vectors. The first three panels for each cell type is a photograph of the cells on the depicted day. Alkaline Phosphatase Live Stain (AP) results are positive, indicating that these cells are pluripotent stem cells (last panels). Therefore, this shows that the closed linear DNA vectors expressed sufficient reprogramming factors to effect reprogramming.
Figure 12:
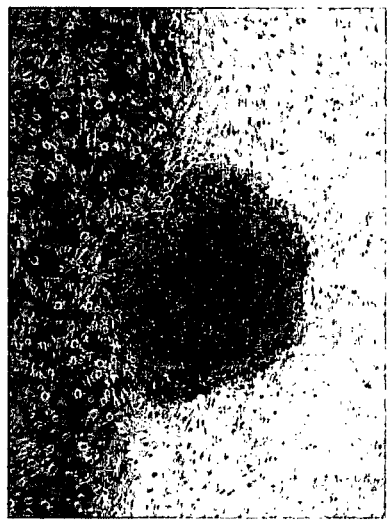
FIGS. 12 (A and B): Photographs showing the progression of iPS cells formed during the experiment. Where the donor cell was transfected with proTLx (plasmid without means for chromosomal attachment), no iPS cells were generated. Row A: closed linear DNA transfection, row B is OriP/EBNA1 transfection.
Figure 12:
Figure 12:
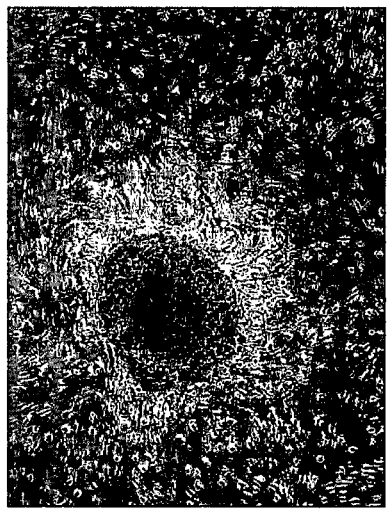
Figure 12:
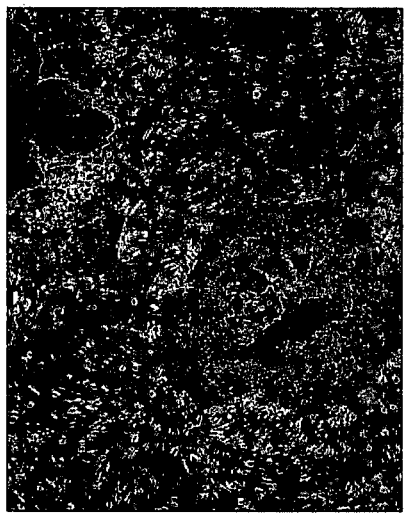
Figure 12:
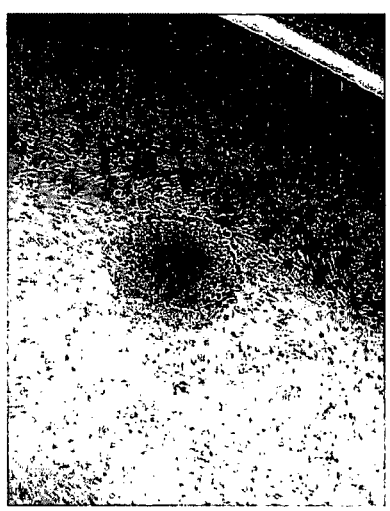
Figure 12:

The results are shown as FIGS. 10 to 12. This data clearly shows that it is not the sequence alone that is required for the reprogramming; the structure of the closed linear DNA is critical. The experiments with the plasmid containing the closed linear DNA vector sequence (which failed to reprogram cells) supports this conclusion.

Example 7: Vector Rescue

Vector specific primers were used to semi-quantitatively assess the retention of closed liner DNA vector verses OriP-EBNA1 vector at day 1 after nucleofection and 35 days after nucleofection. Vector was rescued as described in the Methods section and then subjected to PCR amplification with 25 and 35 cycles. Under both cycling conditions it was apparent that OriP-EBNA1 vector was retained to a greater degree than closed linear DNA vector.

Results are depicted in FIGS. 14A and 14B. The results clearly show that the closed linear DNA vector is retained in smaller quantities at the time-point at which the cells were tested, when compared to the equivalent OriP-EBNA1 vector.

Example 8: Cell Surface Markers of Pluripotency iPSCs induced either using the method of the invention (closed linear DNA) or a standard OriP-EBNA1 vector, were subjected to FACS analysis using the relevant antibody for the cell surface marker.

Cell surface antigen expression was assessed by immunofluorescence detected by flow cytofluorimetry after harvesting cultures as single cell suspensions using trypsin-EDTA, as previously described (Andrews P W, et al. In: Robertson E J, editor. Teratocarcinomas and Embryonic Stem Cells: a Practical Approach. Oxford: IRL Press; 1987. pp. 207-248, and Andrews P W, et al. Cancer Res. 1987; 47:740-746.)

The following monoclonal antibodies can be used to detect surface antigen expression:

Anti-Stage Specific Embryonic Antigen-3 (SSEA3), anti-Stage Specific Embryonic Antigen-1 (SSEA1), TRA-1-60 and TRA-1-81.

For SSEA1, A threshold of 40 relative fluorescence units was used to determine SSEA-1 positive cells, based upon the background staining presented in the isotype controls, the area under the histograms was calculated above and below these to determine the percentage. More positive cells were observed in EBNA1 induced cells, leading to the conclusion that the cells induced according to current state of the art techniques are demonstrating differentiation is starting to happen, and pluripotency is beginning to be lost.

FIG. 17 depicts the results for SSEA1 sampling.

Example 9: RNA Sequencing of Gene Expression in iPSCs

Analysis:

High throughput sequencing was performed on an Illumina NextSeq® 550 platform on total RNA preps. After sequence QC analysis, probes from pluripotent cells induced by closed linear DNA vectors (dbDNA) or oriP-EBNA1 vectors were as such subjected to a student's t-test analysis with a cut off p-value of ≤0.05. From this, the results were then subjected to a Benjamini-Hochberg analysis to determine the False discovery rate (FDR). This was to reduce the possibility of a type 1 error and thereby limit the inclusion of false positive results within the dataset. An FDR cut off≤0.05 was utilised. Subsequently, fold change expression was calculated between the cells induced using closed linear DNA (dbDNA) and oriP-EBNA1 vectors and probes with a fold change difference of ≥1.5 were taken forward.

Using these significant probes, software was utilised to determine transcription factor enrichment terms. The Reactome database (https://reactome.org) was utilised to project significant probes onto the human genome to help elucidate interacting pathways in relation to cell cycle, metabolism, immune function etc. Moreover, enrichment analysis was likewise undertaken using the MSigDB function from Gene Set Enrichment Analysis (GSEA). This function can then provide information on hallmark genes which summarise and represent specific well-defined biological processes generated via overlaps between gene sets within the MSigDB system. Subsequently, the analysis can provide a p-value for each hallmark process which demonstrates a measure of how significant the changes were for each given gene set; the higher the absolute value of the statistic, the greater its significance. GSEA also provides k/K values, whereby k=the number of genes in the query set and K=the number of genes in the MSigDB database. This can therefore provide information on the direction of change for the biological processes for each significant probe. Finally, a q-value is provided which is an FDR analogue of the p-value after correction for multiple hypothesis testing and again reduces the possibility of including false positive results.

Heatmap Production:

After the above analysis, probe expression values can be developed into heatmaps to provide a global visualisation of gene expression profiles for different cell types. Heatmaps were generated using R studio.

Heatmaps of the results obtained are depicted in FIGS. 18A-18B and 19A-19B.

Histogram Production:

After the above analysis, particular gene expression profiles can be obtained for specific genes, or for groups of particular genes. Various gene expression patterns are shown in FIGS. 20A and 20B.

Figure 20A:
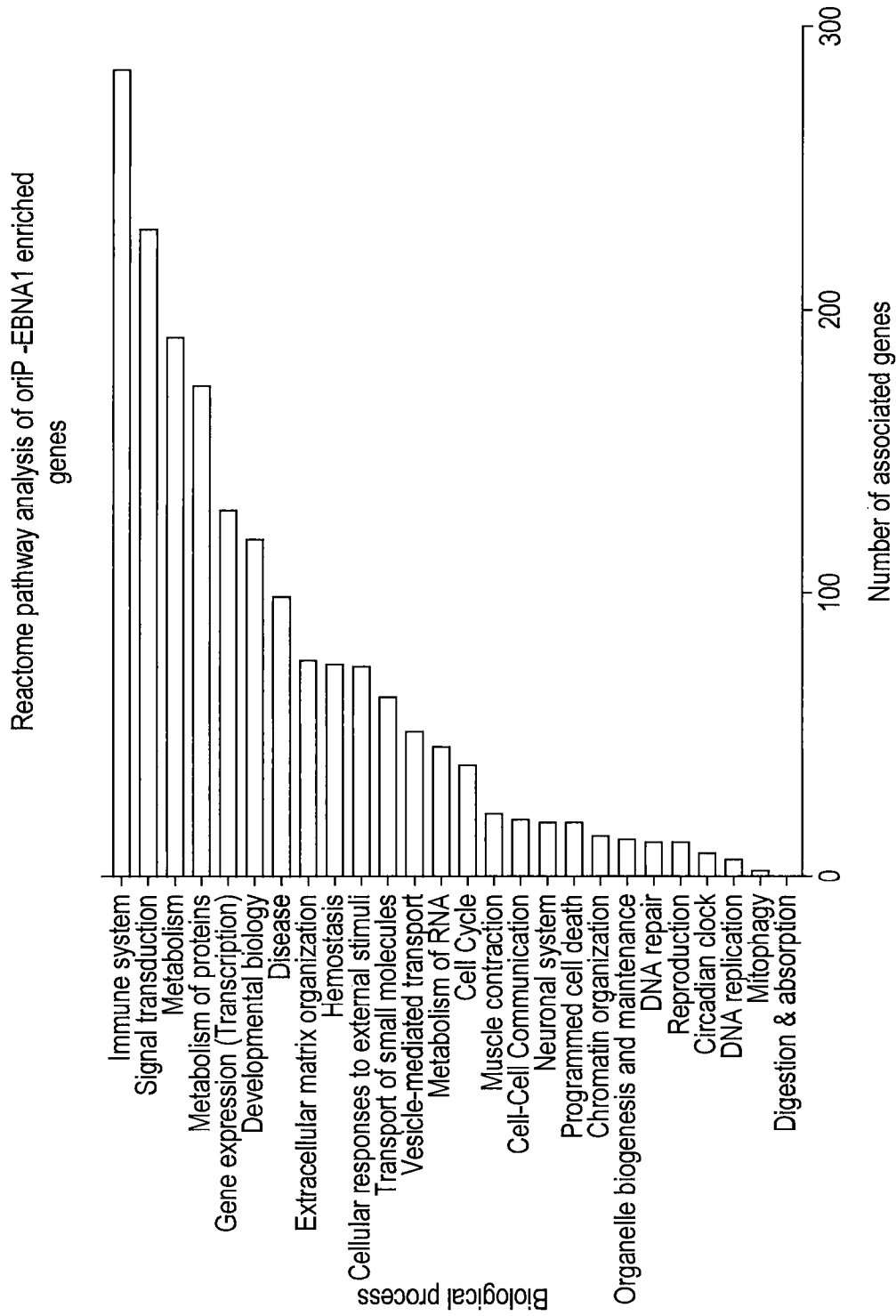
FIGS. 20A and 20B. Histograms from RNA sequencing data, Example 9.

FIG. 20A depicts the gene expression for cytokine signalling in the immune system and innate immunity. It can be seen that these genes are the most over represented reactomes in OriP/EBNA1 induced cells when compared to closed linear DNA (dbDNA) mediated iPSC generation. The most significantly over-represented transcripts in OriP/EBNA1 iPSC compared to closed linear DNA induced iPSC were then analysed using Reactome pathway analysis.

Figure 20B:
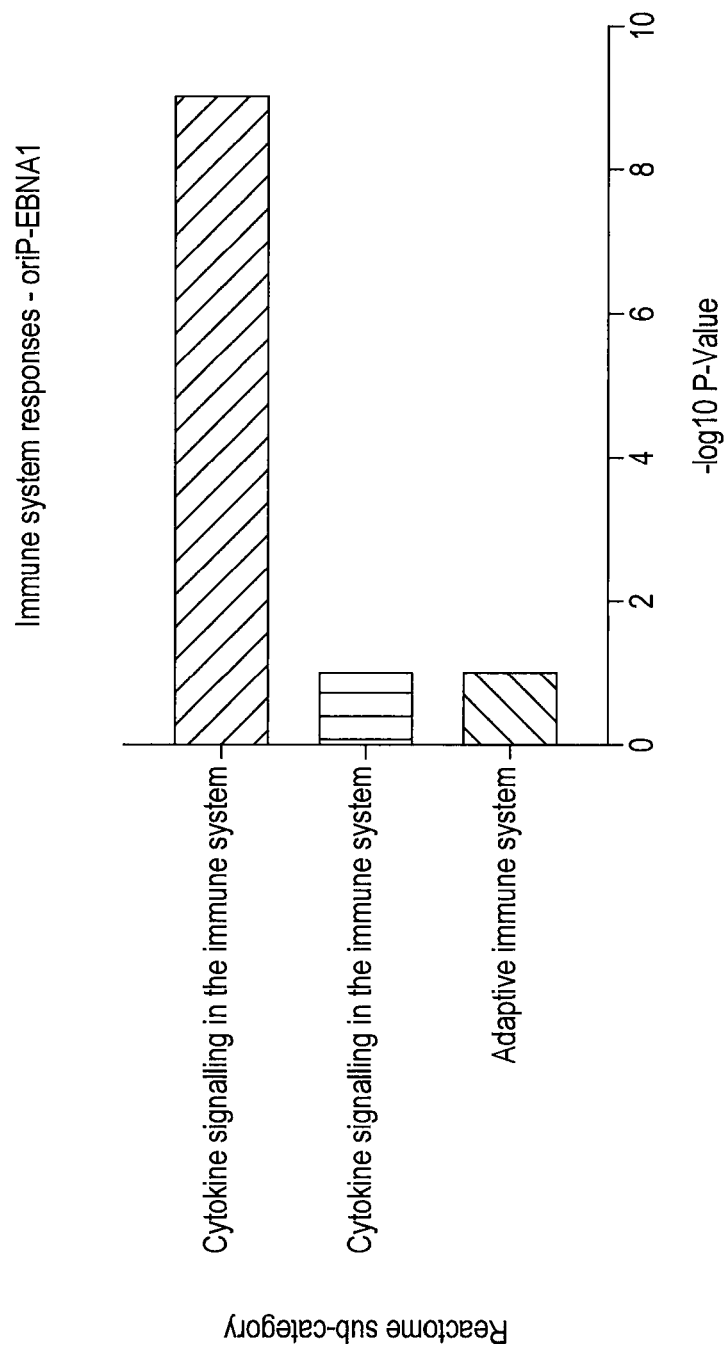

FIG. 20B depicts the reactome sub-categorisation. Results show that Interferon alpha, beta and gamma signalling are the most strongly over-represented in OriP/EBNA1 induced cells when compared to closed linear DNA (dbDNA) mediated iPSC generation. Interleukin and NF-KB inflammatory signalling are also over-represented.

Example 10: Quantitative RT-PCR

Quantitative RT-PCR was performed on iPSCs induced by either standard OriP/EBNA1 vectors or closed linear DNA. In particular, genes associated with interferon signalling, the innate immune system and inflammatory markers were investigated, or transcripts representing mesendoderm formation and early endoderm. Total RNA was extracted from the cells using standard methods.

Figure 21:
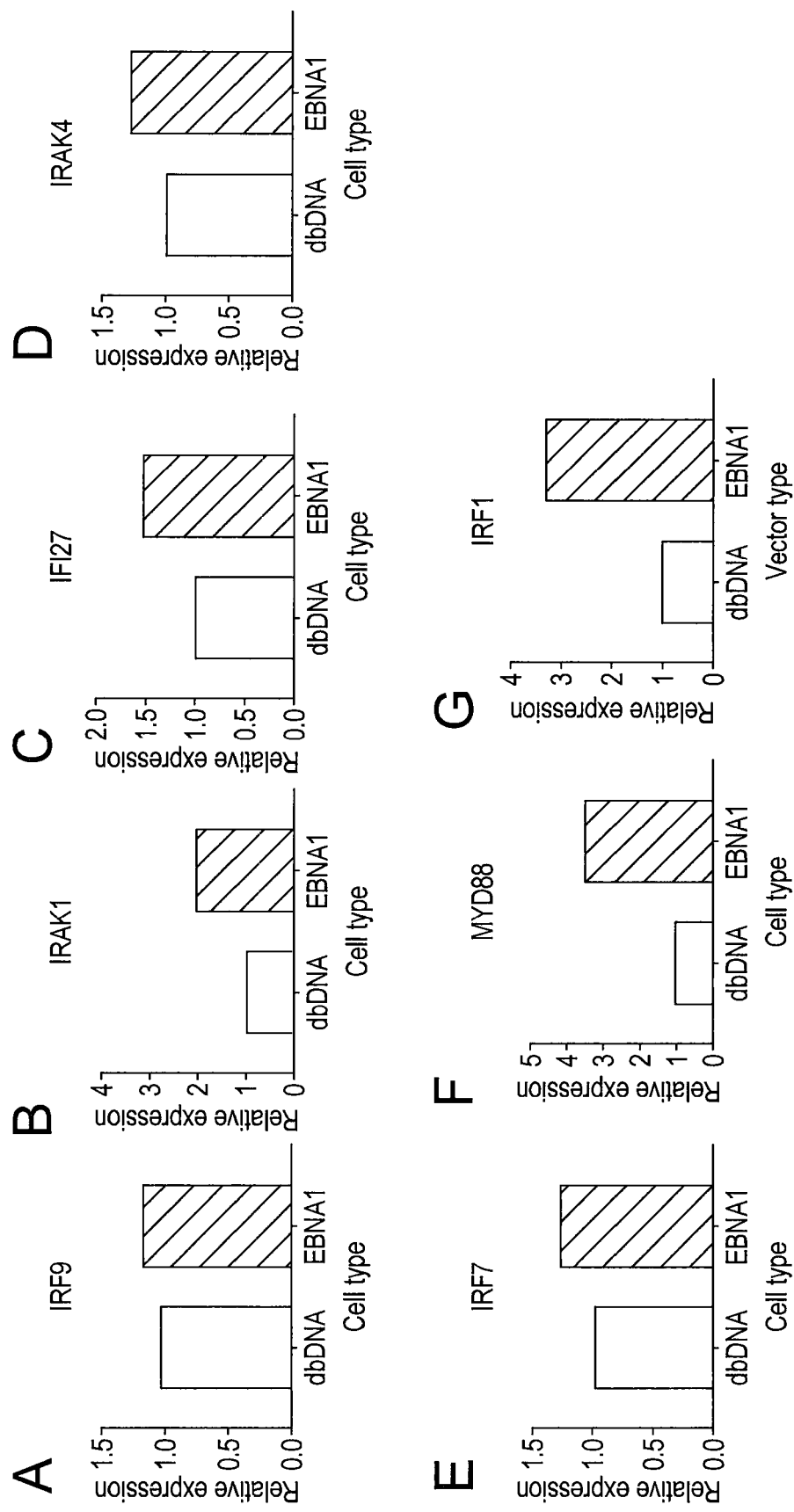
FIG. 21 (A to G). Quantitative RT-PCR comparison of Interferon (IFN) signalling in OriP/EBNA1 versus dbDNA (closed linear DNA) iPSC. Total RNA was extracted from iPSC generated using OriP/EBNA1 episomal plasmids or closed linear DNA vectors. All innate IFN signalling-associated transcripts were elevated in OriP/EBNA-iPSC compared to dbDNA-iPSC. The marker examined was.

The results found were are follows:

FIG. 21 (A to G) depicts the results of a quantitative RT-PCR and comparison of Interferon signalling in OriP/EBNA1-induced versus closed linear DNA (dbDNA)-induced iPSC. Total RNA was extracted from cells generated using OriP/EBNA1 episomal plasmids or closed linear DNA vectors. All innate IFN signalling-associated transcripts were elevated in OriP/EBNA-iPSC compared to dbDNA-iPSC.

FIG. 22 (A and B) depicts the results of a quantitative RT-PCR and comparison of inflammatory markers in OriP/EBNA1-induced versus closed linear DNA (dbDNA)-induced iPSC. Total RNA was extracted from iPSC generated using OriP/EBNA1 episomal plasmids or closed linear DNA vectors. HMOX1 (a marker of oxidative stress) and NFKB1 (a marker of inflammation) are upregulated in OriP/EBNA1-iPSC compared to closed linear DNA-iPSC.

FIG. 23 (A to C): depicts the upregulation of markers of differentiation in OriP/EBNA1-iPSC compared to closed linear DNA-iPSC (doggybone/dbDNA). Quantitative RT-PCR was used to evaluate transcripts representing mesendoderm formation and early endoderm as markers of early differentiation. In all instances there was increased markers of early differentiation in OriP/EBNA1-iPSC compared to closed linear DNA (dbDNA)-iPSC cultured under steady state conditions. Furthermore, the inventors noted increased expression of CDKN1A (p21), a cell cycle inhibitor, in OriP/EBNA1-iPSC compared to closed linear DNA-iPSC. CDKN1A-mediated inhibition of proliferation is a further indicator of differentiation of pluripotent stem cells.

The invention claimed is:

1. A method of producing induced pluripotent stem cells (iPSCs) comprising introducing one or more closed linear vector(s) encoding one or more reprogramming factors into a population of mature somatic cells, and culturing said mature somatic cells to effect expression of the one or more reprogramming factor(s), wherein said one or more closed linear vector(s) lacks sequences for chromosomal scaffold attachment.

2. The method of claim 1, wherein the one or more closed linear vectors includes two or more closed linear DNA vectors, each encoding one or more different reprogramming factors.

3. The method of claim 1, wherein said reprogramming factor is selected from one or more of: Oct 3/4, Sox2, Sox1, Sox3, Sox15, Sox18, Klf1, Klf2, Klf4, Klf5, c-myc, L-myc, and N-myc, NANOG, or LIN28.

4. The method of claim 1, wherein said closed linear DNA vector lacks any sequence for the knockdown of p53.

5. The method of claim 1, wherein said one or more reprogramming factors are operably linked to one or more promoters.

6. The method of claim 5, wherein the one or more reprogramming factors are operably linked to a same promoter on the one or more closed linear vectors.

7. The method of claim 1, wherein said one or more closed linear DNA vectors lacks one or more of:
   (i) bacterial CpG motifs;
   (ii) a bacterial origin of replication; or
   (iii) antibiotic resistance genes.

8. The method of claim 1, wherein said one or more closed linear vectors is a closed linear DNA vector introduced via transfection.

9. The method of claim 8, wherein the mature somatic cells are cultured for around 30 days after transfection or nucleofection prior to reprogramming being complete.

* * * * *